(12) United States Patent
Taugerbeck et al.

(10) Patent No.: US 7,955,664 B2
(45) Date of Patent: Jun. 7, 2011

(54) CHROMAN COMPOUNDS

(75) Inventors: Andreas Taugerbeck, Darmstadt (DE); Alexander Hahn, Gross-Gerau (DE); Achim Goetz, Alsbach-Haehnlein (DE)

(73) Assignee: Merck Patent Gesellschaft, Darmstadt (DE)

( * ) Notice: Subject to any disclaimer, the term of this patent is extended or adjusted under 35 U.S.C. 154(b) by 0 days.

(21) Appl. No.: 12/525,180

(22) PCT Filed: Dec. 11, 2007

(86) PCT No.: PCT/EP2007/010815
§ 371 (c)(1),
(2), (4) Date: Jul. 30, 2009

(87) PCT Pub. No.: WO2008/092491
PCT Pub. Date: Aug. 7, 2008

(65) Prior Publication Data
US 2010/0102274 A1  Apr. 29, 2010

(30) Foreign Application Priority Data

Jan. 31, 2007  (DE) .......................... 10 2007 004 699

(51) Int. Cl.
*C09K 19/32* (2006.01)
*C09K 19/34* (2006.01)
*C07D 311/04* (2006.01)
*C07D 319/08* (2006.01)
*C07D 407/02* (2006.01)
*C07D 407/14* (2006.01)

(52) U.S. Cl. ............... 428/1.1; 252/299.61; 252/299.62; 549/362; 549/365; 549/370; 549/398; 549/415

(58) Field of Classification Search ................... 549/362, 549/365, 398, 370, 415; 252/299.61, 299.62; 428/1.1
See application file for complete search history.

(56) References Cited

FOREIGN PATENT DOCUMENTS

| | | |
|---|---|---|
| DE | 102008004891 A1 | 8/2008 |
| EP | 1491612 A1 | 12/2004 |
| EP | 1690917 A1 | 8/2006 |
| JP | 2006199941 A | 8/2006 |
| JP | 2006199941 W | 8/2006 |
| WO | 2004046805 A1 | 6/2004 |
| WO | 2006012965 A1 | 2/2006 |
| WO | 2006040009 A2 | 4/2006 |
| WO | 2006079406 A1 | 8/2006 |
| WO | 2006125511 A1 | 11/2006 |
| WO | PCT/EP2007/010815 R | 4/2008 |
| WO | 2008092491 A1 | 8/2008 |

OTHER PUBLICATIONS

Caplus 1975: 147406.*
Beilstein Database. Accession Nos. 13931112, 1393116, 1396221, 1397495, 1974.
Beilstein Database. Accession Nos. 1657066, 1975.
Beilstein Database. Accession Nos. 366031, 368674, 1934.
Eiden, F. et al. "1,2-Bisbenzopyranyl-ethene." (Archiv Der Pharmazie), 1980, 120-128, 313:2.
Nakatani, K. et al. "Highly Efficient Photochemical Generation of o-Quinone Methide from Mannich Bases of Phenol Derivatives." (Tetrahedron Letters), 1997, 5005-5008, 38:28.
Sorell, Th. N. et al. "3,3-Disubstituted 2,2'-biphenols. Synthesis of nonplanar, tetradentate chelating ligands." (Journal of Organic Chemistry), 1985, 5765-5769, 50:26.

* cited by examiner

*Primary Examiner* — Shean C Wu
(74) *Attorney, Agent, or Firm* — Millen, White, Zelano & Branigan, P.C.

(57) ABSTRACT

The chroman compounds of the formula I according to the invention

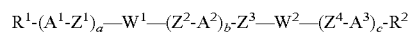

$$R^1\text{-}(A^1\text{-}Z^1)_a\text{---}W^1\text{---}(Z^2\text{-}A^2)_b\text{-}Z^3\text{---}W^2\text{---}(Z^4\text{-}A^3)_c\text{-}R^2$$

in which $R^1$, $A^1$, $A^2$, $A^3$, $W^1$, $W^2$, $Z^1$, $Z^2$, $Z^3$, $Z^4$, a, b and c have the meanings indicated in claim 1, have two moieties $W^1$ and $W^2$ derived from chroman. The compounds are suitable as components of anisotropic switching media, as used, for example, in liquid-crystal display devices.

24 Claims, No Drawings

CHROMAN COMPOUNDS

The invention relates to compounds of the formula I

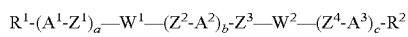

in which

W$^1$, W$^2$, independently of one another, denote a divalent group of the formula

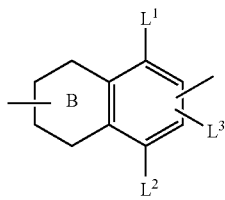

ring B denotes an unsaturated or partially saturated, six-membered ring in which one or two of the CH$_2$ groups have been replaced by O, where no two O atoms are adjacent, and in which —CH$_2$— may be replaced by —CHF— or —CF$_2$— or =CH— may be replaced by =CF—, L$^1$, L$^2$ and L$^3$
each, independently of one another, denote H, Cl, F, CN or CF$_3$, R$^1$, R$^2$, independently of one another, denote H, Cl, F, CN, SCN, SF$_5$, an alkyl radical having up to 15 C atoms which is unsubstituted, monosubstituted by CN or at least monosubstituted by halogen, where, in addition, one or more CH$_2$ groups in these radicals may each be replaced, independently of one another, by —O—, —CH=CH—, —CF=CF—, —CF=CH—, —C≡C—, —S—, —CO—, —(CO)O—, —O(CO)— or —O(CO)O— in such a way that O atoms are not linked directly to one another, A$^1$, A$^2$ and A$^3$
each, independently of one another, denote
(a) a trans-1,4-cyclohexylene radical, in which, in addition, one or more non-adjacent CH$_2$ groups may be replaced by —O— and/or —S—,
(b) a 1,4-phenylene radical, in which, in addition, one or two CH groups may be replaced by N,
(c) 1,4-cyclohexenylene,
(d) a radical from the group 1,3-bicyclo[1.1.1]pentylene, 1,4-bicyclo[2.2.2]octylene, cyclobut-1,3-diyl, spiro[3.3]heptane-2,6-diyl, naphthalene-2,6-diyl, tetrahydronaphthalene-2,6-diyl,
where the radicals (a) to (d) may be substituted by one or more, in particular one or two, fluorine atoms, Z$^1$, Z$^2$, Z$^3$ and Z$^4$
each, independently of one another, denote —(CO)O—, —O(CO)—, —CH$_2$O—, —OCH$_2$—, —CH$_2$CH$_2$—, —CH=CH—, —CH=CF—, —CF=CH—, —CF=CF—, —CHFCHF—, —CH$_2$CHF—, —CHFCH$_2$—, —C≡C—, —(CH$_2$)$_4$—, —CF$_2$O—, —OCF$_2$—, —C$_2$F$_4$—, —CH=CH—CH$_2$CH$_2$—, —CH$_2$CH$_2$OCF$_2$— or a single bond, and a, b, c, independently of one another, denote 0 or 1, where a+b+c adopts the value 0, 1 or 2.

The invention furthermore relates to the use of these compounds as components of liquid-crystalline media and to liquid-crystal and electro-optical display elements which contain the liquid-crystalline media according to the invention.

The compounds of the formula I can be used as components of liquid-crystalline media, in particular for displays based on the principle of the twisted cell, the guest-host effect, the effect of deformation of aligned phases or the effect of dynamic scattering.

Documents WO 2006/040009, JP 2006199941 A and EP 14910612 disclose chroman derivatives which have only one moiety having the chroman structure.

The invention was thus based on the object of finding novel, stable compounds which are suitable as component(s) of liquid-crystalline media, in particular for TN, STN, IPS and for further active-matrix displays.

Especially in the area of compounds of very high polarity (Δε>20), which are basically advantageous for many display applications, the problem of the ever-lower solubility of the compounds is encountered. This limits the use of such compounds in practice. It is therefore also an aim to find novel, highly polar, mesogenic compounds which can at the same time be dissolved in highly polar liquid-crystal mixtures in high proportions by weight. The overall consideration of the solubility of all compounds involved crucially determines the tendency towards crystallisation at low temperatures and therefore determines the stability of the displays at temperatures at the lower end of the application range.

An object of the present invention was in addition to provide compounds which have high positive dielectric anisotropy Δε. In addition, the compounds according to the invention should be thermally and photochemically stable. Furthermore, the compounds according to the invention should be usable in liquid-crystalline mixtures in that they do not impair or even improve the liquid-crystalline phase ranges thereof. It is furthermore advantageous if the compounds according to the invention have the broadest possible nematic phase.

The compounds of the formula I are eminently suitable as components of liquid-crystal mixtures of positive dielectric anisotropy, in particular if particularly high polarity of the host mixture is important, as is the case, for example, in the production of liquid-crystal displays using blue phases (cf. WO 2004/046805 and H. Kikuchi et al. Nature Materials (2002) 1, 64-68). It has been found that the chroman derivatives according to the invention are eminently suitable as components of anisotropic electro-optical media. They can be used to obtain stable, mesogenic switching media, in particular suitable for TN-TFT, STN and IPS displays and displays based on blue phases. Owing to their properties, the compounds are particularly suitable for use in the fast-switching displays operated in the area of blue phases, particularly as constituent of polymer-stabilised media, as disclosed, for example, in document EP 1690914 A1. The compounds according to the invention are stable chemically, thermally and to (UV) light. They are colourless in the pure state. They are also distinguished by strongly positive dielectric anisotropies Δε, due to which lower threshold voltages are necessary on use in optical switching elements. A further advantage of the compounds according to the invention is the high polarity of the two substituted chroman rings.

In addition, the compounds according to the invention have a broad nematic phase range.

Through a suitable choice of the ring members and/or the terminal substituents, the physical properties of the liquid crystals according to the invention can be varied in broad ranges.

The provision of the chroman derivatives according to the invention very generally considerably broadens the range of compounds which are suitable from various applicational points of view for the preparation of liquid-crystalline mixtures.

In the mixture with suitable co-components, the compounds according to the invention form liquid-crystalline mesophases in a temperature range which is favourably located for electro-optical use. Liquid-crystalline media having broad nematic phase ranges can be prepared from the compounds according to the invention and further substances.

The chroman derivatives have a broad range of applications. Depending on the choice of substituents, these compounds can serve as base materials of which liquid-crystalline media are predominantly composed. However, it is also possible to add liquid-crystalline base materials from other classes of compound to the compounds according to the invention in order, for example, to modify the dielectric and/or optical anisotropy of a dielectric of this type and/or to optimise its working-temperature range.

The invention thus relates to the compounds of the formula I and to the use of these compounds as components of liquid-crystalline media. The invention furthermore relates to liquid-crystalline media comprising at least one compound of the formula I and to liquid-crystal display elements, in particular electro-optical display elements, which contain media of this type.

For the purposes of the present application, the numbering of the atom positions of the formula indicated for $W^{1/2}$ is as follows:

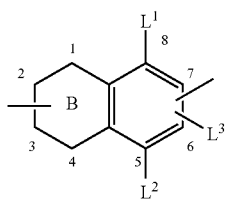

The free valence of ring B is located in position 2 or 3, that of the benzo ring is arranged in position 6 or 7. The substituent $L^3$ is localised at the remaining position 6 or 7. The ring system is preferably simultaneously connected at the mutually opposite positions 2/6 or 3/7 to the radical of the structure of the formula I, formally resulting in the substitution patterns (1) and (2):

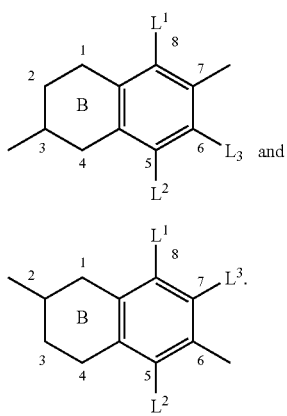

In view of the following definitions, substitution pattern (1) is preferred.

Ring B encompasses the following ring structures and mirror images thereof, with the optional substitution by fluorine atoms not being shown:

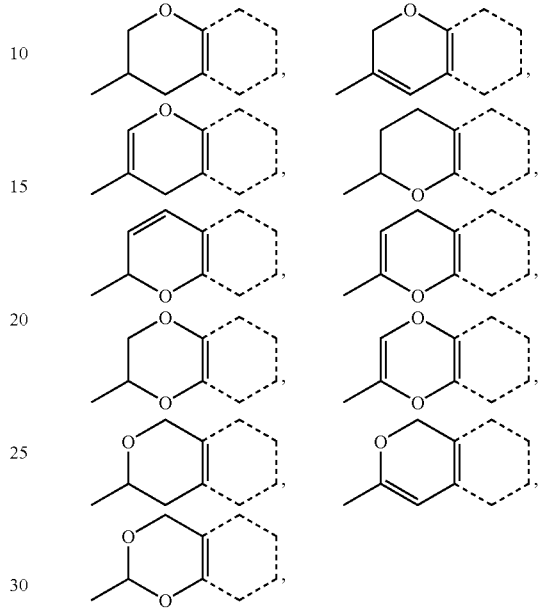

For the purposes of the present invention, all ring elements depicted are referred to for simplification as chroman rings and the associated compounds are referred to as chroman compounds. The compounds are therefore also referred to as bischromanyl derivatives. Ring B is partially saturated if it only contains the one double bond of the benzene ring. Ring B is referred to as unsaturated if it contains two double bonds.

Ring B is preferably not substituted by fluorine atoms. It preferably has precisely one oxygen atom. In the case where ring B has a second double bond, this is preferably arranged in the β-position (allyl position) to the oxygen atom. Ring B is preferably partially saturated.

The moieties $W^1$ and $W^2$ preferably have, independently of one another, the following meanings with the associated names:

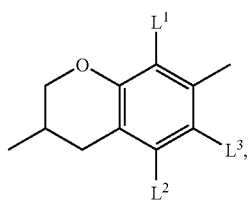

(w10)

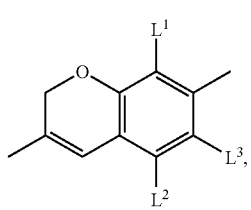

(w11)

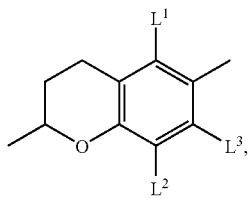

(w20)

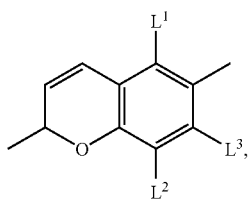

(w21)

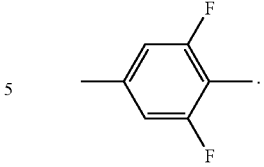

W$^1$ and W$^2$ particularly preferably adopt, independently of one another, the meaning of moiety (w10) or (w20), in particular (w10). W$^1$ and W$^2$ preferably adopt the same meaning. Likewise, W$^1$ preferably adopts the meaning (w20) and W$^2$ the meaning (w10).

The groups L$^1$, L$^2$ and L$^3$ in the formula I and the sub-formulae are preferably H, Cl, F, CF$_3$ or CN, particularly preferably H or F. At least one of the substituents L$^1$, L$^2$ and L$^3$ is preferably not hydrogen. L$^3$ preferably denotes F. L$^2$ is preferably a hydrogen atom. L$^1$ preferably denotes H or F.

For the group W$^2$, L$^1$ preferably denotes F; for the group W$^1$, L$^1$ preferably denotes H.

If they are not symmetrical, the ring systems indicated in groups (a) to (d) can be in both possible orientations. They are preferably arranged in such a way that the dipole of the ring is as far as possible aligned in the same direction and parallel with the same orientation to that of the chroman ring.

Z$^1$, Z$^2$ and Z$^4$ preferably denote a single bond, —CH$_2$CH$_2$—, —CH=CH—, CH$_2$O or —CF$_2$O—, and in particular a single bond or —CH$_2$CH$_2$—.

Preferred meanings for Z$^3$ are CH$_2$CH$_2$, CH$_2$O or a single bond, particularly a single bond.

The sum of the indices a, b and c in the formula I should be 0, 1 or 2 and is preferably 0 or 1.

Preference is given to compounds of the formula I and of all sub-formulae in which A$^1$, A$^2$ and/or A$^3$ denote cyclohexane-1,4-diyl, 1,3-dioxane-2,5-diyl, tetrahydropyran-2,5-diyl, 1,4-phenylene, 1,4-phenylene which is mono- or disubstituted by F or furthermore a radical from the group under point (d), as defined for formula I.

A$^1$, A$^2$ and A$^3$ particularly preferably denote a divalent group selected from the formulae:

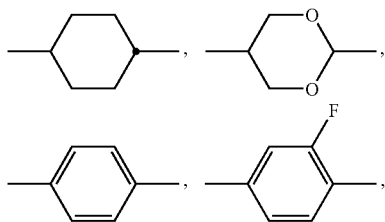

Z$^2$, A$^2$, b and Z$^3$ together are preferably selected in such a way that the group —(Z$^2$-A$^2$)-Z$^3$— does not denote a single bond.

R$^1$ preferably denotes an alkyl radical having up to 15 C atoms which is unsubstituted, monosubstituted by CN or at least mono-substituted by halogen, where, in addition, one or more CH$_2$ groups in these radicals may each be replaced, independently of one another, by —O—, —CH=CH—, —C≡C—, —S—, —CO—, —(CO)O—, —O(CO)— or —O(CO)O— in such a way that O atoms are not linked directly to one another.

R$^1$ particularly preferably denotes alkyl, alkoxy, alkenyl or alkenyloxy having up to 7 C atoms and very particularly preferably 1-5 C alkyl or 2-5 C alkenyl.

R$^2$ preferably denotes H, Cl, F, CN, SCN, SF$_5$, an alkyl radical having up to 15 C atoms which is monosubstituted by CN or at least monosubstituted by halogen, where, in addition, one or more CH$_2$ groups in these radicals may each be replaced, independently of one another, by —O—, —CH=CH—, —CF=CF—, —CF=CH—, —C≡C—, —S—, —CO—, —(CO)O—, —O(CO)— or —O(CO)O— in such a way that O atoms are not linked directly to one another.

R$^2$ particularly preferably denotes H, Cl, F, CN, SCN, SF$_5$, CF$_3$, CHF$_2$ or OCF$_3$, very particularly preferably F, OCF$_3$ or CN, of these in particular CN.

If R$^{1/2}$ denotes an alkyl radical and/or an alkoxy radical, this may be straight-chain or branched. It is preferably straight-chain, has 1, 2, 3, 4, 5, 6 or 7 C atoms and accordingly preferably denotes methyl, ethyl, propyl, butyl, pentyl, heptyl, hexyl, ethoxy, propoxy, butoxy, pentoxy, hexyloxy or heptyloxy, furthermore octyl, nonyl, decyl, undecyl, dodecyl, tridecyl, tetradecyl, pentadecyl, methoxy, octyloxy, nonyloxy, decyloxy, undecyloxy, dodecyloxy, tridecyloxy or tetradecyloxy.

If R$^{1/2}$ denotes an alkyl radical in which one CH$_2$ group has been replaced by —CH=CH—, this may be straight-chain or branched. It is preferably straight-chain and has 2 to 10 C atoms. Accordingly, it denotes, in particular, vinyl, prop-1- or -2-enyl, but-1-, -2- or -3-enyl, pent-1-, -2-, -3- or -4-enyl, hex-1-, -2-, -3-, -4- or -5-enyl, hept-1-, -2-, -3-, -4-, -5- or -6-enyl, oct-1-, -2-, -3-, -4-, -5-, -6- or -7-enyl, non-1-, -2-, -3-, -4-, -5-, -6-, -7- or -8-enyl, dec-1-, -2-, -3-, -4-, -5-, -6-, -7-, -8- or -9-enyl.

If R$^{1/2}$ denotes an alkyl radical in which one CH$_2$ group has been replaced by —O— and one has been replaced by —CO—, these are preferably adjacent. These thus contain an acyloxy group —CO—O— or an oxycarbonyl group —O—CO—. These are preferably straight-chain and have 2 to 6 C atoms. Accordingly, they denote in particular acetoxy, propionyloxy, butyryloxy, pentanoyloxy, hexanoyloxy, acetoxymethyl, propionyloxymethyl, butyryloxymethyl, pentanoyloxymethyl, 2-acetoxyethyl, 2-propionyloxyethyl, 2-butyryloxyethyl, 3-acetoxypropyl, 3-propionyloxypropyl, 4-acetoxybutyl, methoxycarbonyl, ethoxycarbonyl, propoxycarbonyl, butoxycarbonyl, pentoxycarbonyl, methoxycarbonylmethyl, ethoxycarbonylmethyl, propoxycarbonylmethyl, butoxycarbonylmethyl, 2-(methoxycarbonyl)ethyl, 2-(ethoxycarbonyl)ethyl, 2-(propoxycarbonyl)ethyl, 3-(methoxycarbonyl)propyl, 3-(ethoxycarbonyl)propyl, 4-(methoxycarbonyl)butyl.

If $R^{1/2}$ denotes an alkyl radical in which one $CH_2$ group has been replaced by unsubstituted or substituted —CH═CH— and an adjacent $CH_2$ group has been replaced by CO or CO—O or O—CO, this may be straight-chain or branched. It is preferably straight-chain and has 4 to 13 C atoms. Accordingly, it denotes in particular acryloyloxymethyl, 2-acryloyloxyethyl, 3-acryloyloxypropyl, 4-acryloyloxybutyl, 5-acryloyloxypentyl, 6-acryloyloxyhexyl, 7-acryloyloxyheptyl, 8-acryloyloxyoctyl, 9-acryloyloxynonyl, 10-acryloyloxydecyl, methacryloyloxymethyl, 2-methacryloyloxyethyl, 3-methacryloyloxypropyl, 4-methacryloyloxybutyl, 5-methacryloyloxypentyl, 6-methacryloyloxyhexyl, 7-methacryloyloxyheptyl, 8-methacryloyloxyoctyl, 9-methacryloyloxynonyl.

If $R^{1/2}$ denotes an alkyl or alkenyl radical which is mono-substituted by CN, this radical is preferably straight-chain, and the substitution by CN is in the ω-position.

If $R^{1/2}$ denotes an alkyl or alkenyl radical which is at least mono-substituted by halogen, this radical is preferably straight-chain, and halogen is preferably F or Cl. In the case of polysubstitution, halogen is preferably F. The resultant radicals also include perfluorinated radicals. In the case of monosubstitution, the fluorine or chlorine substituent may be in any desired position, but is preferably in the ω-position.

For the purposes of the present invention, halogen denotes fluorine, chlorine, bromine or iodine, preferably Br, Cl or F, particularly preferably Cl or F, and in particular fluorine.

Compounds of the formula I which contain wing groups $R^{1/2}$ which are suitable for polymerisation reactions are suitable for the preparation of mesogenic polymers, also in combination with other monomers. These polymers are suitable for the stabilisation of a mesophase which predominates under the polymerisation conditions.

Compounds of the formula I containing branched wing groups $R^1$ may occasionally be of importance owing to still further improved solubility in the conventional liquid-crystalline base materials, but in particular as chiral dopants if they are optically active. The formula I encompasses both the racemates of these compounds and also the optical antipodes, and mixtures thereof. Smectic compounds of this type are suitable as components of ferroelectric materials.

Compounds of the formula I having $S_A$ phases are suitable, for example, for thermally addressed displays.

Branched groups of this type generally contain not more than one chain branch. Preferred branched radicals R are isopropyl, 2-butyl (=1-methylpropyl), isobutyl (=2-methylpropyl), 2-methylbutyl, isopentyl (=3-methylbutyl), 2-methylpentyl, 3-methylpentyl, 2-ethylhexyl, 2-propylpentyl, isopropoxy, 2-methylpropoxy, 2-methylbutoxy, 3-methylbutoxy, 2-methylpentoxy, 3-methylpentoxy, 2-ethylhexyloxy, 1-methylhexyloxy, 1-methylheptyloxy.

In a preferred embodiment, the compounds of the formula I are characterised in that
c denotes 1,
$Z^4$ denotes $CF_2O$, and
$A^3$ denotes a divalent group selected from the formulae

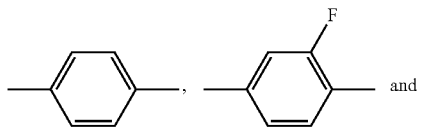

-continued

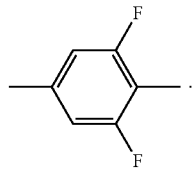

Of the compounds of the formula I and of all sub-formulae, preference is given to those in which one or more of the radicals present therein have one of the preferred meanings indicated. Further preferred embodiments may be derived by the skilled person from the details of the example part and may be generalized for his purposes.

In the compounds of the formula I, preference is given to the stereoisomers in which the cyclohexane rings are trans-1,4-disubstituted. Those of the above-mentioned formulae which can contain a plurality of stereoisomers in each case encompass all possible stereoisomers.

Preferred smaller groups of compounds of the formula I are, in addition, those of the sub-formulae Ia to If

| | |
|---|---|
| $R^1$—$W^1$—$W^2$—$R^2$ | Ia |
| $R^1$—$W^1$—$Z^3$—$W^2$—$R^2$ | Ib |
| $R^1$-$A^1$-$W^1$—$W^2$—$R^2$ | Ic |
| $R^1$—$W^1$-$A^2$-$W^2$—$R^2$ | Id |
| $R^1$—$W^1$—$W^2$-$A^3$-$R^2$ | Ie |
| $R^1$—$W^1$—$W^2$—$Z^4$-$A^3$-$R^2$ | If |

The 1,4-cyclohexenylene group preferably has the following structures:

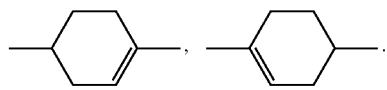

The compounds of the formula I are prepared by methods known per se, as described in the literature (for example in the standard works, such as Houben-Weyl, Methoden der organischen Chemie [Methods of Organic Chemistry], Georg-Thieme-Verlag, Stuttgart), to be precise under reaction conditions which are known and suitable for the said reactions.

Use can also be made here of variants known per se which are not mentioned here in greater detail.

Starting from simple benzene derivatives, compounds of the formula I according to the invention can be prepared by the following methods.

The synthesis of the compounds of the formula I can be carried out, for example, using halogenated benzochromenes (compound 2), the preparation of which is described in document WO 2006/040009.

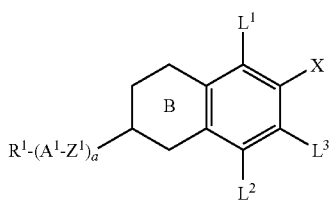

Compounds of this type can either be reacted directly (for example by transition metal-catalysed arylation of ketones, malonates, olefins, etc., Scheme 1) or modified in a suitable manner for further reaction for the synthesis of the compounds of the formula I in accordance with the following schemes using standard transformations, as are known to the person skilled in the art and described in the literature (Houben Weyl, Methoden der organischen Chemie [Methods of Organic Chemistry], Georg Thieme Verlag, Stuttgart, New York, 4th Edn. 1993).

Scheme 1. Synthesis of compounds according to the invention or suitable precursors thereof from the intermediate compound 2.

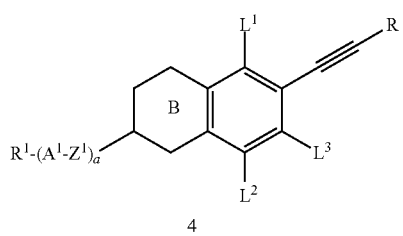

R = alkyl, aryl, COOR

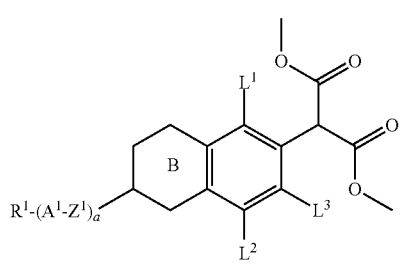

R = alkyl, aryl

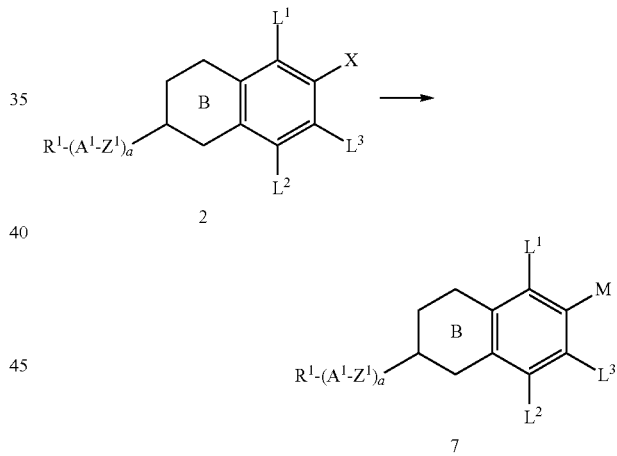

R is an organic radical as in formula I, for example (in each case optionally substituted) alkyl or aryl.

Thus, for example, metallation of compound 2 (for X=H: using LDA, BuLi, Schlosser base; for X=Hal: using Mg, iPrMgHal, etc.) and optionally transmetallation using, for example, zinc halides, gives, inter alia, the arylmetal compounds 7 (Scheme 2), which can be converted in a versatile manner into further novel synthetic building blocks (Scheme 3).

Scheme 2. Metallation of the intermediate compound 2 for the formation of the reactive metal derivative 7.

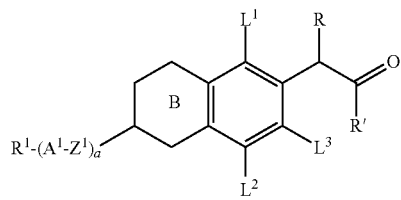

X = H, Hal
M = Li, Na, K, MgHal, Mg$_{1/2}$, ZnHal, Zn$_{1/2}$,

Scheme 3. Possible reactions of the metal derivative 7 for the synthesis of compounds according to the invention. Ar can be a substituted aromatic ring as in the compounds of the formula I according to the invention.

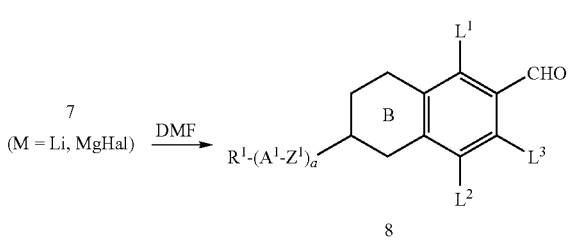

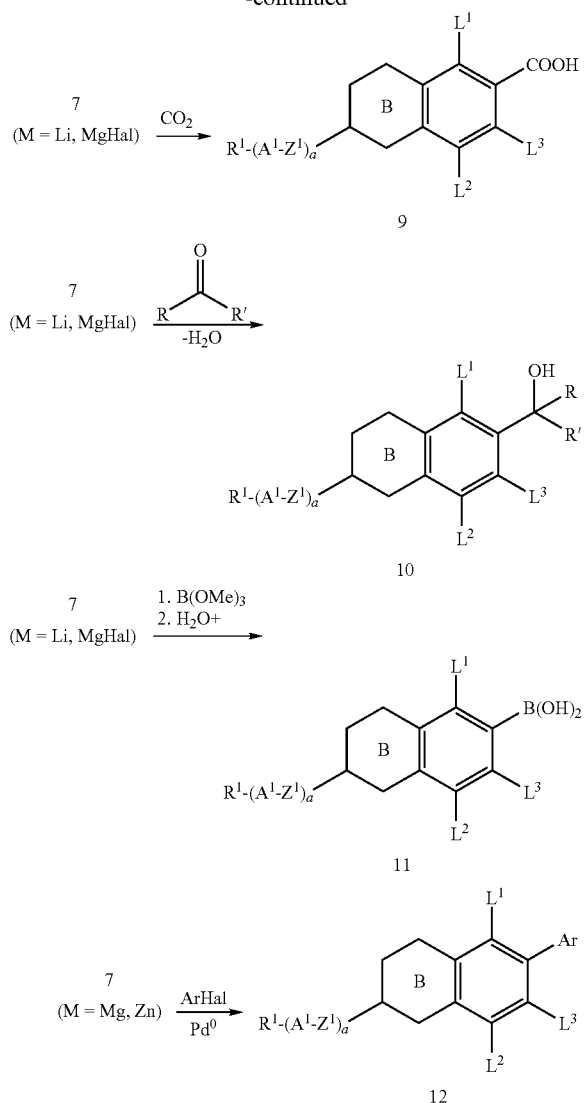

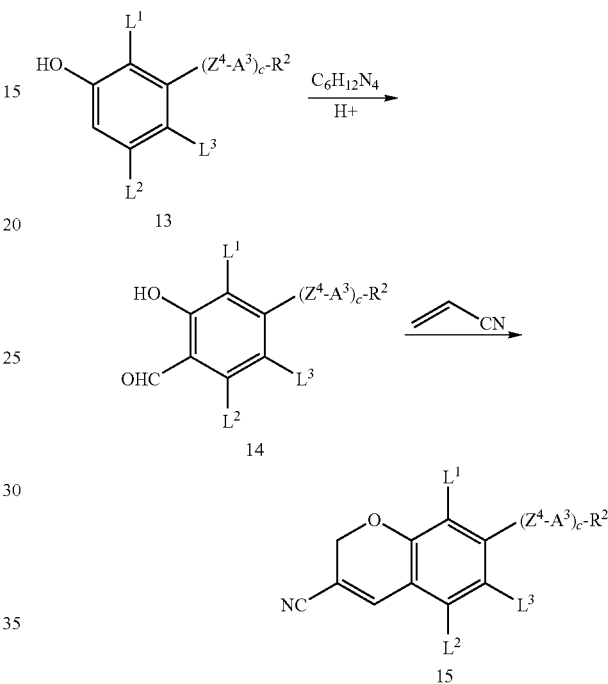

Versatile access to synthetic building blocks for linking to the cycloaliphatic ring B is available starting from salicylaldehydes 14, which are readily accessible, for example, by the method of Duff (J. C. Duff and E. J. Bills, J. Chem. Soc. (1932) 1987; (1934) 1305; J. C. Duff, ibid. (1941) 547; (1945) 276) from phenols using hexamethylenetetramine (Scheme 4).

Scheme 4. Synthesis of the carbonitrile compound 15 via the intermediate 14.

The condensation of the salicylaldehydes 14 with acrylonitrile analogously to L. D. Wise et al., J. Med. Chem. (1988) 31, 688-691 then gives carbonitriles (15), which can be modified in a manner familiar to the person skilled in the art in accordance with Scheme 5 and Scheme 6 to give a multiplicity of synthetic building blocks.

Scheme 5. Possible derivatisations of the carbonitrile compound 15 (part 1).

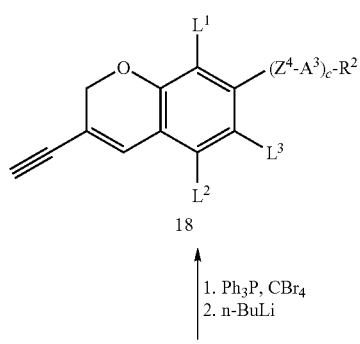

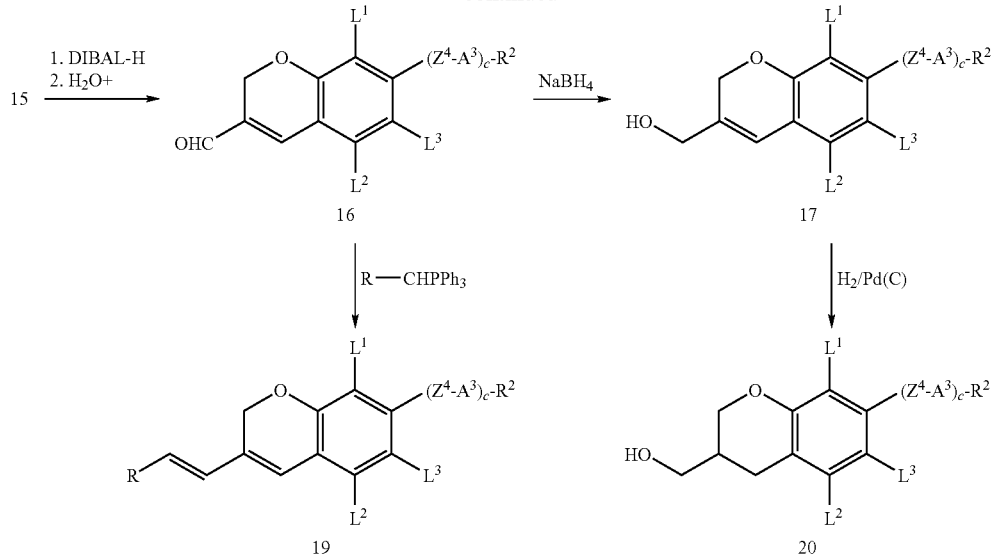

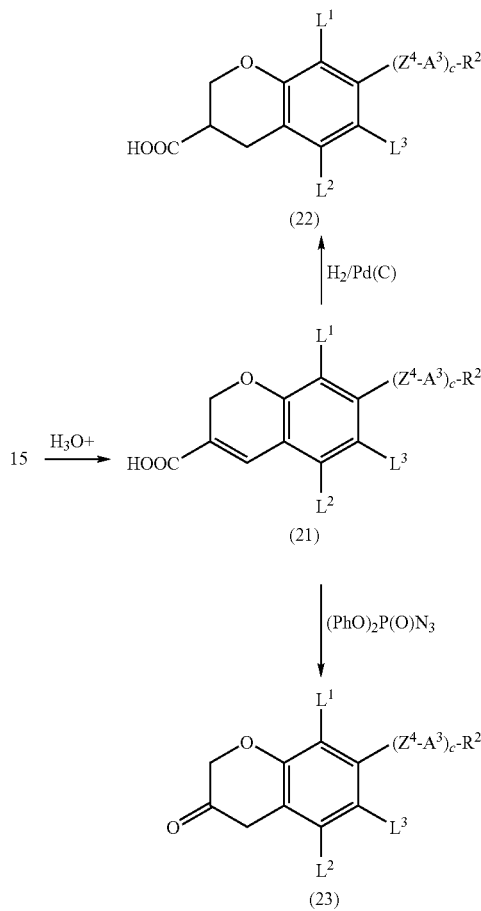

Scheme 6. Possible derivatisations of the carbonitrile compound 15 (part 2).

The following schemes show some preferred reactions of the synthetic building blocks described in Schemes 1 to 6 to give the target compounds of the formula I. Thus, directly linked bischromanyl derivatives can be obtained from the malonates 5 analogously to the synthesis of the chromans themselves (cf. WO 2006/040009) (Scheme 7).

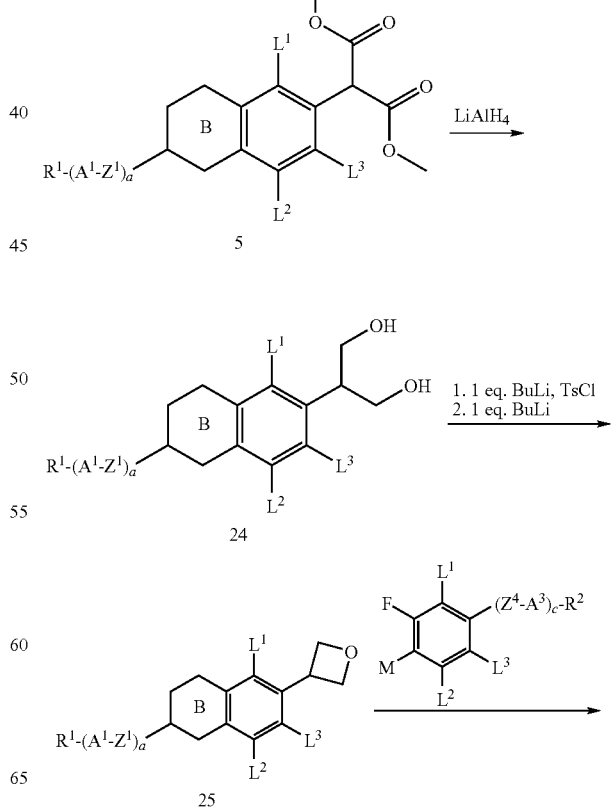

Scheme 7. Synthesis of directly linked bischromanyl derivatives (b = 0, $Z^3$ = single bond).

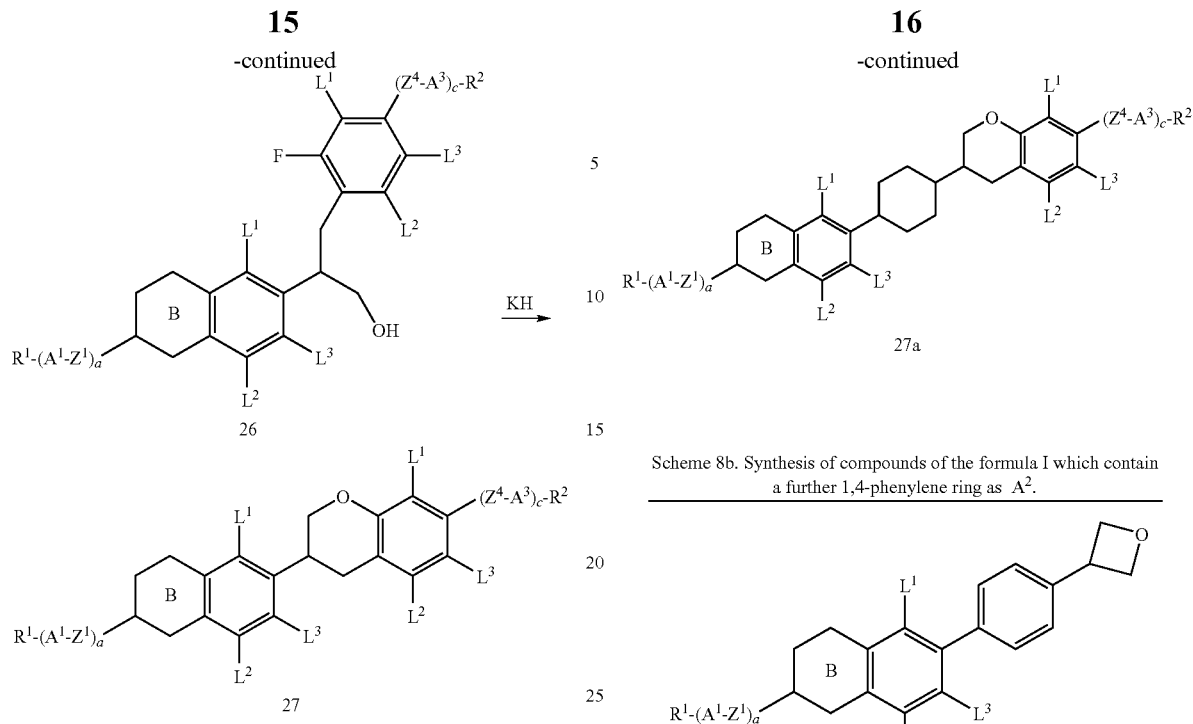

The compounds 25 here may also contain further rings $A^2$ (at position 7), which are accessible in an analogous manner and can be converted into the corresponding end products 27a and 27b (Schemes 8a, 8b)

Scheme 8a. Synthesis of compounds of the formula I which contain a 1,4-cyclohexanediyl group as further ring $A^2$.

Scheme 8b. Synthesis of compounds of the formula I which contain a further 1,4-phenylene ring as $A^2$.

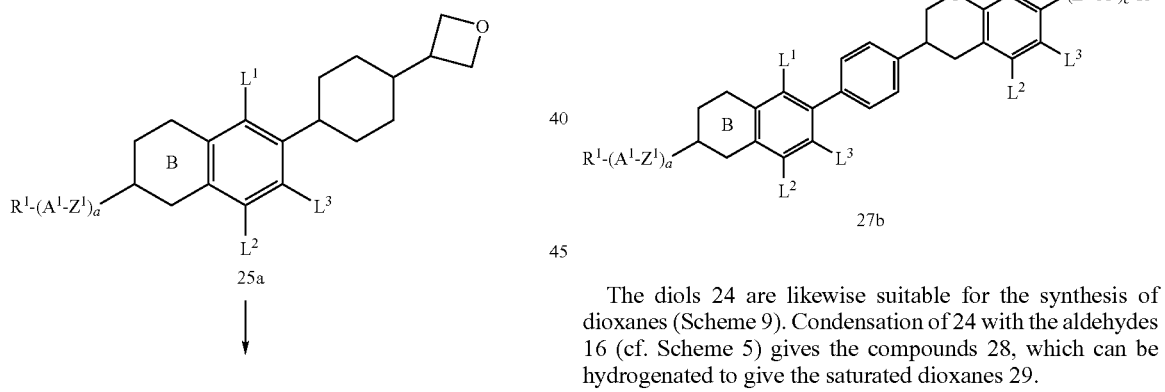

The diols 24 are likewise suitable for the synthesis of dioxanes (Scheme 9). Condensation of 24 with the aldehydes 16 (cf. Scheme 5) gives the compounds 28, which can be hydrogenated to give the saturated dioxanes 29.

Scheme 9. Synthesis of dioxane derivatives 29.

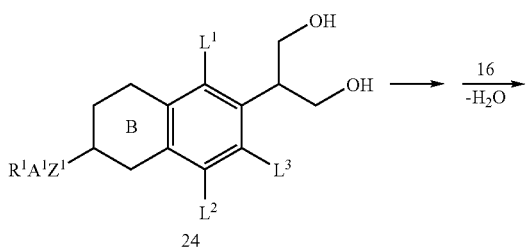

-continued

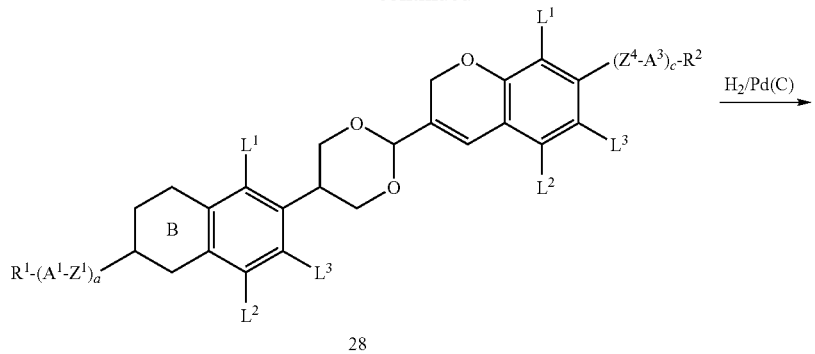
28

| H₂/Pd(C) →

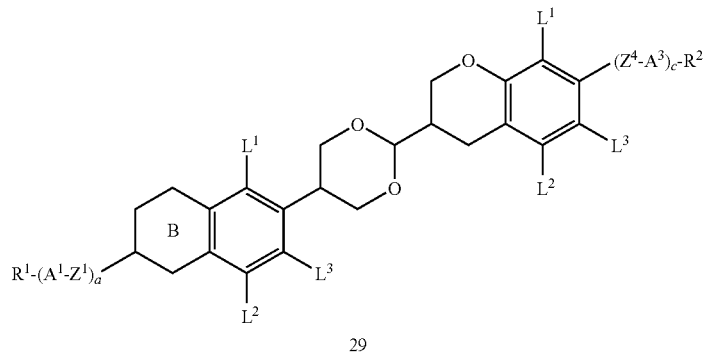
29

A possible synthetic route to compounds of the formula I containing a simple bridge Z³ between the chroman rings (i.e. without ring A²) is shown in Scheme 10. Thus, for example, the acetylene derivatives 18 can be reacted with the aryl halides 2 in a Negishi coupling to give the compounds 30a, which then, after hydrogenation, give the ethylene-bridged compounds 30b.

Scheme 10. Synthetic route to compounds of the formula I containing a simple bridge Z³ between the chroman rings (30a/30b).

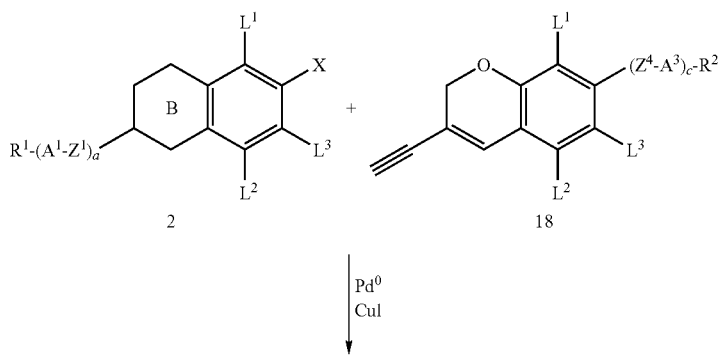

| Pd⁰
| CuI
↓

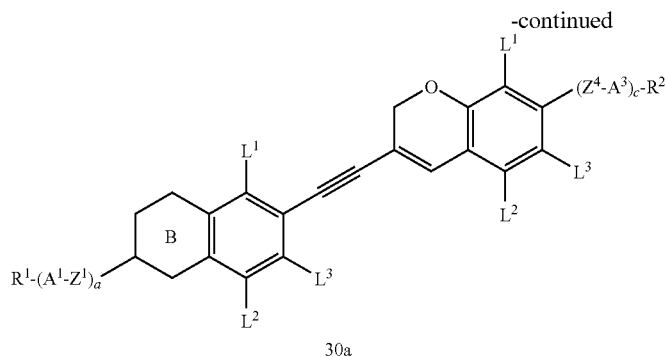

30a

↓ H₂/Pd(C)

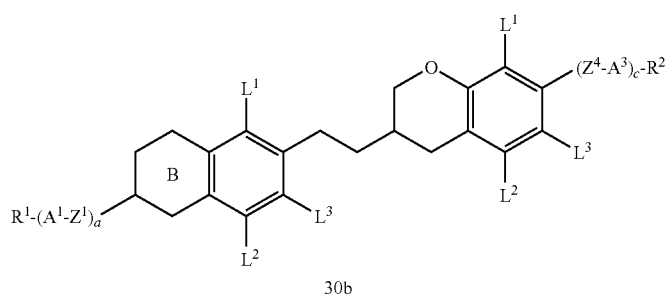

30b

Structural isomers of the salicylaldehydes 14 (cf. Scheme 4), which are accessible in an analogous manner and are likewise described in WO 2006/040009, can serve for the synthesis of benzo[1,3]dioxins 33 as shown in Scheme 11, for example through acetalisation using the aldehydes 8 as starting material (cf. Scheme 3).

Scheme 11. Synthesis of chroman derivatives 33 of the benzo-[1,3] dioxin type.

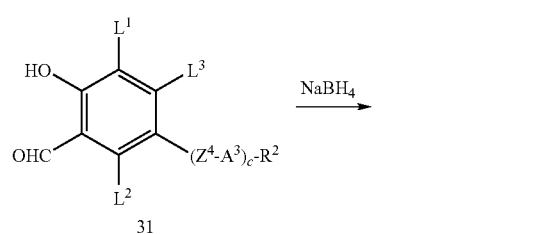

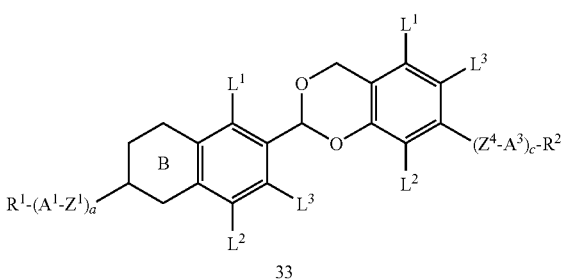

33

Scheme 12 shows the synthesis of chromans of type (w21) and (w20). Through Petasis reaction by the method of Q. Wang, M. G. Finn, *Org. Lett.* (2000) 2, 4063-4065, the compounds 35 can be used for the synthesis of α-substituted chroman compounds of type (w21) (chromenes), which can then be hydrogenated to give the chromans 37 (Scheme 12). The boronic acids 34 are obtained by hydroboration of the alkynes 4 (cf. Scheme 1) by processes known from the literature.

Scheme 12. Synthesis of α-substituted chromans of type (w21) and (w20).
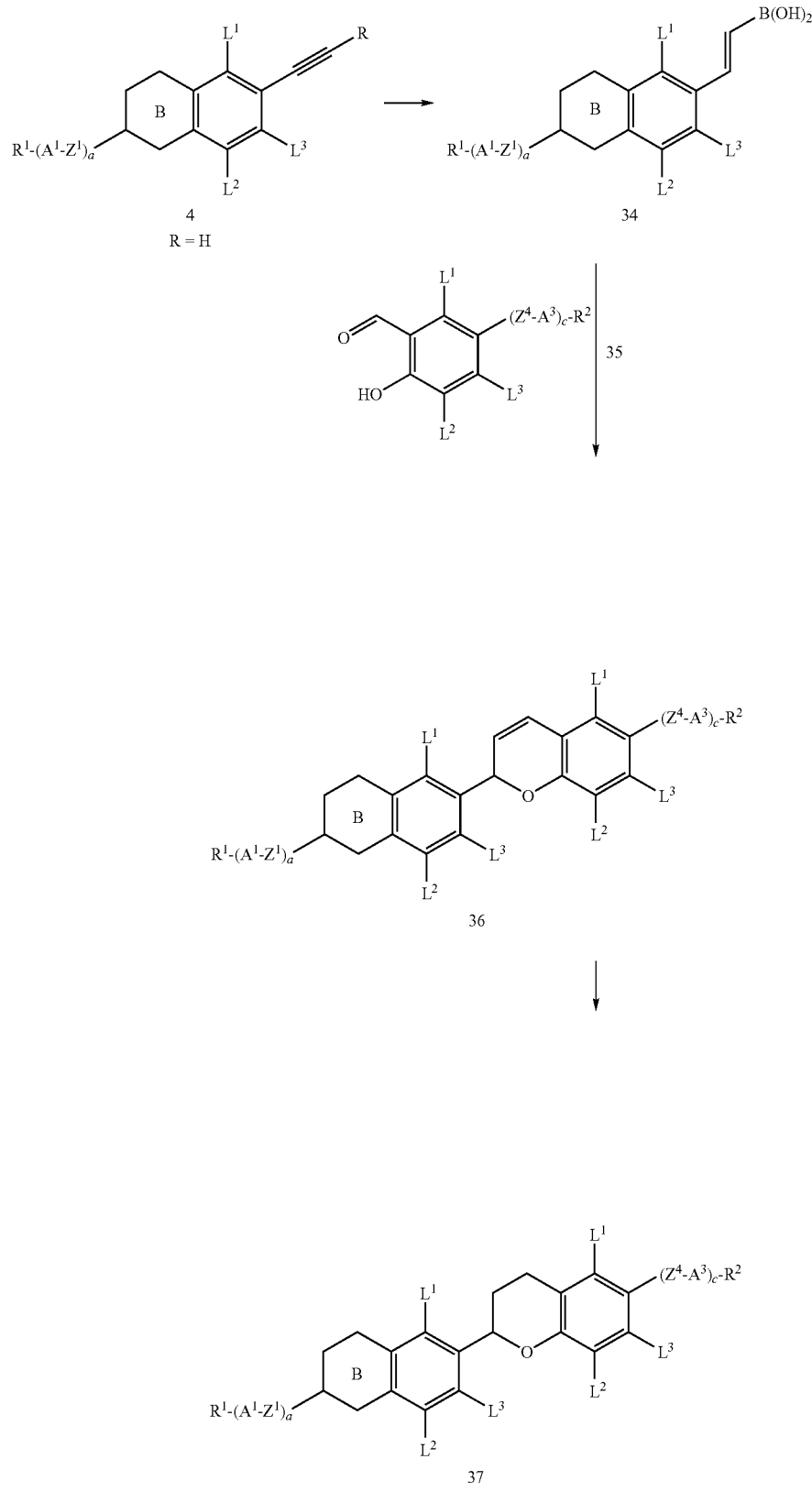

Scheme 13. Preparation of chroman compounds of the isochro-man type.

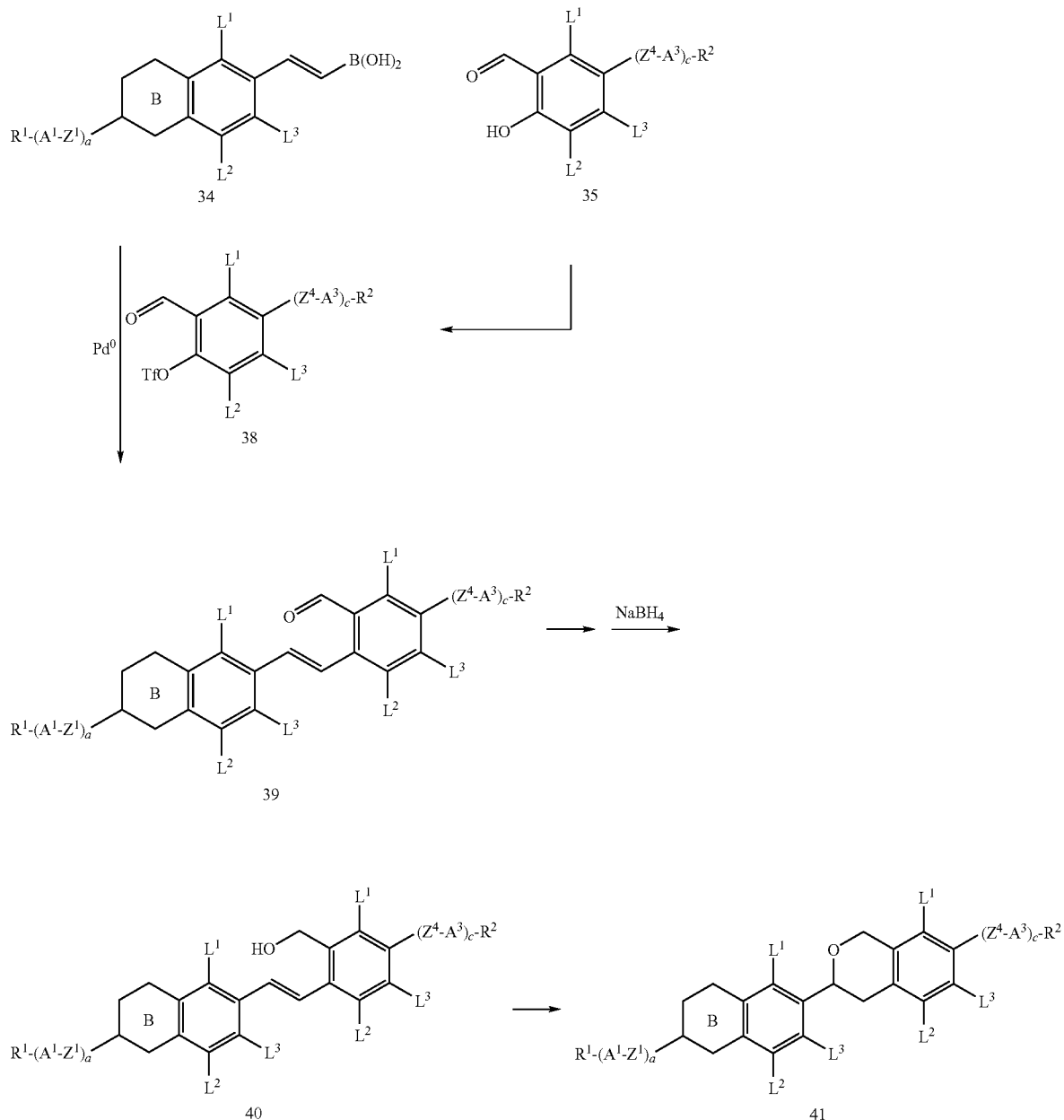

Isochromans can likewise be prepared starting from salicylaldehydes 35 (for example 41, Scheme 13). Here, the salicylaldehydes 35 are firstly reacted, for example, with trifluoromethanesulfonic anhydride to give the triflates 38, from which the stilbenes 39 can then be prepared in a Suzuki reaction with the boronic acids 34 (see above). After reduction of the aldehyde group to the alcohol 40, for example by reaction with sodium borohydride, the isochromans 41 can then be obtained by base-catalysed cyclisation by the method of R. G. F Giles et al., J. Chem. Soc. Perkin 1 (1984) 2389-2396.

An embodiment of the invention is therefore also a first process for the preparation of compounds of the formula I in which $A^2$ is a dioxane ring and $Z^2$ and $Z^3$ are single bonds, which is characterised in that it includes a process step in which a compound of the formula II

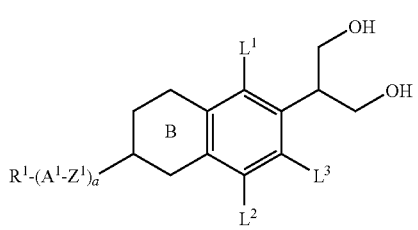

II in which the radicals are as defined above for formula I, is reacted with an aldehyde of the formula III

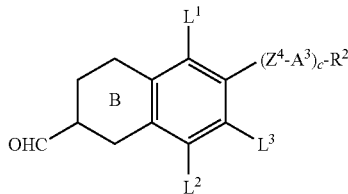

in which the radicals are as defined above for formula I, with formation of a dioxane ring. The process is preferably carried out in an organic solvent with acid catalysis. It is advantageous here continuously to remove the water formed from the reaction, for example by means of an adsorbent or by azeotropic distillation. The formula III is preferably that of compound 16 (Scheme 5).

A further embodiment of the invention is a second process for the preparation of compounds of the formula I in which b is 0 and $Z^3$ is a single bond, which is characterised in that it includes a process step in which an oxetane compound of the formula IV

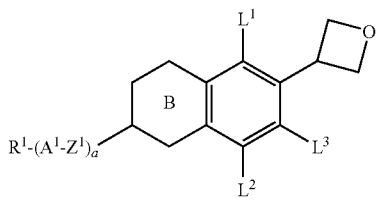

in which the radicals are as defined above for formula I, is reacted with a bromobenzene derivative of the formula V

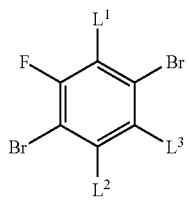

in which the radicals are as defined above for formula I, to give a compound of the formula

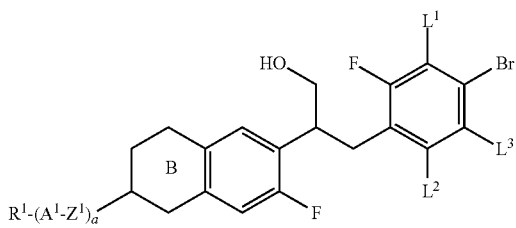

and, in a further process step, is converted into compounds of the formula I or a precursor thereof by cyclisation. The cyclisation is preferably effected by a strong base. The reaction is preferably carried out in an inert solvent. A suitable strong base is, for example, potassium hydride.

Further possible synthetic routes for chroman compounds are disclosed in document WO 2006/040009 on pages 42-52 and in the examples. The last-mentioned disclosures are incorporated here by way of reference.

The liquid-crystalline media according to the invention preferably comprise 2 to 40, in particular 4 to 30, components as further constituents besides one or more compounds according to the invention. These media very particularly preferably comprise 7 to 25 components besides one or more compounds according to the invention. These further constituents are preferably selected from nematic or nematogenic (monotropic or isotropic) substances, in particular substances from the classes of the azoxybenzenes, benzylideneanilines, biphenyls, terphenyls, phenyl or cyclohexyl benzoates, phenyl or cyclohexyl esters of cyclohexanecarboxylic acid, phenyl or cyclohexyl esters of cyclohexylbenzoic acid, phenyl or cyclohexyl esters of cyclohexylcyclohexanecarboxylic acid, cyclohexylphenyl esters of benzoic acid, of cyclohexanecarboxylic acid or of cyclohexylcyclohexanecarboxylic acid, phenylcyclohexanes, cyclohexylbiphenyls, phenylcyclohexylcyclohexanes, cyclohexylcyclohexanes, cyclohexylcyclohexylcyclohexanes, 1,4-biscyclohexylbenzenes, 4,4'-biscyclohexylbiphenyls, phenyl- or cyclohexylpyrimidines, phenyl- or cyclohexylpyridines, phenyl- or cyclohexyldioxanes, phenyl- or cyclohexyl-1,3-dithianes, 1,2-diphenylethanes, 1,2-dicyclohexylethanes, 1-phenyl-2-cyclohexylethanes, 1-cyclohexyl-2-(4-phenylcyclohexyl)ethanes, 1-cyclohexyl-2-biphenylylethanes, 1-phenyl-2-cyclohexylphenylethanes, optionally halogenated stilbenes, benzyl phenyl ethers, tolans and substituted cinnamic acids. The 1,4-phenylene groups in these compounds may also be fluorinated.

The most important compounds suitable as further constituents of media according to the invention can be characterised by the formulae 1, 2, 3, 4 and 5:

| | |
|---|---|
| R'-L-E-R" | 1 |
| R'-L-COO-E-R" | 2 |
| R'-L-OOC-E-R" | 3 |
| R'-L-CH$_2$CH$_2$-E-R" | 4 |
| R'-L-C≡C-E-R" | 5 |

In the formulae 1, 2, 3, 4 and 5, L and E, which may be identical or different, each, independently of one another, denote a divalent radical from the group formed by -Phe-, -Cyc-, -Phe-Phe-, -Phe-Cyc-, -Cyc-Cyc-, -Pyr-, -Dio-, -G-Phe- and -G-Cyc- and their mirror images, where Phe denotes unsubstituted or fluorine-substituted 1,4-phenylene, Cyc denotes trans-1,4-cyclohexylene or 1,4-cyclohexenylene, Pyr denotes pyrimidine-2,5-diyl or pyridine-2,5-diyl, Dio denotes 1,3-dioxane-2,5-diyl and G denotes 2-(trans-1,4-cyclohexyl)ethyl.

One of the radicals L and E is preferably Cyc, Phe or Pyr. E is preferably Cyc, Phe or Phe-Cyc. The media according to the invention preferably comprise one or more components selected from the compounds of the formulae 1, 2, 3, 4 and 5 in which L and E are selected from the group consisting of Cyc, Phe and Pyr and simultaneously one or more components selected from the compounds of the formulae 1, 2, 3, 4 and 5 in which one of the radicals L and E is selected from the group consisting of Cyc, Phe and Pyr and the other radical is selected from the group consisting of -Phe-Phe-, -Phe-Cyc-, -Cyc-Cyc-, -G-Phe- and -G-Cyc-, and optionally one or more components selected from the compounds of the formulae 1, 2, 3, 4 and 5 in which the radicals L and E are selected from the group consisting of -Phe-Cyc-, -Cyc-Cyc-, -G-Phe- and -G-Cyc-.

In a smaller sub-group of the compounds of the formulae 1, 2, 3, 4 and 5, R' and R" each, independently of one another, denote alkyl, alkenyl, alkoxy, alkoxyalkyl, alkenyloxy or alkanoyloxy having up to 8 carbon atoms. This smaller sub-group is called group A below, and the compounds are referred to by the sub-formulae 1a, 2a, 3a, 4a and 5a. In most of these compounds, R' and R" are different from one another, one of these radicals usually being alkyl, alkenyl, alkoxy or alkoxyalkyl.

In another smaller sub-group of the compounds of the formulae 1, 2, 3, 4 and 5, which is referred to as group B, R" denotes —F, —Cl, —NCS or —(O)$_i$CH$_{3-(k+l)}$F$_k$Cl$_l$, where i is 0 or 1 and k+l is 1, 2 or 3; the compounds in which R" has this meaning are referred to by the sub-formulae 1b, 2b, 3b, 4b and 5b. Particular preference is given to compounds of the sub-formulae 1b, 2b, 3b, 4b and 5b in which R" has the meaning —F, —Cl, —NCS, —CF$_3$, —OCHF$_2$ or —OCF$_3$.

In the compounds of the sub-formulae 1b, 2b, 3b, 4b and 5b, R' has the meaning indicated for the compounds of the sub-formulae 1a-5a and is preferably alkyl, alkenyl, alkoxy or alkoxyalkyl.

In a further smaller sub-group of the compounds of the formulae 1, 2, 3, 4 and 5, R" denotes —CN. This sub-group is referred to below as group C, and the compounds of this sub-group are correspondingly described by the sub-formulae 1c, 2c, 3c, 4c and 5c. In the compounds of the sub-formulae 1c, 2c, 3c, 4c and 5c, R' has the meaning indicated for the compounds of the sub-formulae 1a-5a and is preferably alkyl, alkoxy or alkenyl.

Besides the preferred compounds of groups A, B and C, other compounds of the formulae 1, 2, 3, 4 and 5 with other variants of the proposed substituents are also customary. All these substances are obtainable by methods which are known from the literature or analogously thereto.

Besides compounds of the formula I according to the invention, the media according to the invention preferably comprise one or more compounds selected from group A and/or group B and/or group C. The proportions by weight of the compounds from these groups in the media according to the invention are preferably

| group A: | 0 to 90%, preferably 20 to 90%, in particular 30 to 90% |
| group B: | 0 to 80%, preferably 10 to 80%, in particular 10 to 65% |
| group C: | 0 to 80%, preferably 5 to 80%, in particular 5 to 50% | where the sum of the proportions by weight of the compounds from groups A, B and C present in the media according to the invention is preferably 5 to 90% and in particular 10 to 90%.

The media according to the invention preferably comprise 1 to 40%, particularly preferably 5 to 30%, of compounds according to the invention. Preference is furthermore given to media comprising more than 40%, in particular 45 to 90%, of compounds according to the invention. The media preferably comprise two, three or four compounds according to the invention.

The media according to the invention are prepared in a manner conventional per se. In general, the components are dissolved in one another, advantageously at elevated temperature. By means of suitable additives, the liquid-crystalline phases in accordance with the invention can be modified in such a way that they can be used in all types of liquid-crystal display element that have been disclosed to date. Additives of this type are known to the person skilled in the art and are described in detail in the literature (H. Kelker/R. Hatz, Handbook of Liquid Crystals, Verlag Chemie, Weinheim, 1980). Polymer-stabilised media are generally subsequently subjected to polymerisation after mixing of the components. Furthermore, stabilisers, antioxidants, dyes or nanoparticles can be added.

The mixtures according to the invention are suitable for TN, STN, ECB, IPS or TN-TFT applications and in particular for applications with media in the blue phase. Particular preference is given to use in polymer-stabilised blue phases. Suitable polymeric constituents of the blue phases are mesogenic and non-mesogenic monomers, in particular mono- and diacrylates, which are polymerised in the mixture in such a way that they maintain the desired molecular structure in a broad temperature range.

The construction of the matrix display according to the invention from polarisers, electrode base plates and surface-treated electrodes corresponds to the usual design for displays of this type. The term usual design is broadly drawn here and also encompasses all derivatives and modifications of the matrix display, in particular also matrix display elements based on poly-Si TFTs.

The following examples are intended to explain the invention without limiting it. Above and below, percentage data denote percent by weight. All temperatures are indicated in degrees Celsius. M.p. denotes melting point, cl.p.=clearing point. Furthermore, C=crystalline state, N=nematic phase, S=smectic phase and I=isotropic phase. The data between these symbols represent the transition temperatures. Δn denotes optical anisotropy (589 nm, 20° C.), and the flow viscosity $v_{20}$ (mm$^2$/sec) and the rotational viscosity $\gamma_1$ [mPa·s] are each determined at 20° C.

The physical, physicochemical and electro-optical parameters are determined by generally known methods, as described, inter alia, in the brochure "Merck Liquid Crystals—Licristal®—Physical Properties of Liquid Crystals—Description of the Measurement Methods", 1998, Merck KGaA, Darmstadt.

The dielectric anisotropy Δε of the individual substances is determined at 20° C. and 1 kHz. To this end, 5-10% by weight of the substance to be investigated are measured dissolved in the dielectrically positive mixture ZLI-4792 (Merck KGaA), and the measurement value is extrapolated to a concentration of 100%. The optical anisotropy Δn is determined at 20° C. and a wavelength of 589.3 nm, the rotational viscosity $\gamma_i$ at 20° C., both likewise by linear extrapolation.

The following abbreviations are used above and below:

RT room temperature

MTB ether methyl tert-butyl ether

THF tetrahydrofuran p-TsOH p-toluenesulfonic acid

DABCO 1,4-diazabicyclo[2.2.2]octane

Rf retention factor in chromatography

DIBAL-H diisobutylaluminium hydride

Pd (C) palladium on carbon (commercially available catalyst)

Example 1

6,6'-Difluoro-3'-propyl-3,4,3',4'-tetrahydro-2H,2'H-[3,7']bichromenyl-7-carbonitrile The synthesis of 7-bromo-6-fluoro-3-propylchroman is carried out in accordance with WO 2006/040009.

1.1. 6-Fluoro-7-iodo-3-propylchroman

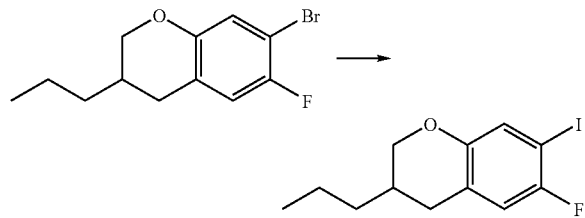

10.6 g (38.8 mmol) of 7-bromo-6-fluoro-3-propylchroman are initially introduced in 100 ml of THF, and 27 ml (43.0 mmol) of a 15 percent solution of n-butyllithium in hexane are added dropwise. After 90 min, 10.0 g (39.4 mmol) of iodine, dissolved in 50 ml of THF, are added, the mixture is stirred for 1 h, and the cooling is removed. The batch is diluted with MTB ether, washed with water and with sat. sodium hydrogensulfite soln. and dried over sodium sulfate. The solvent is removed in vacuo, and the crude product is filtered through silica gel with heptane/toluene (4:1), giving 6-fluoro-7-iodo-3-propylchroman as a colourless solid, which is sufficiently pure for further reaction.

1.2. Diethyl 2-(6-fluoro-3-propylchroman-7-yl)malonate

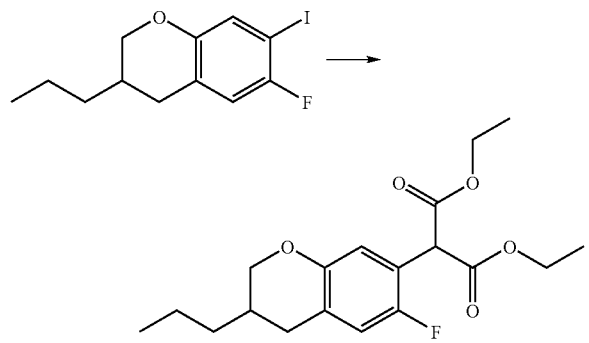

17.0 g (52.2 mmol) of anhydrous caesium carbonate, 700 mg (3.67 mmol) of copper(I) iodide and 700 mg (4.11 mmol) of o-phenylphenol are initially introduced under dry nitrogen, a solution of 11.4 g (33.5 mmol) of 6-fluoro-7-iodo-3-propylchroman and 16.0 g (100 mmol) of diethyl malonate in 150 ml of THF is added, and the mixture is heated under reflux overnight. MTB ether is subsequently added to the batch, which is washed with dil. hydrochloric acid and dried over sodium sulfate. The solvent is removed in vacuo, and the crude product is purified by chromatography on silica gel with heptane/ethyl acetate (4:1). The product fraction (Rf=0.55) is reacted without further purification.

1.3. 2-(6-Fluoro-3-propylchroman-7-yl)propane-1,3-diol

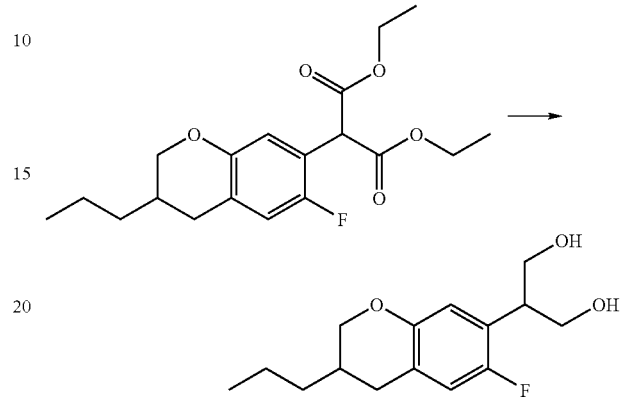

8.7 g (21.1 mmol) of the diethyl 2-(6-fluoro-3-propylchroman-7-yl)malonate obtained under 1.2. are initially introduced in 60 ml of toluene, and 106 ml (106 mmol) of a 1 M solution of diisobutylaluminium hydride in toluene are added dropwise at 5° C. The batch is subsequently added to ice-cold sat. ammonium chloride soln., acidified using dil. hydrochloric acid and extracted with MTB ether. The combined org. phases are dried over sodium sulfate and evaporated. Chromatography of the crude product on silica gel with MTB ether/heptane (4:1) gives 2-(6-fluoro-3-propylchroman-7-yl)propane-1,3-diol as a colourless solid.

$^{19}$F-NMR (377 MHz, CDCl$_3$)
δ=−129.0 ppm (dd, J=6.4 Hz, J=10.3 Hz, 1F, Ar—F).

1.4. 6-Fluoro-7-oxetan-3-yl-3-propylchroman

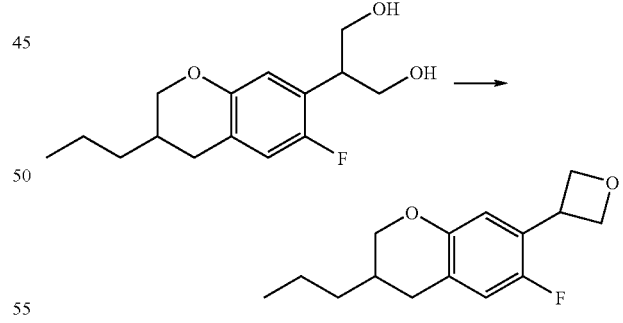

3.80 g (13.7 mmol) of 2-(6-fluoro-3-propylchroman-7-yl)propane-1,3-diol are dissolved in 70 ml of THF, and 8.7 ml (13.7 mmol) of a 15 percent solution of n-butyllithium in hexane are added at 0° C. After 30 min, 2.7 g (14.2 mmol) of p-toluenesulfonyl chloride in 30 ml of THF are added, and the mixture is stirred at RT for 1 h and re-cooled to 0° C. After addition of a further 8.7 ml (13.7 mmol) of a 15% solution of n-butyllithium in hexane, the cooling is removed, and the batch is heated under reflux for 4 h. The batch is subsequently diluted with MTB ether and washed with water. The org. phase is dried over sodium sulfate and evaporated, and the crude product is purified by chromatography on silica gel with heptane/ethyl acetate (3:2). The product fractions (Rf=0.5) are evaporated, and the product is used without further purification.

1.5. 3-(4-Bromo-2,5-difluorophenyl)-2-(6-fluoro-3-propylchroman-7-yl)propan-1-ol

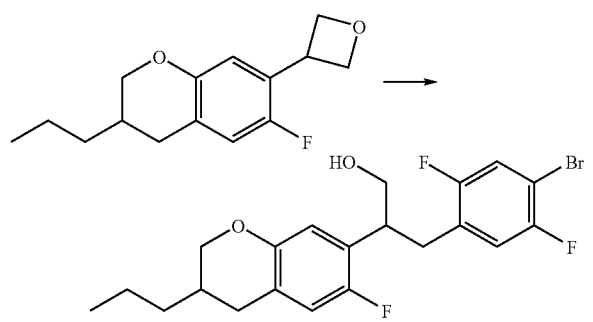

4.50 g (16.6 mmol) of 1,4-dibromo-2,6-difluorobenzene are dissolved in 70 ml of ether, and 11 ml (18 mmol) of a 15 percent solution of n-butyllithium in hexane are added at −70° C. After 30 min, a solution of 3.00 g (11.0 mmol) of 6-fluoro-7-oxetan-3-yl-3-propylchroman in 30 ml of ether is added dropwise, and, after 1 h, 1.5 ml (11.9 mmol) of boron trifluoride diethyl ether complex are carefully added. The batch is left to stir for 2 h at −78° C. and overnight at RT and hydrolysed using sat. ammonium chloride soln. The org. phase is separated off and washed with water and sat. sodium chloride soln. and dried over sodium sulfate. The solvent is removed in vacuo, and the residue is chromatographed on silica gel, firstly with toluene and then with toluene/ethyl acetate (2:1), giving 3-(4-bromo-2,5-difluorophenyl)-2-(6-fluoro-3-propylchroman-7-yl)propan-1-ol as a colourless solid.

1.6. 7-Bromo-6,6'-difluoro-3'-propyl-3,4,3',4'-tetrahydro-2H,2'H-[3,7]bichromenyl

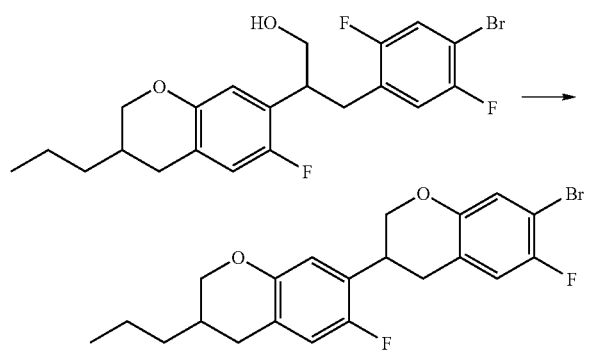

1.2 g (10.5 mmol) of potassium hydride (35 percent in paraffin oil) are initially introduced in 40 ml of THF, and a solution of 4.50 g (8.12 mmol) of 3-(4-bromo-2,5-difluorophenyl)-2-(6-fluoro-3-propylchroman-7-yl)propan-1-ol in 20 ml of THF is added dropwise at 30° C. The batch is subsequently stirred at 60° C. for 4 h, a little ethanol is added, and the batch is diluted with MTB ether and washed with sat. sodium chloride soln. The org. phase is dried over sodium sulfate, the solvent is removed in vacuo, and the crude product is filtered through silica gel with toluene and recrystallised from heptane/ethyl acetate, giving 7-bromo-6,6'-difluoro-3'-propyl-3,4,3',4'-tetrahydro-2H,2'H-[3,7']-bichromenyl as colourless crystals.

$^{19}$F-NMR (377 MHz, CDCl$_3$)

δ=−119.4 ppm (dd, J=6.2 Hz, J=8.5 Hz, 1F, Ar—F), −129.6 (ddd, J=6.5 Hz, J=6.5 Hz, J=10.4 Hz, 1F, Ar—F).

1.7. 6,6'-Difluoro-3'-propyl-3,4,3',4'-tetrahydro-2H,2'H-[3,7']-bichromenyl-7-carbonitrile

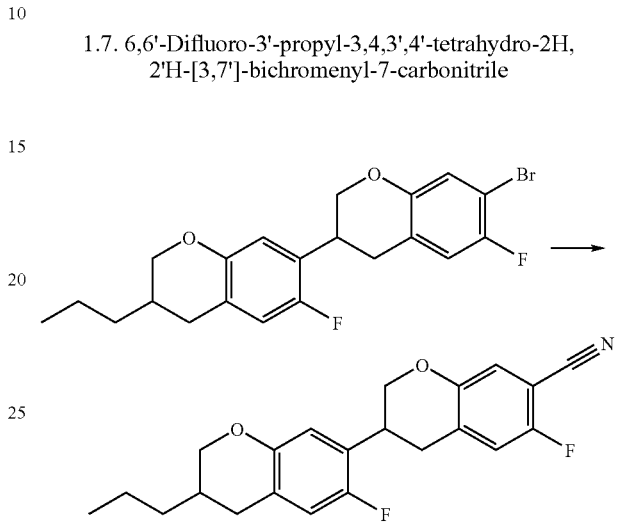

1.4 g (3.31 mmol) of 7-bromo-6,6'-difluoro-3'-propyl-3,4,3',4'-tetrahydro-2H,2'H-[3,7']bichromenyl are dissolved in 20 ml of THF, and 3 ml (4.8 mmol) of a 15 percent solution of n-butyl-lithium in hexane are added at −50° C. The batch is left to stir for 2 h at −70° C., and a solution of 0.9 g (5.00 mmol) of p-toluenesulfonyl cyanide in 10 ml of THF is subsequently added at such a rate that the temperature does not exceed −65° C. After 30 min, the batch is allowed to thaw, diluted with ether and washed with dil. hydrochloric acid. The org. phase is dried over sodium sulfate and evaporated, and the crude product is chromatographed on silica gel with heptane/toluene (2:3), giving 6,6'-difluoro-3'-propyl-3,4,3',4'-tetrahydro-2H,2'H-[3,7]bichromenyl-7-carbonitrile as colourless crystals of m.p. 122° C.

Phase behaviour: C 122 N (59) I

Example 2

(R)-6,8-difluoro-3-[5-((R)-6-fluoro-3-pentylchroman-7-yl)-1,3-dioxan-2-yl]chroman-7-carbonitrile

2.1. 2-(6-Fluoro-3-pentylchroman-7-yl)propane-1,3-diol

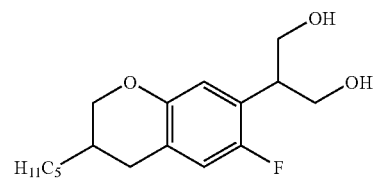

The preparation is carried out analogously to the synthesis of 2-(6-fluoro-3-propylchroman-7-yl)propane-1,3-diol described under 1.3.

2.2. 6,8-Difluoro-2H-chromene-3-carbaldehyde

2.2.1. 3,5-Difluorosalicylaldehyde

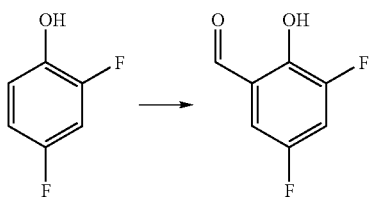

260 g (2.00 mol) of 2,4-difluorophenol are dissolved in 1.6 l of trifluoroacetic acid, and 560 g (4.00 mol) of hexamethylenetetramine are added in portions. After 30 min, the batch is warmed to 75° C. and stirred overnight. 2 l of 40 percent sulfuric acid are subsequently added at RT, the mixture is left to stir for 2.5 h, 1.5 l of ice-water are added, and the mixture is stirred for a further 30 min. The deposited precipitate is separated off, washed with water and taken up in dichloromethane. The resultant solution is dried over sodium sulfate and evaporated, giving 3,5-difluorosalicylaldehyde as a beige solid.

2.2.2. 6,8-Difluoro-2H-chromene-3-carbonitrile

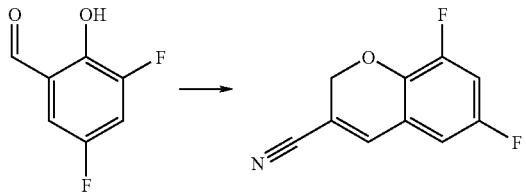

84 g (0.531 mol) of 3,5-difluorosalicylaldehyde are dissolved in 850 ml of acrylonitrile, 1 g (8 mmol) of p-methoxyphenol and 18 g (0.16 mol) of DABCO are added, and the mixture is heated overnight at 75° C. The batch is evaporated, the residue is taken up in dichloromethane, and the solution is filtered through silica gel, giving 6,8-difluoro-2H-chromene-3-carbonitrile, which is sufficiently pure for further reactions.

2.2.3. 6,8-Difluoro-2H-chromene-3-carbaldehyde

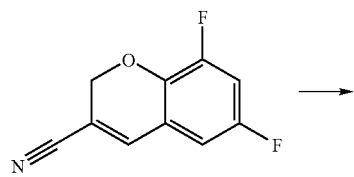

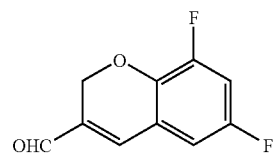

47.0 g (243 mmol) of 6,8-difluoro-2H-chromene-3-carbonitrile are dissolved in 300 ml of toluene, and 260 ml (260 mmol) of a 1 M solution of diisobutylaluminium hydride in toluene are added at −20° C. After 1 h, the batch is allowed to thaw, the solution is added to ice-cold dil. hydrochloric acid, and the mixture is left to stir vigorously for 2 h. The aqueous phase is separated off and extracted with MTB ether. The combined org. phases are washed with water, dried over sodium sulfate and evaporated, giving 6,8-difluoro-2H-chromene-3-carbaldehyde having a content of 99.0% (GC).

2.3. 6,8-Difluoro-3-[5-(6-fluoro-3-pentylchroman-7-yl)-1,3-dioxan-2-yl]-2H-chromene

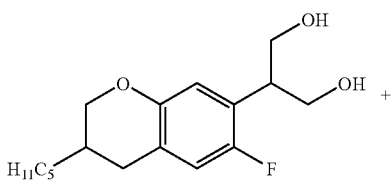

1.30 g (4.39 mmol) of 2-(6-fluoro-3-pentylchroman-7-yl)propane-1,3-diol and 900 mg (4.59 mmol) of 6,8-difluoro-2H-chromene-3-carbaldehyde are dissolved in 50 ml of dichloromethane and heated under reflux on a water separator for 5 h in the presence of 50 mg of p-toluenesulfonic acid. The solution is subsequently washed with sat. sodium hydrogencarbonate soln. and dried over sodium sulfate. The solvent is removed in vacuo, and the residue is recrystallised from heptane/toluene, giving 6,8-difluoro-3-[5-(6-fluoro-3-pentylchroman-7-yl)-1,3-dioxan-2-yl]-2H-chromene (trans:cis=80:20) as a colourless solid.

2.4. (R)-6,8-difluoro-3-[5-((R)-6-fluoro-3-pentyl-chroman-7-yl)-1,3-dioxan-2-yl]chroman

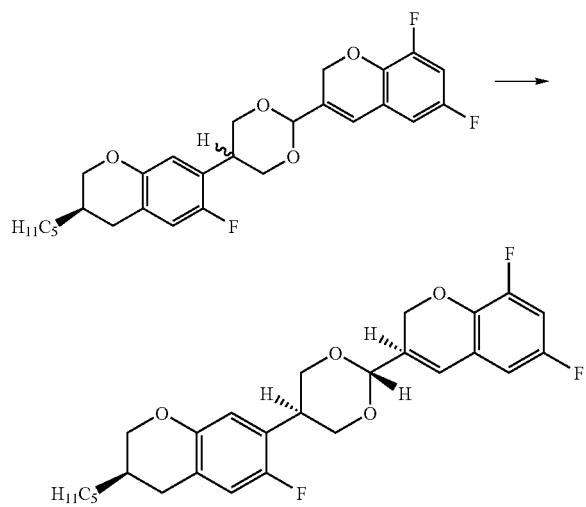

6,8-Difluoro-3-[5-(6-fluoro-3-pentylchroman-7-yl)-1,3-dioxan-2-yl]-2H-chromene is hydrogenated to completion in THF on a palladium/active carbon catalyst. The solution is filtered and evaporated, and the residue is recrystallised from heptane, giving isomerically pure (R)-6,8-difluoro-3-[5-((R)-6-fluoro-3-pentylchroman-7-yl)-1,3-dioxan-2-yl]chroman as a colourless solid.

$^{19}$F-NMR (377 MHz, CDCl$_3$)

δ=−121.8 ppm (t, J=8.6 Hz, 1F, Ar—F), −128.4 (ddd, J=6.4 Hz, J=10.4 Hz, 1F, Ar—F), −133.1 (dd, J=1.5 Hz, J=10.8 Hz, 1F, Ar—F).

2.5. (R)-6,8-difluoro-3-[5-((R)-6-fluoro-3-pentyl-chroman-7-yl)-1,3-dioxan-2-yl]chroman-7-carbonitrile

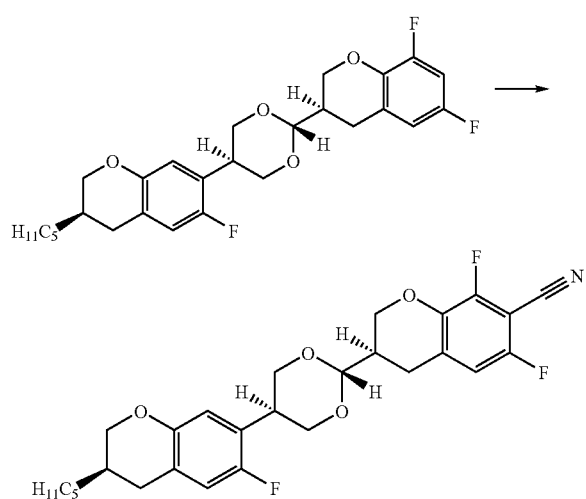

800 mg (1.68 mmol) of (R)-6,8-difluoro-3-[5-((R)-6-fluoro-3-pentylchroman-7-yl)-1,3-dioxan-2-yl]chroman are dissolved in 30 ml of THF, and 1.7 ml (2.38 mmol) of a 1.4 M solution of s-butyllithium in cyclohexane are added at −50° C. The batch is warmed at −25° C. for 5 min, left to stir at −70° C. for 2 h, and a solution of 400 mg (2.21 mmol) of p-toluenesulfonyl cyanide in 10 ml of THF is subsequently added at such a rate that the temperature does not exceed −65° C. After 1 h, the batch is allowed to thaw, diluted with ether and washed with dil. hydrochloric acid. The org. phase is dried over sodium sulfate and evaporated, and the crude product is chromatographed on silica gel with toluene, giving (R)-6,8-difluoro-3-[5-((R)-6-fluoro-3-pentylchroman-7-yl)-1,3-dioxan-2-yl]chroman-7-carbonitrile as colourless crystals of m.p. 111° C.

Phase behaviour: Tg 6 C 111 N 145 I
Δε 83
Δn 0.140

Example 3

6,8-Difluoro-3-[5-(6-fluoro-3-pentylchroman-7-yl)-1,3-dioxan-2-yl]-7-trifluoromethoxychroman

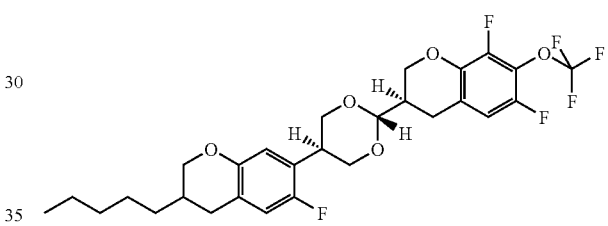

The synthesis described under Example 2 gives 6,8-difluoro-3-[5-(6-fluoro-3-pentylchroman-7-yl)-1,3-dioxan-2-yl]-7-trifluoromethoxychroman as a colourless solid.

Phase behaviour: Tg −22 C 88 SmA 175 N (174.8) I
$^{19}$F-NMR (377 MHz, CDCl$_3$)
δ=−59.79 ppm (t, J=7.0 Hz, 3F, —OCF$_3$), 128.4 (dd, J=6.4 Hz, J=10.3 Hz, 1F, Ar—F), 137.2 (m$_c$, 1F, Ar—F), 146.8 (m$_c$, 1F, Ar—F).
Δn 0.102

Example 4

7-Cyano-6,8-difluoro-3-[2-(6-fluoro-3-pentylchroman-7-yl)ethyl]-2H-chromene 4.1 6-Fluoro-3-pentylchroman-7-carbaldehyde

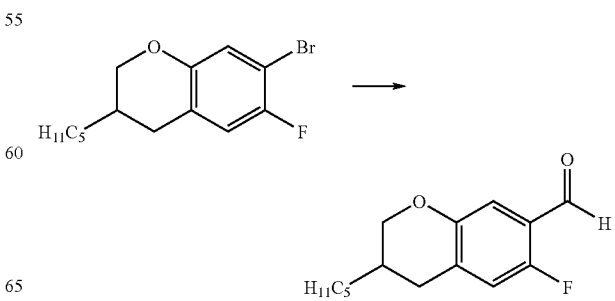

15.5 g (51.5 mmol) of 7-bromo-6-fluoro-3-pentylchroman are dissolved in 85 ml of THF, and 35 ml (55.7 mmol) of a 15 percent solution of n-butyllithium in n-hexane are slowly added at −70° C. After 1 h, 6.3 ml (56.7 mmol) of N-formylpiperidine in 15 ml of THF are added dropwise, and the mixture is stirred for 1 h. The batch is subsequently allowed to thaw, added to water, acidified using dil. hydrochloric acid and extracted three times with MTB ether. The combined org. phases are washed with water and sat. sodium chloride soln. and dried over sodium sulfate, the solvent is removed in vacuo, and the residue is recrystallised from heptane at −25° C., giving 6-fluoro-3-pentylchroman-7-carbaldehyde as colourless crystals (Rf=0.4; 1-chlorobutane).

4.2 (6-Fluoro-3-pentylchroman-7-yl)methanol

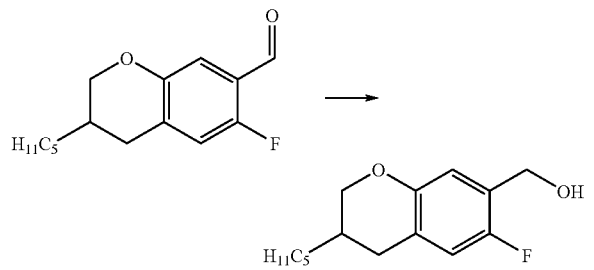

11.1 g (44.3 mmol) of 6-fluoro-3-pentylchroman-7-carbaldehyde are dissolved in 100 ml of ethanol, and 2.0 g (52.8 mmol) of sodium borohydride are added in portions. After 3 h, the batch is diluted with water and extracted three times with MTB ether. The combined org. phases are washed with sat. sodium chloride soln. and dried over sodium sulfate, the solvent is removed in vacuo, and the residue is filtered through silica gel with dichloromethane (Rf=0.3), giving (6-fluoro-3-pentylchroman-7-yl)methanol as a colourless solid.

4.3 7-Bromomethyl-6-fluoro-3-pentylchroman

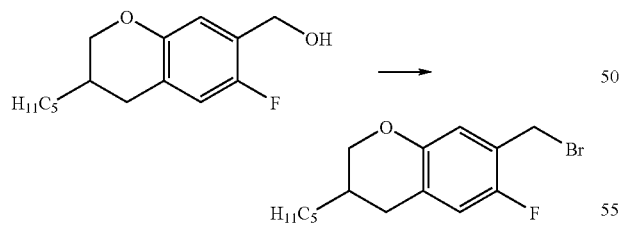

10.2 g (38.9 mmol) of triphenylphosphine are suspended in 80 ml of acetonitrile, and 2.0 ml (39.0 mmol) of bromine are added dropwise with ice cooling. A solution of 10.0 g (38.4 mmol) of (6-fluoro-3-pentylchroman-7-yl)methanol in 20 ml of acetonitrile is subsequently added, and the mixture is stirred overnight at room temp. After addition of water, the mixture is extracted three times with n-heptane, and the combined org. phases are washed with water and dried over sodium sulfate. The solvent is removed in vacuo, and the residue is filtered through silica gel with heptane/toluene (4:1), giving 7-bromomethyl-6-fluoro-3-pentylchroman as a colourless oil.

$^{19}$F-NMR (377 MHz, CDCl$_3$)

δ=−128.7 ppm (dd, J=6.7 Hz, J=9.7 Hz, 1F).

4.4 (6-Fluoro-3-pentylchroman-7-ylmethyl)triphenylphosphonium bromide

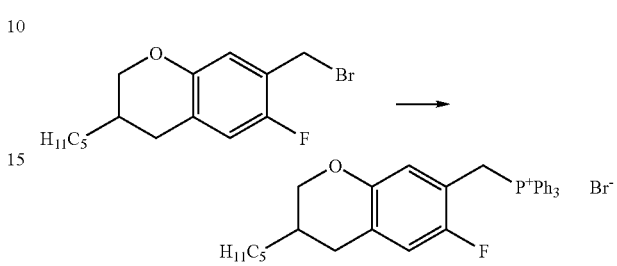

11.0 g (34.9 mmol) of 7-bromomethyl-6-fluoro-3-pentylchroman and 9.20 g (35.1 mmol) of triphenylphosphine are dissolved in 70 ml of acetonitrile, and the mixture is stirred overnight at room temp. The batch is subsequently cooled to 0° C., and the precipitated (6-fluoro-3-pentylchroman-7-ylmethyl)triphenylphosphonium bromide is filtered off with suction and dried in vacuo.

4.5 6,8-Difluoro-3-[2-(6-fluoro-3-pentylchroman-7-yl)vinyl]-2H-chromene

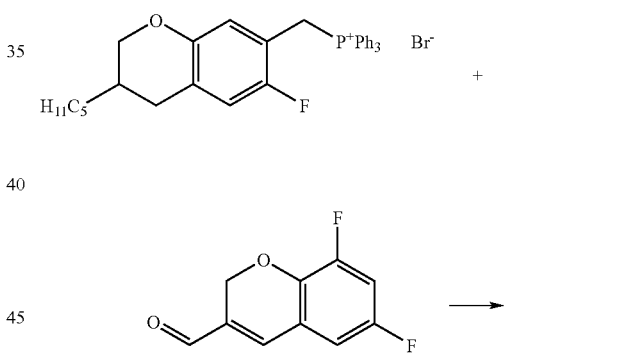

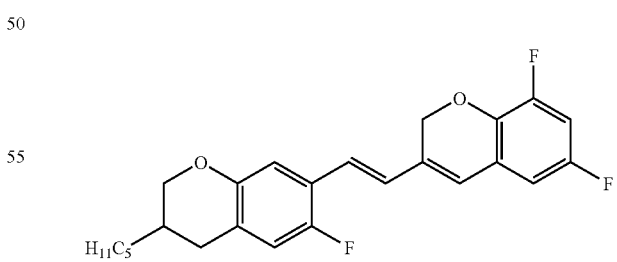

10.2 g (17.7 mmol) of (6-fluoro-3-pentylchroman-7-ylmethyl)triphenylphosphonium bromide are dissolved in 50 ml of THF, and 2.0 g (17.8 mmol) of potassium tert-butoxide are added with ice cooling. After 1 h, a solution of 6,8-difluoro-2H-chromene-3-carbaldehyde in 50 ml of THF is slowly added dropwise, and the batch is left to stir overnight at room temp. The solution is subsequently added to water, acidified using dil. hydrochloric acid and extracted three times with MTB ether. The combined org. phases are washed with sat. sodium chloride soln. and dried over sodium sulfate. The solvent is removed in vacuo, and the residue is chromatographed on silica gel with heptane/toluene (1:1) and recrystallised from heptane at −20° C., giving 6,8-difluoro-3-[2-(6-fluoro-3-pentylchroman-7-yl)vinyl]-2H-chromene as yellow crystals.

$^{19}$F-NMR (377 MHz, CDCl$_3$)

δ=−120.3 ppm (dt, J=2.1 Hz, J=8.3 Hz, 1F), −128.8 (dd, J=6.5 Hz, J=10.7 Hz, 1F), −133.9 (m$_c$, therein: d, J=10.3 Hz, 1F).

4.6 6,8-Difluoro-3-[2-(6-fluoro-3-pentylchroman-7-yl)ethyl]-2H-chromene

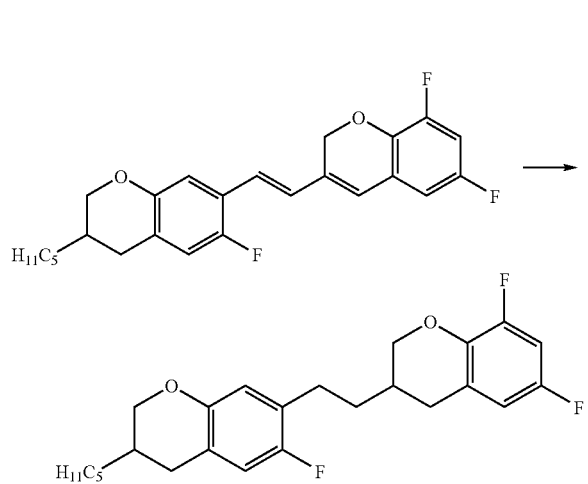

6,8-Difluoro-3-[2-(6-fluoro-3-pentylchroman-7-yl)vinyl]-2H-chromene is dissolved in THF and hydrogenated to completion on a palladium/active carbon catalyst. The catalyst is filtered off, the solution is evaporated, the residue is filtered through silica gel with toluene/heptane (3:2), and the crude product is recrystallised from n-heptane at −25° C., giving colourless crystals of m.p. 84° C.

4.7 7-Cyano-6,8-difluoro-3-[2-(6-fluoro-3-pentylchroman-7-yl)ethyl]-2H-chromene

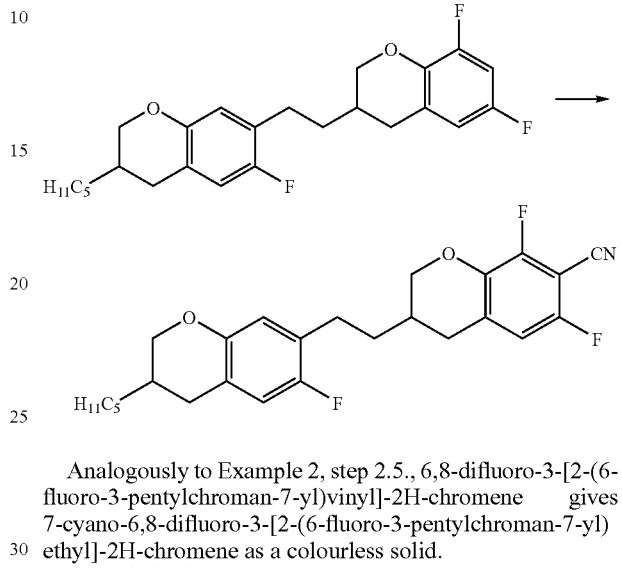

Analogously to Example 2, step 2.5., 6,8-difluoro-3-[2-(6-fluoro-3-pentylchroman-7-yl)vinyl]-2H-chromene gives 7-cyano-6,8-difluoro-3-[2-(6-fluoro-3-pentylchroman-7-yl)ethyl]-2H-chromene as a colourless solid.

Phase behaviour: C 70 Sm (17) I.

Δε 53

Δn 0.119

The following compounds are prepared analogously to Examples 1-4

$R^1$-$A^1$-$W^1$-$A^2$-$W^2$—$Z^4$-$A^3$-$R^2$ where the substituents adopt the meanings as shown in the table.

TABLE

Further example compounds

| | R¹ | A¹ | W¹ | A² | W² | Z⁴ | A³ | R² |
|---|---|---|---|---|---|---|---|---|
| 1 | C₃H₇— | | chroman | | chroman | | | F |
| 2 | C₃H₇— | | chroman | | chroman | | | CF₃ |
| 3 | C₃H₇— | | chroman | | chroman | | | OCF₃ |
| 4 | C₃H₇— | | chroman | | chroman | | | CN |
| 5 | C₅H₁₁— | | chroman | | chroman | | | F |
| 6 | C₅H₁₁— | | chroman | | chroman | | | CF₃ |
| 7 | C₅H₁₁— | | chroman | | chroman | | | OCF₃ |
| 8 | C₅H₁₁— | | chroman | | chroman | | | CN |

TABLE-continued

Further example compounds

| | $R^1$ | $A^1$ | $W^1$ | $A^2$ | $W^2$ | $Z^4$ | $A^3$ | $R^2$ |
|---|---|---|---|---|---|---|---|---|
| 9 | isobutenyl | | 3-methylchroman | | 3-methylchroman | | | F |
| 10 | isobutenyl | | 3-methylchroman | | 3-methylchroman | | | $CF_3$ |
| 11 | isobutenyl | | 3-methylchroman | | 3-methylchroman | | | $OCF_3$ |
| 12 | isobutenyl | | 3-methylchroman | | 3-methylchroman | | | CN |
| 13 | $C_3H_7$ | | 3-methylchroman | | 6-fluoro-3-methylchroman | | | F |
| 14 | $C_3H_7$ | | 3-methylchroman | | 6-fluoro-3-methylchroman | | | $CF_3$ |
| 15 | $C_3H_7$ | | 3-methylchroman | | 6-fluoro-3-methylchroman | | | $OCF_3$ |

TABLE-continued

Further example compounds

| | $R^1$ | $A^1$ | $W^1$ | $A^2$ | $W^2$ | $Z^4$ | $A^3$ | $R^2$ |
|---|---|---|---|---|---|---|---|---|
| 16 | $C_3H_7$ | | chroman-3-methyl | | 6-F-chroman-3-methyl | | | CN |
| 17 | $C_5H_{11}$ | | chroman-3-methyl | | 6-F-chroman-3-methyl | | | F |
| 18 | $C_5H_{11}$ | | chroman-3-methyl | | 6-F-chroman-3-methyl | | | $CF_3$ |
| 19 | $C_5H_{11}$ | | chroman-3-methyl | | 6-F-chroman-3-methyl | | | $OCF_3$ |
| 20 | $C_5H_{11}$ | | chroman-3-methyl | | 6-F-chroman-3-methyl | | | CN |
| 21 | CH=CH-propenyl | | chroman-3-methyl | | 6-F-chroman-3-methyl | | | F |
| 22 | CH=CH-propenyl | | chroman-3-methyl | | 6-F-chroman-3-methyl | | | $CF_3$ |

TABLE-continued

Further example compounds

| | $R^1$ | $A^1$ | $W^1$ | $A^2$ | $W^2$ | $Z^4$ | $A^3$ | $R^2$ |
|---|---|---|---|---|---|---|---|---|
| 23 | CH₂=CH– | | 3-methylchroman | | 6-F,7-methylchroman | | | $OCF_3$ |
| 24 | CH₂=CH– | | 3-methylchroman | | 6-F,7-methylchroman | | | CN |
| 25 | $C_3H_7$ | | 3-methylchroman | | 6-F,7-methyl,8-F chroman | | | F |
| 26 | $C_3H_7$ | | 3-methylchroman | | 6-F,7-methyl,8-F chroman | | | $CF_3$ |
| 27 | $C_3H_7$ | | 3-methylchroman | | 6-F,7-methyl,8-F chroman | | | $OCF_3$ |
| 28 | $C_3H_7$ | | 3-methylchroman | | 6-F,7-methyl,8-F chroman | | | CN |

TABLE-continued

Further example compounds

| | R¹ | A¹ | W¹ | A² | W² | Z⁴ | A³ | R² |
|---|---|---|---|---|---|---|---|---|
| 29 | C₅H₁₁— | | 3-methylchroman (7-Me) | | 3-methylchroman (6-F, 8-F) | | | F |
| 30 | C₅H₁₁— | | 3-methylchroman (7-Me) | | 3-methylchroman (6-F, 8-F) | | | CF₃ |
| 31 | C₅H₁₁— | | 3-methylchroman (7-Me) | | 3-methylchroman (6-F, 8-F) | | | OCF₃ |
| 32 | C₅H₁₁— | | 3-methylchroman (7-Me) | | 3-methylchroman (6-F, 8-F) | | | CN |
| 33 | CH₃-CH=CH- | | 3-methylchroman (7-Me) | | 3-methylchroman (6-F, 8-F) | | | F |
| 34 | CH₃-CH=CH- | | 3-methylchroman (7-Me) | | 3-methylchroman (6-F, 8-F) | | | CF₃ |

TABLE-continued

Further example compounds

| | $R^1$ | $A^1$ | $W^1$ | $A^2$ | $W^2$ | $Z^4$ | $A^3$ | $R^2$ |
|---|---|---|---|---|---|---|---|---|
| 35 | CH$_2$=CH— | | 3-methylchroman-6,(7-methyl) | | 3-methyl-6,8-difluoro-7-methylchroman | | | OCF$_3$ |
| 36 | CH$_2$=CH— | | 3-methylchroman-(7-methyl) | | 3-methyl-6,8-difluoro-7-methylchroman | | | CN |
| 37 | C$_3$H$_7$— | | 3-methyl-6-fluoro-7-methylchroman | | 3-methyl-7-methylchroman | | | F |
| 38 | C$_3$H$_7$— | | 3-methyl-6-fluoro-7-methylchroman | | 3-methyl-7-methylchroman | | | CF$_3$ |
| 39 | C$_3$H$_7$— | | 3-methyl-6-fluoro-7-methylchroman | | 3-methyl-7-methylchroman | | | OCF$_3$ |
| 40 | C$_3$H$_7$— | | 3-methyl-6-fluoro-7-methylchroman | | 3-methyl-7-methylchroman | | | CN |
| 41 | C$_5$H$_{11}$— | | 3-methyl-6-fluoro-7-methylchroman | | 3-methyl-7-methylchroman | | | F |

TABLE-continued

Further example compounds

| | R¹ | A¹ | W¹ | A² | W² | Z⁴ | A³ | R² |
|---|---|---|---|---|---|---|---|---|
| 42 | C₅H₁₁— | | 3-methyl-6-fluorochroman | | 7-methyl-chroman | | | CF₃ |
| 43 | C₅H₁₁— | | 3-methyl-6-fluorochroman | | 7-methyl-chroman | | | OCF₃ |
| 44 | C₅H₁₁— | | 3-methyl-6-fluorochroman | | 7-methyl-chroman | | | CN |
| 45 | CH₂=CH– | | 3-methyl-6-fluorochroman | | 7-methyl-chroman | | | F |
| 46 | CH₂=CH– | | 3-methyl-6-fluorochroman | | 7-methyl-chroman | | | CF₃ |
| 47 | CH₂=CH– | | 3-methyl-6-fluorochroman | | 7-methyl-chroman | | | OCF₃ |
| 48 | CH₂=CH– | | 3-methyl-6-fluorochroman | | 7-methyl-chroman | | | CN |

TABLE-continued

Further example compounds

| | $R^1$ | $A^1$ | $W^1$ | $A^2$ | $W^2$ | $Z^4$ | $A^3$ | $R^2$ |
|---|---|---|---|---|---|---|---|---|
| 49 | $C_3H_7$— | | chromane-F | | chromane-F | | | F |
| 50 | $C_3H_7$— | | chromane-F | | chromane-F | | | $CF_3$ |
| 51 | $C_3H_7$— | | chromane-F | | chromane-F | | | $OCF_3$ |
| 52 | $C_3H_7$— | | chromane-F | | chromane-F | | | CN |
| 53 | $C_5H_{11}$— | | chromane-F | | chromane-F | | | F |
| 54 | $C_5H_{11}$— | | chromane-F | | chromane-F | | | $CF_3$ |
| 55 | $C_5H_{11}$— | | chromane-F | | chromane-F | | | $OCF_3$ |
| 56 | $C_5H_{11}$— | | chromane-F | | chromane-F | | | CN |

TABLE-continued

Further example compounds

| | $R^1$ | $A^1$ | $W^1$ | $A^2$ | $W^2$ | $Z^4$ | $A^3$ | $R^2$ |
|---|---|---|---|---|---|---|---|---|
| 57 | CH₂=C(CH₃)– | | chromanyl-F,CH₃ | | chromanyl-F,CH₃ | | | F |
| 58 | CH₂=C(CH₃)– | | chromanyl-F,CH₃ | | chromanyl-F,CH₃ | | | CF₃ |
| 59 | CH₂=C(CH₃)– | | chromanyl-F,CH₃ | | chromanyl-F,CH₃ | | | OCF₃ |
| 60 | CH₂=C(CH₃)– | | chromanyl-F,CH₃ | | chromanyl-F,CH₃ | | | CN |
| 61 | C₃H₇– | | chromanyl-F,CH₃ | | chromanyl-F,F,CH₃ | | | F |
| 62 | C₃H₇– | | chromanyl-F,CH₃ | | chromanyl-F,F,CH₃ | | | CF₃ |

TABLE-continued
Further example compounds

| | $R^1$ | $A^1$ | $W^1$ | $A^2$ | $W^2$ | $Z^4$ | $A^3$ | $R^2$ |
|---|---|---|---|---|---|---|---|---|
| 63 | $C_3H_7$— | | chroman-F,F,Me | | chroman-F,F,Me | | | $OCF_3$ |
| 64 | $C_3H_7$— | | chroman-F,F,Me | | chroman-F,F,Me | | | CN |
| 65 | $C_5H_{11}$— | | chroman-F,F,Me | | chroman-F,F,Me | | | F |
| 66 | $C_5H_{11}$— | | chroman-F,F,Me | | chroman-F,F,Me | | | $CF_3$ |
| 67 | $C_5H_{11}$— | | chroman-F,F,Me | | chroman-F,F,Me | | | $OCF_3$ |
| 68 | $C_5H_{11}$— | | chroman-F,F,Me | | chroman-F,F,Me | | | CN |

TABLE-continued

Further example compounds

| | R¹ | A¹ | W¹ | A² | W² | Z⁴ | A³ | R² |
|---|---|---|---|---|---|---|---|---|
| 69 | CH₂=C(CH₃)– | | 6-F,7-Me-chromanyl(3-Me) | | 6-F,7-Me,8-F-chromanyl(3-Me) | | | F |
| 70 | CH₂=C(CH₃)– | | 6-F,7-Me-chromanyl(3-Me) | | 6-F,7-Me,8-F-chromanyl(3-Me) | | | CF₃ |
| 71 | CH₂=C(CH₃)– | | 6-F,7-Me-chromanyl(3-Me) | | 6-F,7-Me,8-F-chromanyl(3-Me) | | | OCF₃ |
| 72 | CH₂=C(CH₃)– | | 6-F,7-Me-chromanyl(3-Me) | | 6-F,7-Me,8-F-chromanyl(3-Me) | | | CN |
| 73 | C₃H₇– | | 6-F,7-Me,8-F-chromanyl(3-Me) | | 6-F,7-Me,8-F-chromanyl(3-Me) | | | F |
| 74 | C₃H₇– | | 6-F,7-Me,8-F-chromanyl(3-Me) | | 6-F,7-Me,8-F-chromanyl(3-Me) | | | CF₃ |

TABLE-continued

Further example compounds

| | R¹ | A¹ | W¹ | A² | W² | Z⁴ | A³ | R² |
|---|---|---|---|---|---|---|---|---|
| 75 | $C_3H_7$— | | 3-methylchroman-6,8-diF | | 3-methylchroman-6,8-diF | | | $OCF_3$ |
| 76 | $C_3H_7$— | | 3-methylchroman-6,8-diF | | 3-methylchroman-6,8-diF | | | CN |
| 77 | $C_5H_{11}$— | | 3-methylchroman-6,8-diF | | 3-methylchroman-6,8-diF | | | F |
| 78 | $C_5H_{11}$— | | 3-methylchroman-6,8-diF | | 3-methylchroman-6,8-diF | | | $CF_3$ |
| 79 | $C_5H_{11}$— | | 3-methylchroman-6,8-diF | | 3-methylchroman-6,8-diF | | | $OCF_3$ |
| 80 | $C_5H_{11}$— | | 3-methylchroman-6,8-diF | | 3-methylchroman-6,8-diF | | | CN |

TABLE-continued

Further example compounds

| | R¹ | A¹ | W¹ | A² | W² | Z⁴ | A³ | R² |
|---|---|---|---|---|---|---|---|---|
| 81 | CH=CH₂ (isopropenyl) | | 5,8-difluoro-3-methylchroman | | 6,8-difluoro-3-methylchroman | | | F |
| 82 | CH=CH₂ | | 5,8-difluoro-3-methylchroman | | 6,8-difluoro-3-methylchroman | | | CF₃ |
| 83 | CH=CH₂ | | 5,8-difluoro-3-methylchroman | | 6,8-difluoro-3-methylchroman | | | OCF₃ |
| 84 | CH=CH₂ | | 5,8-difluoro-3-methylchroman | | 6,8-difluoro-3-methylchroman | | | CN |
| 85 | C₃H₇ | | 3-methylchroman | 5-methyl-1,3-dioxane | 3-methylchroman | | | F |
| 86 | C₃H₇ | | 3-methylchroman | 5-methyl-1,3-dioxane | 3-methylchroman | | | CF₃ |
| 87 | C₃H₇ | | 3-methylchroman | 5-methyl-1,3-dioxane | 3-methylchroman | | | OCF₃ |

TABLE-continued
Further example compounds
| | R¹ | A¹ | A² | W² | Z⁴ | A³ | R² |
|---|---|---|---|---|---|---|---|
| 88 | C₃H₇ |  |  |  | | | CN |
| 89 | C₅H₁₁ |  |  |  | | | F |
| 90 | C₅H₁₁ |  | 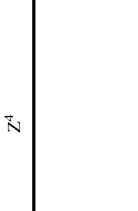 |  | | | CF₃ |
| 91 | C₅H₁₁ |  |  |  | | | OCF₃ |
| 92 | C₅H₁₁ |  |  | 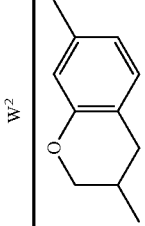 | | | CN |
| 93 | 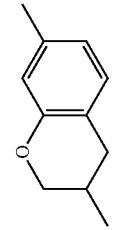 | 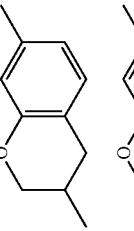 | 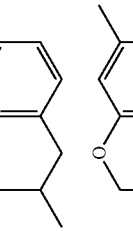 | 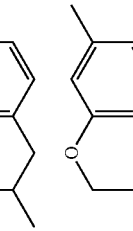 | | | F |
| 94 | 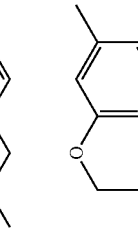 | 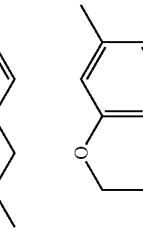 | 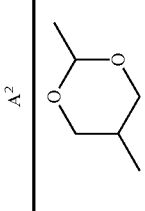 | 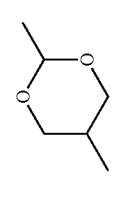 | | | CF₃ |
| 95 | 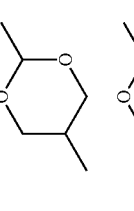 | 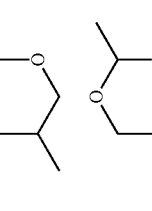 | 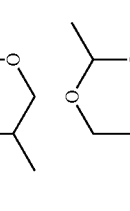 | 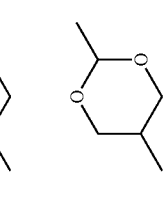 | | | OCF₃ |

TABLE-continued

Further example compounds

| | R¹ | A¹ | W¹ | A² | W² | Z⁴ | A³ | R² |
|---|---|---|---|---|---|---|---|---|
| 96 | CH₂=C(CH₃)– | | 3-methylchroman | 2-methyl-5-methyl-1,3-dioxane | 7-methylchroman | | | CN |
| 97 | C₃H₇ | | 3-methylchroman | 2-methyl-5-methyl-1,3-dioxane | 6-fluoro-3-methylchroman | | | F |
| 98 | C₃H₇ | | 3-methylchroman | 2-methyl-5-methyl-1,3-dioxane | 6-fluoro-3-methylchroman | | | CF₃ |
| 99 | C₃H₇ | | 3-methylchroman | 2-methyl-5-methyl-1,3-dioxane | 6-fluoro-3-methylchroman | | | OCF₃ |
| 100 | C₃H₇ | | 3-methylchroman | 2-methyl-5-methyl-1,3-dioxane | 6-fluoro-3-methylchroman | | | CN |
| 101 | C₅H₁₁ | | 3-methylchroman | 2-methyl-5-methyl-1,3-dioxane | 6-fluoro-3-methylchroman | | | F |
| 102 | C₅H₁₁ | | 3-methylchroman | 2-methyl-5-methyl-1,3-dioxane | 6-fluoro-3-methylchroman | | | CF₃ |
| 103 | C₅H₁₁ | | 3-methylchroman | 2-methyl-5-methyl-1,3-dioxane | 6-fluoro-3-methylchroman | | | OCF₃ |

TABLE-continued

Further example compounds

| R¹ | A¹ | W¹ | A² | W² | Z⁴ | A³ | R² |
|---|---|---|---|---|---|---|---|
| 104 C₅H₁₁— | | chromane-3-methyl | 2-methyl-5-methyl-1,3-dioxane | 6-fluoro-8-methyl-chromane-3-methyl | | | CN |
| 105 isobutenyl | | chromane-3-methyl | 2-methyl-5-methyl-1,3-dioxane | 6-fluoro-8-methyl-chromane-3-methyl | | | F |
| 106 isobutenyl | | chromane-3-methyl | 2-methyl-5-methyl-1,3-dioxane | 6-fluoro-8-methyl-chromane-3-methyl | | | CF₃ |
| 107 isobutenyl | | chromane-3-methyl | 2-methyl-5-methyl-1,3-dioxane | 6-fluoro-8-methyl-chromane-3-methyl | | | OCF₃ |
| 108 isobutenyl | | chromane-3-methyl | 2-methyl-5-methyl-1,3-dioxane | 6-fluoro-8-methyl-chromane-3-methyl | | | CN |
| 109 C₃H₇— | | chromane-3-methyl | 2-methyl-5-methyl-1,3-dioxane | 6,8-difluoro-7-methyl-chromane-3-methyl | | | F |

TABLE-continued

Further example compounds

| | $R^1$ | $A^1$ | $W^1$ | $A^2$ | $W^2$ | $Z^4$ | $A^3$ | $R^2$ |
|---|---|---|---|---|---|---|---|---|
| 110 | $C_3H_7$ | | 3-methylchroman | 2,5-dimethyl-1,3-dioxane | 6,8-difluoro-3-methylchroman | | | $CF_3$ |
| 111 | $C_3H_7$ | | 3-methylchroman | 2,5-dimethyl-1,3-dioxane | 6,8-difluoro-3-methylchroman | | | $OCF_3$ |
| 112 | $C_3H_7$ | | 3-methylchroman | 2,5-dimethyl-1,3-dioxane | 6,8-difluoro-3-methylchroman | | | $CN$ |
| 113 | $C_5H_{11}$ | | 3-methylchroman | 2,5-dimethyl-1,3-dioxane | 6,8-difluoro-3-methylchroman | | | $F$ |
| 114 | $C_5H_{11}$ | | 3-methylchroman | 2,5-dimethyl-1,3-dioxane | 6,8-difluoro-3-methylchroman | | | $CF_3$ |
| 115 | $C_5H_{11}$ | | 3-methylchroman | 2,5-dimethyl-1,3-dioxane | 6,8-difluoro-3-methylchroman | | | $OCF_3$ |

TABLE-continued

Further example compounds

| | R¹ | A¹ | W¹ | A² | W² | Z⁴ | A³ | R² |
|---|---|---|---|---|---|---|---|---|
| 116 | C₅H₁₁— | | (3-methylchroman) | (2,5-dimethyl-1,3-dioxane) | (6,8-difluoro-3-methylchroman) | | | CN |
| 117 | CH₂=C(CH₃)— | | (3-methylchroman) | (2,5-dimethyl-1,3-dioxane) | (6,8-difluoro-3-methylchroman) | | | F |
| 118 | CH₂=C(CH₃)— | | (3-methylchroman) | (2,5-dimethyl-1,3-dioxane) | (6,8-difluoro-3-methylchroman) | | | CF₃ |
| 119 | CH₂=C(CH₃)— | | (3-methylchroman) | (2,5-dimethyl-1,3-dioxane) | (6,8-difluoro-3-methylchroman) | | | OCF₃ |
| 120 | CH₂=C(CH₃)— | | (3-methylchroman) | (2,5-dimethyl-1,3-dioxane) | (6,8-difluoro-3-methylchroman) | | | CN |
| 121 | C₃H₇— | | (6-fluoro-3-methylchroman) | (2,5-dimethyl-1,3-dioxane) | (3-methylchroman) | | | F |

TABLE-continued

Further example compounds

| | R¹ | A¹ | W¹ | A² | W² | Z⁴ | A³ | R² |
|---|---|---|---|---|---|---|---|---|
| 122 | C₃H₇ | | chromane-F | dioxane | chromane | | | CF₃ |
| 123 | C₃H₇ | | chromane-F | dioxane | chromane | | | OCF₃ |
| 124 | C₃H₇ | | chromane-F | dioxane | chromane | | | CN |
| 125 | C₅H₁₁ | | chromane-F | dioxane | chromane | | | F |
| 126 | C₅H₁₁ | | chromane-F | dioxane | chromane | | | CF₃ |
| 127 | C₅H₁₁ | | chromane-F | dioxane | chromane | | | OCF₃ |
| 128 | C₅H₁₁ | | chromane-F | dioxane | chromane | | | CN |
| 129 | CH₂=CH- | | chromane-F | dioxane | chromane | | | F |

TABLE-continued

Further example compounds

| | R¹ | A¹ | W¹ | A² | W² | Z⁴ | A³ | R² |
|---|---|---|---|---|---|---|---|---|
| 130 | CH₂=C(CH₃)– | | 3-methylchroman, 6-F | 2,5-dimethyl-1,3-dioxane | 3-methylchroman | | | CF₃ |
| 131 | CH₂=C(CH₃)– | | 3-methylchroman, 6-F | 2,5-dimethyl-1,3-dioxane | 3-methylchroman | | | OCF₃ |
| 132 | CH₂=C(CH₃)– | | 3-methylchroman, 6-F | 2,5-dimethyl-1,3-dioxane | 3-methylchroman | | | CN |
| 133 | C₃H₇– | | 3-methylchroman, 6-F | 2,5-dimethyl-1,3-dioxane | 3-methylchroman, 6-F | | | F |
| 134 | C₃H₇– | | 3-methylchroman, 6-F | 2,5-dimethyl-1,3-dioxane | 3-methylchroman, 6-F | | | CF₃ |
| 135 | C₃H₇– | | 3-methylchroman, 6-F | 2,5-dimethyl-1,3-dioxane | 3-methylchroman, 6-F | | | OCF₃ |
| 136 | C₃H₇– | | 3-methylchroman, 6-F | 2,5-dimethyl-1,3-dioxane | 3-methylchroman, 6-F | | | CN |

TABLE-continued

Further example compounds

| | R¹ | A¹ | W¹ | A² | W² | Z⁴ | A³ | R² |
|---|---|---|---|---|---|---|---|---|
| 137 | C₅H₁₁— | | | | | | | F |
| 138 | C₅H₁₁— | | | | | | | CF₃ |
| 139 | C₅H₁₁— | | | | | | | OCF₃ |
| 140 | C₅H₁₁— | | | | | | | CN |
| 141 | CH₂=CH–CH₂– | | | | | | | F |
| 142 | CH₂=CH–CH₂– | | | | | | | CF₃ |
| 143 | CH₂=CH–CH₂– | | | | | | | OCF₃ |

TABLE-continued

Further example compounds

| | R¹ | A¹ | W¹ | A² | W² | Z⁴ | A³ | R² |
|---|---|---|---|---|---|---|---|---|
| 144 | CH₂=C(CH₃)– | | chroman(F,F) | dioxane-Me | chroman(F,F) | | | CN |
| 145 | C₃H₇ | | chroman(F,F) | dioxane-Me | chroman(F,F,F) | | | F |
| 146 | C₃H₇ | | chroman(F,F) | dioxane-Me | chroman(F,F) | | | CF₃ |
| 147 | C₃H₇ | | chroman(F,F) | dioxane-Me | chroman(F,F) | | | OCF₃ |
| 148 | C₃H₇ | | chroman(F,F) | dioxane-Me | chroman(F,F) | | | CN |
| 149 | C₅H₁₁ | | chroman(F,F) | dioxane-Me | chroman(F,F) | | | F |

TABLE-continued

Further example compounds

| | $R^1$ | $A^1$ | $W^1$ | $A^2$ | $W^2$ | $Z^4$ | $A^3$ | $R^2$ |
|---|---|---|---|---|---|---|---|---|
| 150 | C$_5$H$_{11}$— | | chroman-F,Me | dioxane-Me | chroman-F,F,Me | | | CF$_3$ |
| 151 | C$_5$H$_{11}$— | | chroman-F,Me | dioxane-Me | chroman-F,F,Me | | | OCF$_3$ |
| 152 | C$_5$H$_{11}$— | | chroman-F,Me | dioxane-Me | chroman-F,F,Me | | | CN |
| 153 | isopropenyl | | chroman-F,Me | dioxane-Me | chroman-F,F,Me | | | F |
| 154 | isopropenyl | | chroman-F,Me | dioxane-Me | chroman-F,F,Me | | | CF$_3$ |
| 155 | isopropenyl | | chroman-F,Me | dioxane-Me | chroman-F,F,Me | | | OCF$_3$ |

TABLE-continued
Further example compounds
| | R¹ | A¹ | W¹ | A² | W² | Z⁴ | A³ | R² |
|---|---|---|---|---|---|---|---|---|
| 156 | 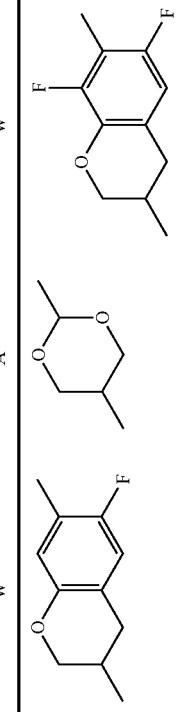 | | 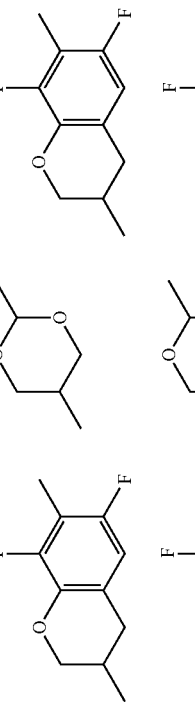 | 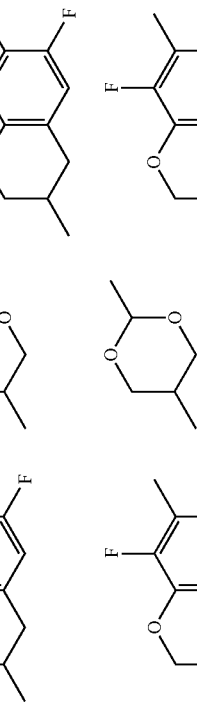 | 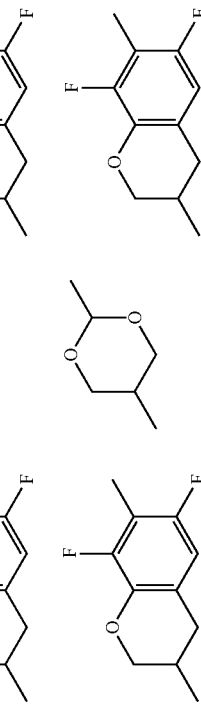 | | | CN |
| 157 | C₃H₇— | |  |  |  | | | F |
| 158 | C₃H₇— | |  |  | 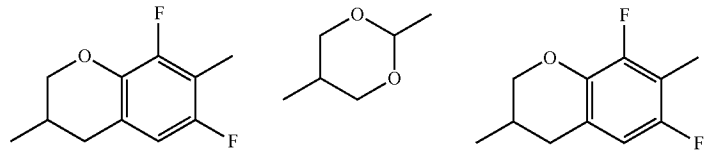 | | | CF₃ |
| 159 | C₃H₇— | |  |  | | | | OCF₃ |
| 160 | C₃H₇— | | | | | | | CN |
| 161 | C₅H₁₁— | | | | | | | F |

TABLE-continued

Further example compounds

| | R¹ | A¹ | W¹ | A² | W² | Z⁴ | A³ | R² |
|---|---|---|---|---|---|---|---|---|
| 162 | C₅H₁₁— | | (3-methylchroman-6,7,8-trifluoro) | (2-methyl-1,3-dioxane-5-yl) | (3-methylchroman-6,7,8-trifluoro) | | | CF₃ |
| 163 | C₅H₁₁— | | (3-methylchroman-6,7,8-trifluoro) | (2-methyl-1,3-dioxane-5-yl) | (3-methylchroman-6,7,8-trifluoro) | | | OCF₃ |
| 164 | C₅H₁₁— | | (3-methylchroman-6,7,8-trifluoro) | (2-methyl-1,3-dioxane-5-yl) | (3-methylchroman-6,7,8-trifluoro) | | | CN |
| 165 | CH₃CH=CH— | | (3-methylchroman-6,7,8-trifluoro) | (2-methyl-1,3-dioxane-5-yl) | (3-methylchroman-6,7,8-trifluoro) | | | F |
| 166 | CH₃CH=CH— | | (3-methylchroman-6,7,8-trifluoro) | (2-methyl-1,3-dioxane-5-yl) | (3-methylchroman-6,7,8-trifluoro) | | | CF₃ |
| 167 | CH₃CH=CH— | | (3-methylchroman-6,7,8-trifluoro) | (2-methyl-1,3-dioxane-5-yl) | (3-methylchroman-6,7,8-trifluoro) | | | OCF₃ |

TABLE-continued
Further example compounds
| | R¹ | A¹ | W¹ | A² | Z⁴ | W² | A³ | R² |
|---|---|---|---|---|---|---|---|---|
| 168 | 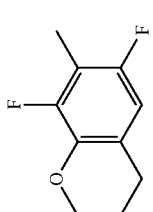 | 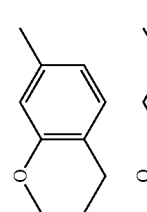 | 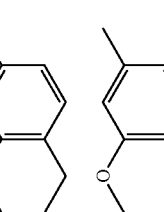 | 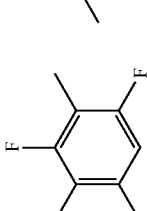 | | 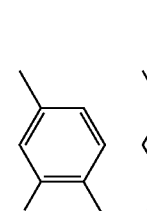 | | CN |
| 169 | C₃H₇ | 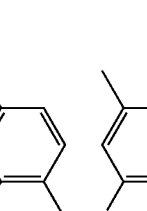 | 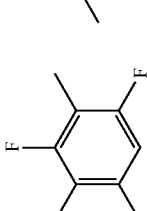 | | | 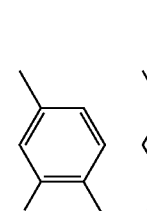 | | F |
| 170 | C₃H₇ | 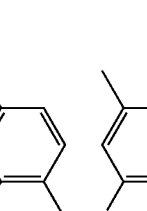 | 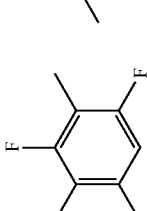 | | | 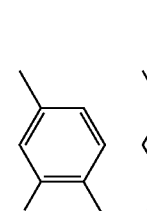 | | CF₃ |
| 171 | C₃H₇ | 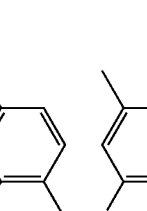 | 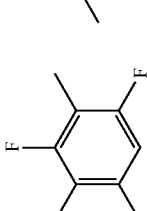 | | | 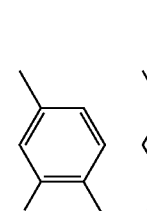 | | OCF₃ |
| 172 | C₃H₇ | 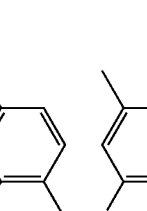 | 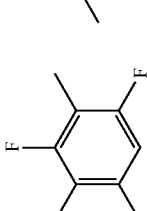 | | | 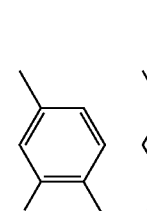 | | CN |
| 173 | C₅H₁₁ | 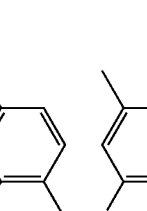 | 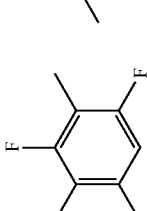 | | | 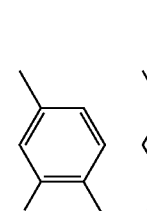 | | F |
| 174 | C₅H₁₁ | 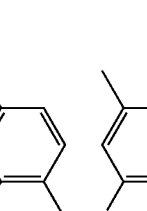 | 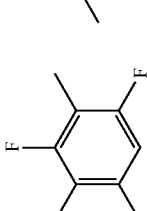 | | | 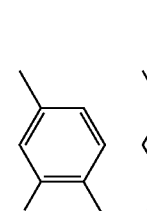 | | CF₃ |
| 175 | C₅H₁₁ | | | | | 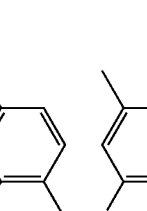 | | OCF₃ |

TABLE-continued
Further example compounds
| | R¹ | A¹ | W¹ | A² | W² | Z⁴ | A³ | R² |
|---|---|---|---|---|---|---|---|---|
| 176 | C₅H₁₁— | 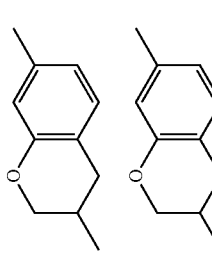 |  | |  | | | CN |
| 177 |  |  | 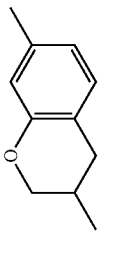 | | 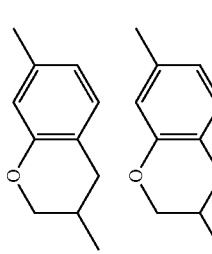 | | | F |
| 178 |  |  |  | | 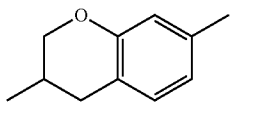 | | | CF₃ |
| 179 | 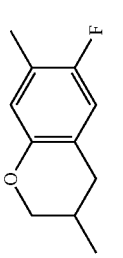 | 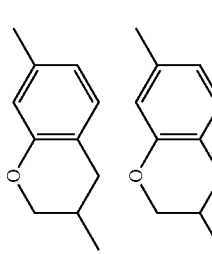 |  | |  | | | OCF₃ |
| 180 |  |  |  | |  | | | CN |
| 181 | C₃H₇— |  |  | |  | | | F |
| 182 | C₃H₇— |  |  | | 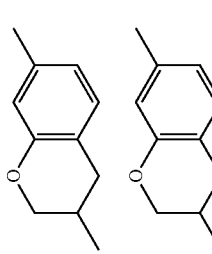 | | | CF₃ |

TABLE-continued

Further example compounds

| | R¹ | A¹ | W¹ | A² | W² | Z⁴ | A³ | R² |
|---|---|---|---|---|---|---|---|---|
| 183 | C₃H₇ | | | | | | | OCF₃ |
| 184 | C₃H₇ | | | | | | | CN |
| 185 | C₅H₁₁ | | | | | | | F |
| 186 | C₅H₁₁ | | | | | | | CF₃ |
| 187 | C₅H₁₁ | | | | | | | OCF₃ |
| 188 | C₅H₁₁ | | | | | | | CN |
| 189 | CH₂=CH- | | | | | | | F |
| 190 | CH₂=CH- | | | | | | | CF₃ |

TABLE-continued

Further example compounds

| R¹ | A¹ | W¹ | A² | W² | Z⁴ | A³ | R² |
|---|---|---|---|---|---|---|---|
| 191 | CH₂=C(CH₃)- | phenyl-CH₃ | 3-methylchroman | | 6-F,7-CH₃-3-methylchroman | | | OCF₃ |
| 192 | CH₂=C(CH₃)- | phenyl-CH₃ | 3-methylchroman | | 6-F,7-CH₃-3-methylchroman | | | CN |
| 193 | C₃H₇ | phenyl-CH₃ | 3-methylchroman | | 6,8-F,7-CH₃-3-methylchroman | | | F |
| 194 | C₃H₇ | phenyl-CH₃ | 3-methylchroman | | 6,8-F,7-CH₃-3-methylchroman | | | CF₃ |
| 195 | C₃H₇ | phenyl-CH₃ | 3-methylchroman | | 6,8-F,7-CH₃-3-methylchroman | | | OCF₃ |
| 196 | C₃H₇ | phenyl-CH₃ | 3-methylchroman | | 6,8-F,7-CH₃-3-methylchroman | | | CN |

TABLE-continued
Further example compounds
| | R¹ | A¹ | W¹ | A² | W² | Z⁴ | A³ | R² |
|---|---|---|---|---|---|---|---|---|
| 197 | C₅H₁₁— | 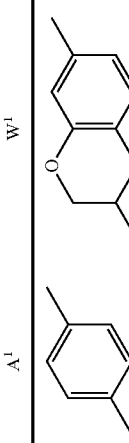 | 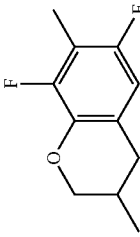 | | 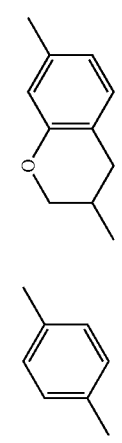 | | | F |
| 198 | C₅H₁₁— | 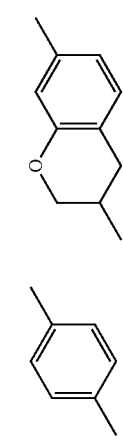 | 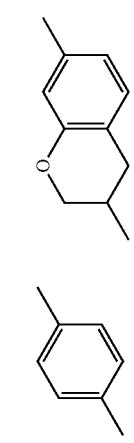 | | 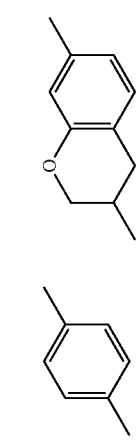 | | | CF₃ |
| 199 | C₅H₁₁— | 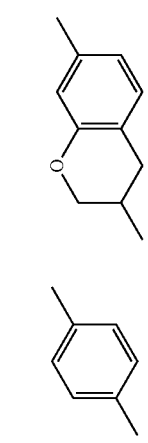 | 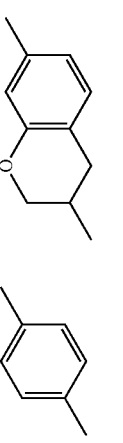 | | 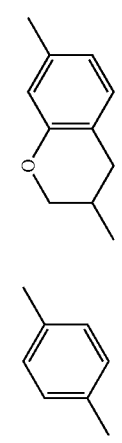 | | | OCF₃ |
| 200 | C₅H₁₁— | 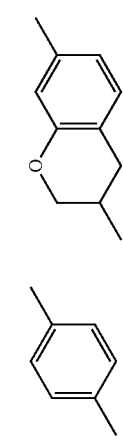 | 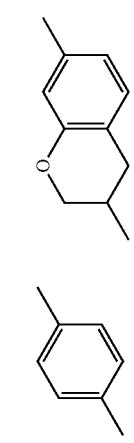 | | 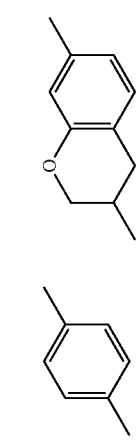 | | | CN |
| 201 | 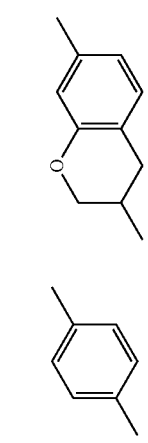 |  | 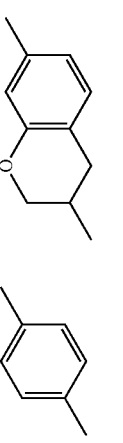 | | 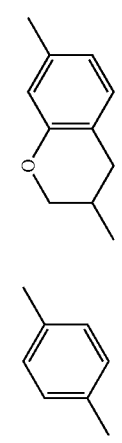 | | | F |
| 202 | 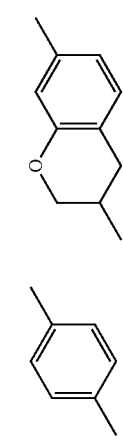 | 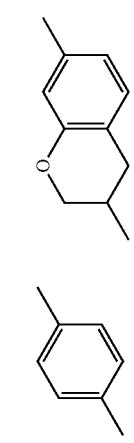 | 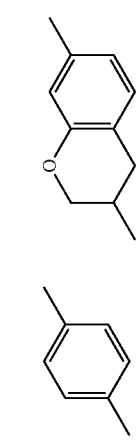 | | 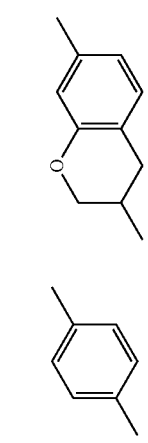 | | | CF₃ |

TABLE-continued

Further example compounds

| | R¹ | A¹ | W¹ | A² | W² | Z⁴ | A³ | R² |
|---|---|---|---|---|---|---|---|---|
| 203 | CH₂=C(CH₃)- | phenyl-CH₃ | 6-F-3-methylchroman | phenyl-CH₃ | 6,8-diF-7-methylchroman | | | OCF₃ |
| 204 | CH₂=C(CH₃)- | phenyl-CH₃ | 6-F-3-methylchroman | phenyl-CH₃ | 6,8-diF-7-methylchroman | | | CN |
| 205 | C₃H₇— | phenyl-CH₃ | 6-F-3-methylchroman | phenyl-CH₃ | 3-methylchroman | | | F |
| 206 | C₃H₇— | phenyl-CH₃ | 6-F-3-methylchroman | phenyl-CH₃ | 3-methylchroman | | | CF₃ |
| 207 | C₃H₇— | phenyl-CH₃ | 6-F-3-methylchroman | phenyl-CH₃ | 3-methylchroman | | | OCF₃ |
| 208 | C₃H₇— | phenyl-CH₃ | 6-F-3-methylchroman | phenyl-CH₃ | 3-methylchroman | | | CN |
| 209 | C₅H₁₁— | phenyl-CH₃ | 6-F-3-methylchroman | phenyl-CH₃ | 3-methylchroman | | | F |

TABLE-continued
Further example compounds
| | R¹ | A¹ | W¹ | A² | W² | Z⁴ | A³ | R² |
|---|---|---|---|---|---|---|---|---|
| 210 | C₅H₁₁— | 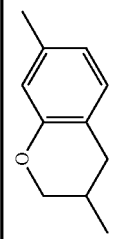 | 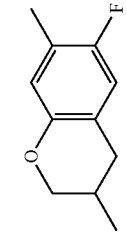 | |  | | | CF₃ |
| 211 | C₅H₁₁— | 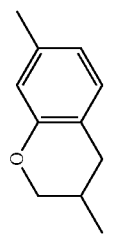 | 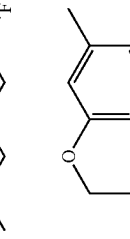 | | 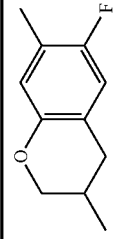 | | | OCF₃ |
| 212 | C₅H₁₁— | 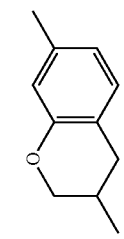 |  | | 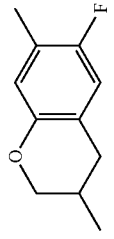 | | | CN |
| 213 | 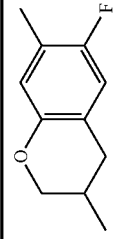 | 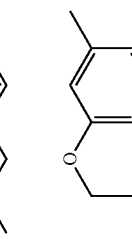 | 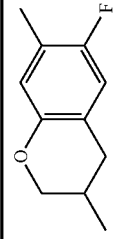 | | 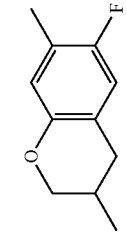 | | | F |
| 214 | 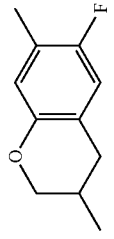 |  | 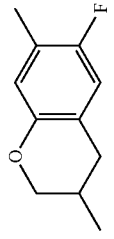 | | 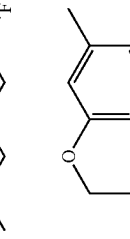 | | | CF₃ |
| 215 | 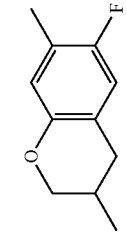 | 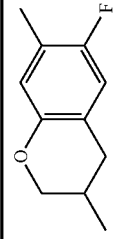 | 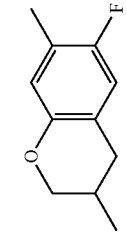 | |  | | | OCF₃ |
| 216 | 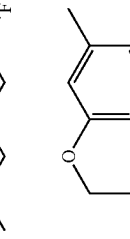 | 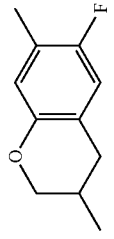 | 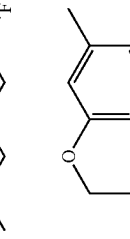 | | 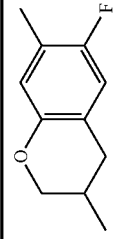 | | | CN |

TABLE-continued

Further example compounds

| | $R^1$ | $A^1$ | $W^1$ | $A^2$ | $W^2$ | $Z^4$ | $A^3$ | $R^2$ |
|---|---|---|---|---|---|---|---|---|
| 217 | $C_3H_7$— | (phenyl) | (fluoro-methyl-chromane) | | (fluoro-methyl-chromane) | | | F |
| 218 | $C_3H_7$— | (phenyl) | (fluoro-methyl-chromane) | | (fluoro-methyl-chromane) | | | $CF_3$ |
| 219 | $C_3H_7$— | (phenyl) | (fluoro-methyl-chromane) | | (fluoro-methyl-chromane) | | | $OCF_3$ |
| 220 | $C_3H_7$— | (phenyl) | (fluoro-methyl-chromane) | | (fluoro-methyl-chromane) | | | CN |
| 221 | $C_5H_{11}$— | (phenyl) | (fluoro-methyl-chromane) | | (fluoro-methyl-chromane) | | | F |
| 222 | $C_5H_{11}$— | (phenyl) | (fluoro-methyl-chromane) | | (fluoro-methyl-chromane) | | | $CF_3$ |
| 223 | $C_5H_{11}$— | (phenyl) | (fluoro-methyl-chromane) | | (fluoro-methyl-chromane) | | | $OCF_3$ |
| 224 | $C_5H_{11}$— | (phenyl) | (fluoro-methyl-chromane) | | (fluoro-methyl-chromane) | | | CN |

TABLE-continued

Further example compounds

| | R¹ | A¹ | W¹ | A² | W² | Z⁴ | A³ | R² |
|---|---|---|---|---|---|---|---|---|
| 225 | CH=CH₂ (isopropenyl) | 4-methylphenyl | 6-F-3-methylchroman | | 6-F-3-methylchroman | | | F |
| 226 | CH=CH₂ (isopropenyl) | 4-methylphenyl | 6-F-3-methylchroman | | 6-F-3-methylchroman | | | CF₃ |
| 227 | CH=CH₂ (isopropenyl) | 4-methylphenyl | 6-F-3-methylchroman | | 6-F-3-methylchroman | | | OCF₃ |
| 228 | CH=CH₂ (isopropenyl) | 4-methylphenyl | 6-F-3-methylchroman | | 6-F-3-methylchroman | | | CN |
| 229 | C₃H₇ | 4-methylphenyl | 6-F-3-methylchroman | | 6,8-diF-3-methylchroman | | | F |
| 230 | C₃H₇ | 4-methylphenyl | 6-F-3-methylchroman | | 6,8-diF-3-methylchroman | | | CF₃ |

TABLE-continued
Further example compounds
| | R¹ | A¹ | W¹ | A² | W² | Z⁴ | A³ | R² |
|---|---|---|---|---|---|---|---|---|
| 231 | C₃H₇ |  | 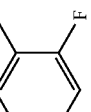 | | 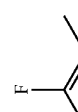 | | | OCF₃ |
| 232 | C₃H₇ | 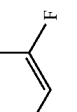 | 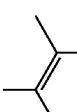 | |  | | | CN |
| 233 | C₅H₁₁ | 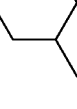 |  | | 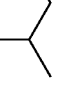 | | | F |
| 234 | C₅H₁₁ | 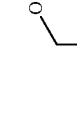 |  | |  | | | CF₃ |
| 235 | C₅H₁₁ |  |  | |  | | | OCF₃ |
| 236 | C₅H₁₁ | 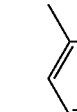 | 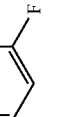 | | 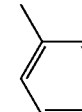 | | | CN |

TABLE-continued

Further example compounds

| | R¹ | A¹ | W¹ | A² | W² | Z⁴ | A³ | R² |
|---|---|---|---|---|---|---|---|---|
| 237 | CH₂=C(CH₃)- | phenyl | 6-F-3-methylchroman | | 6,8-diF-3-methylchroman | | | F |
| 238 | CH₂=C(CH₃)- | phenyl | 6-F-3-methylchroman | | 6,8-diF-3-methylchroman | | | CF₃ |
| 239 | CH₂=C(CH₃)- | phenyl | 6-F-3-methylchroman | | 6,8-diF-3-methylchroman | | | OCF₃ |
| 240 | CH₂=C(CH₃)- | phenyl | 6-F-3-methylchroman | | 6,8-diF-3-methylchroman | | | CN |
| 241 | C₃H₇ | phenyl | 6,8-diF-3-methylchroman | | 6,8-diF-3-methylchroman | | | F |
| 242 | C₃H₇ | phenyl | 6,8-diF-3-methylchroman | | 6,8-diF-3-methylchroman | | | CF₃ |

TABLE-continued
Further example compounds
| | $R^1$ | $A^1$ | $W^1$ | $A^2$ | $W^2$ | $Z^4$ | $A^3$ | $R^2$ |
|---|---|---|---|---|---|---|---|---|
| 243 | $C_3H_7$— | 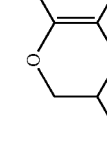 | 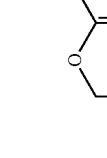 | | 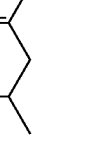 | | | $OCF_3$ |
| 244 | $C_3H_7$— | 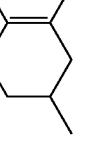 | 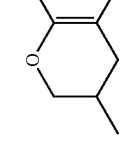 | | 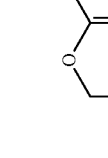 | | | CN |
| 245 | $C_5H_{11}$— | 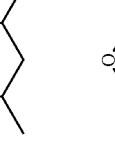 | 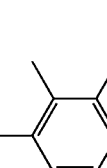 | | 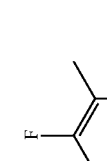 | | | F |
| 246 | $C_5H_{11}$— | 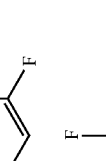 | 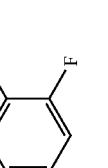 | | 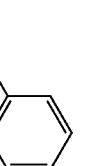 | | | $CF_3$ |
| 247 | $C_5H_{11}$— | 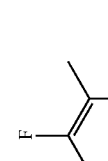 |  | | 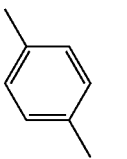 | | | $OCF_3$ |
| 248 | $C_5H_{11}$— | 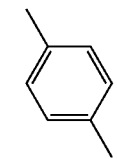 | 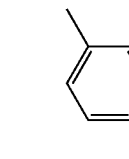 | | 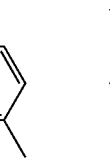 | | | CN |

TABLE-continued
Further example compounds
| R¹ | A¹ | W¹ | A² | W² | Z⁴ | A³ | R² |
|---|---|---|---|---|---|---|---|
| 249 | 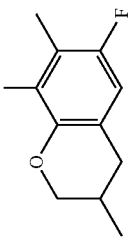 | 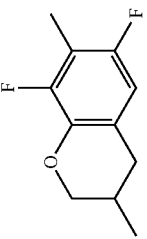 | | 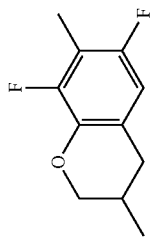 | 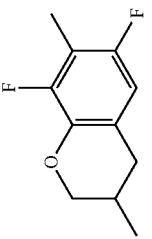 | | | F |
| 250 | 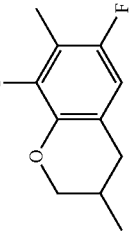 | 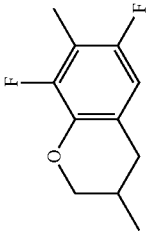 | | 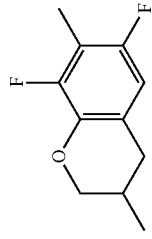 | 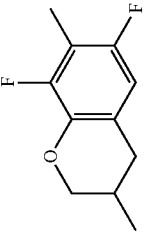 | | | CF₃ |
| 251 |  |  | |  |  | | | OCF₃ |
| 252 |  |  | |  |  | | | CN |
| 253 | C₃H₇ |  | 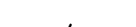 | |  | | | F |
| 254 | C₃H₇ |  |  | |  | | | CF₃ |

TABLE-continued
Further example compounds
| | R$^1$ | A$^1$ | W$^1$ | A$^2$ | W$^2$ | Z$^4$ | A$^3$ | R$^2$ |
|---|---|---|---|---|---|---|---|---|
| 255 | C$_3$H$_7$ | 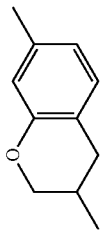 | 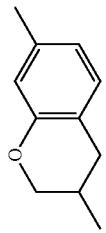 | | 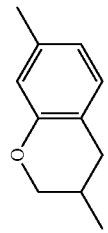 | | | OCF$_3$ |
| 256 | C$_3$H$_7$ | 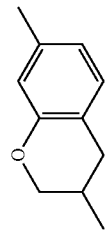 | 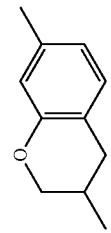 | | 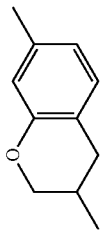 | | | CN |
| 257 | C$_5$H$_{11}$ | 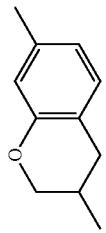 | 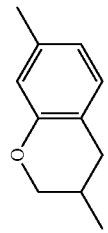 | | 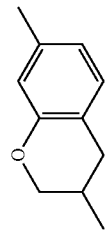 | | | F |
| 258 | C$_5$H$_{11}$ | 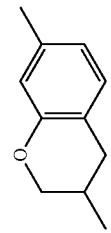 | 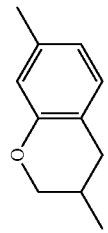 | | 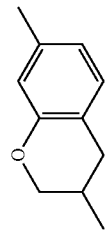 | | | CF$_3$ |
| 259 | C$_5$H$_{11}$ | 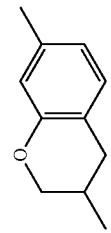 | 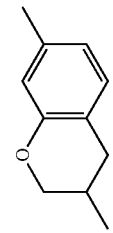 | | 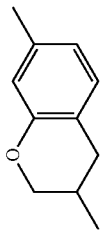 | | | OCF$_3$ |
| 260 | C$_5$H$_{11}$ | 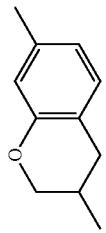 | 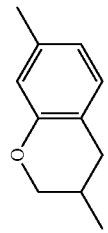 | | 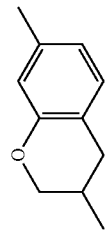 | | | CN |

TABLE-continued

Further example compounds

| R¹ | A¹ | W¹ | A² | W² | Z⁴ | A³ | R² |
|---|---|---|---|---|---|---|---|
| 261 | CH₂=CH- | F-phenyl-CH₃ | 3-methylchroman | | 7-methylchroman | | | F |
| 262 | CH₂=CH- | F-phenyl-CH₃ | 3-methylchroman | | 7-methylchroman | | | CF₃ |
| 263 | CH₂=CH- | F-phenyl-CH₃ | 3-methylchroman | | 7-methylchroman | | | OCF₃ |
| 264 | CH₂=CH- | F-phenyl-CH₃ | 3-methylchroman | | 7-methylchroman | | | CN |
| 265 | C₃H₇ | F-phenyl-CH₃ | 3-methylchroman | | 6-F-7-methylchroman | | | F |
| 266 | C₃H₇ | F-phenyl-CH₃ | 3-methylchroman | | 6-F-7-methylchroman | | | CF₃ |

TABLE-continued

Further example compounds

| | $R^1$ | $A^1$ | $W^1$ | $A^2$ | $W^2$ | $Z^4$ | $A^3$ | $R^2$ |
|---|---|---|---|---|---|---|---|---|
| 267 | $C_3H_7$— | [2-F,4-yl phenyl] | [3-methyl chroman] | | [6-F,7-methyl chroman] | | | $OCF_3$ |
| 268 | $C_3H_7$— | [2-F,4-yl phenyl] | [3-methyl chroman] | | [6-F,7-methyl chroman] | | | CN |
| 269 | $C_5H_{11}$— | [2-F,4-yl phenyl] | [3-methyl chroman] | | [6-F,7-methyl chroman] | | | F |
| 270 | $C_5H_{11}$— | [2-F,4-yl phenyl] | [3-methyl chroman] | | [6-F,7-methyl chroman] | | | $CF_3$ |
| 271 | $C_5H_{11}$— | [2-F,4-yl phenyl] | [3-methyl chroman] | | [6-F,7-methyl chroman] | | | $OCF_3$ |
| 272 | $C_5H_{11}$— | [2-F,4-yl phenyl] | [3-methyl chroman] | | [6-F,7-methyl chroman] | | | CN |

TABLE-continued

Further example compounds

| | R¹ | A¹ | W¹ | A² | W² | Z⁴ | A³ | R² |
|---|---|---|---|---|---|---|---|---|
| 273 | CH₂=C(CH₃)– | 3-F-4-Me-phenyl | 3-Me-chroman | | 6-F-7-Me-chroman | | | F |
| 274 | CH₂=C(CH₃)– | 3-F-4-Me-phenyl | 3-Me-chroman | | 6-F-7-Me-chroman | | | CF₃ |
| 275 | CH₂=C(CH₃)– | 3-F-4-Me-phenyl | 3-Me-chroman | | 6-F-7-Me-chroman | | | OCF₃ |
| 276 | CH₂=C(CH₃)– | 3-F-4-Me-phenyl | 3-Me-chroman | | 6-F-7-Me-chroman | | | CN |
| 277 | C₃H₇– | 3-F-4-Me-phenyl | 3-Me-chroman | | 6-F-7-Me-8-F-chroman | | | F |
| 278 | C₃H₇– | 3-F-4-Me-phenyl | 3-Me-chroman | | 6-F-7-Me-8-F-chroman | | | CF₃ |

TABLE-continued

Further example compounds

| | R¹ | A¹ | W¹ | A² | W² | Z⁴ | A³ | R² |
|---|---|---|---|---|---|---|---|---|
| 279 | C₃H₇ | | | | | | | OCF₃ |
| 280 | C₃H₇ | | | | | | | CN |
| 281 | C₅H₁₁ | | | | | | | F |
| 282 | C₅H₁₁ | | | | | | | CF₃ |
| 283 | C₅H₁₁ | | | | | | | OCF₃ |
| 284 | C₅H₁₁ | | | | | | | CN |

TABLE-continued

Further example compounds

| | R¹ | A¹ | W¹ | A² | W² | Z⁴ | A³ | R² |
|---|---|---|---|---|---|---|---|---|
| 285 | CH=C(CH₃)- (isobutenyl) | 2-F,5-Me phenyl | 6-Me,3-Me chroman | | 6-F,8-F,3-Me chroman | | | F |
| 286 | CH=C(CH₃)- | 2-F,5-Me phenyl | 6-Me,3-Me chroman | | 6-F,8-F,3-Me chroman | | | CF₃ |
| 287 | CH=C(CH₃)- | 2-F,5-Me phenyl | 6-Me,3-Me chroman | | 6-F,8-F,3-Me chroman | | | OCF₃ |
| 288 | CH=C(CH₃)- | 2-F,5-Me phenyl | 6-Me,3-Me chroman | | 6-F,8-F,3-Me chroman | | | CN |
| 289 | C₃H₇ | 2-F,5-Me phenyl | 6-F,7-Me,3-Me chroman | | 7-Me,3-Me chroman | | | F |
| 290 | C₃H₇ | 2-F,5-Me phenyl | 6-F,7-Me,3-Me chroman | | 7-Me,3-Me chroman | | | CF₃ |

TABLE-continued

Further example compounds

| | R¹ | A¹ | W¹ | A² | W² | Z⁴ | A³ | R² |
|---|---|---|---|---|---|---|---|---|
| 291 | C₃H₇ | (2-F,5-Me-phenyl) | (6-F,7-Me-3-methylchroman) | | (7-Me-3-methylchroman) | | | OCF₃ |
| 292 | C₃H₇ | (2-F,5-Me-phenyl) | (6-F,7-Me-3-methylchroman) | | (7-Me-3-methylchroman) | | | CN |
| 293 | C₅H₁₁ | (2-F,5-Me-phenyl) | (6-F,7-Me-3-methylchroman) | | (7-Me-3-methylchroman) | | | F |
| 294 | C₅H₁₁ | (2-F,5-Me-phenyl) | (6-F,7-Me-3-methylchroman) | | (7-Me-3-methylchroman) | | | CF₃ |
| 295 | C₅H₁₁ | (2-F,5-Me-phenyl) | (6-F,7-Me-3-methylchroman) | | (7-Me-3-methylchroman) | | | OCF₃ |
| 296 | C₅H₁₁ | (2-F,5-Me-phenyl) | (6-F,7-Me-3-methylchroman) | | (7-Me-3-methylchroman) | | | CN |

TABLE-continued
Further example compounds
| | R¹ | A¹ | W¹ | A² | W² | Z⁴ | A³ | R² |
|---|---|---|---|---|---|---|---|---|
| 297 | 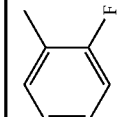 | | | | | | | F |
| 298 | | | | | | | | CF₃ |
| 299 | | | | | | | | OCF₃ |
| 300 | | | | | | | | CN |
| 301 | C₃H₇— | | | | | | | F |
| 302 | C₃H₇— | | | | | | | CF₃ |

TABLE-continued

Further example compounds

| | $R^1$ | $A^1$ | $W^1$ | $A^2$ | $W^2$ | $Z^4$ | $A^3$ | $R^2$ |
|---|---|---|---|---|---|---|---|---|
| 303 | $C_3H_7$ | 2-F,4-Me-phenyl | 6-F,8-Me-3-methylchroman | | 6-F,8-Me-3-methylchroman | | | $OCF_3$ |
| 304 | $C_3H_7$ | 2-F,4-Me-phenyl | 6-F,8-Me-3-methylchroman | | 6-F,8-Me-3-methylchroman | | | CN |
| 305 | $C_5H_{11}$ | 2-F,4-Me-phenyl | 6-F,8-Me-3-methylchroman | | 6-F,8-Me-3-methylchroman | | | F |
| 306 | $C_5H_{11}$ | 2-F,4-Me-phenyl | 6-F,8-Me-3-methylchroman | | 6-F,8-Me-3-methylchroman | | | $CF_3$ |
| 307 | $C_5H_{11}$ | 2-F,4-Me-phenyl | 6-F,8-Me-3-methylchroman | | 6-F,8-Me-3-methylchroman | | | $OCF_3$ |
| 308 | $C_5H_{11}$ | 2-F,4-Me-phenyl | 6-F,8-Me-3-methylchroman | | 6-F,8-Me-3-methylchroman | | | CN |

TABLE-continued

Further example compounds

| # | R¹ | A¹ | W¹ | A² | W² | Z⁴ | A³ | R² |
|---|---|---|---|---|---|---|---|---|
| 309 | CH₂=C(CH₃)- | difluoromethylphenyl | methylchroman-F | | methylchroman-F | | | F |
| 310 | CH₂=C(CH₃)- | difluoromethylphenyl | methylchroman-F | | methylchroman-F | | | CF₃ |
| 311 | CH₂=C(CH₃)- | difluoromethylphenyl | methylchroman-F | | methylchroman-F | | | OCF₃ |
| 312 | CH₂=C(CH₃)- | difluoromethylphenyl | methylchroman-F | | methylchroman-F | | | CN |
| 313 | C₃H₇ | difluoromethylphenyl | methylchroman-F | | methylchroman-diF | | | F |
| 314 | C₃H₇ | difluoromethylphenyl | methylchroman-F | | methylchroman-diF | | | CF₃ |

TABLE-continued
Further example compounds
| | $R^1$ | $A^1$ | $W^1$ | $A^2$ | $W^2$ | $Z^4$ | $A^3$ | $R^2$ |
|---|---|---|---|---|---|---|---|---|
| 315 | $C_3H_7$— | 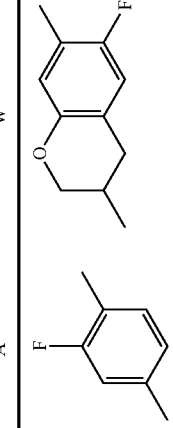 | 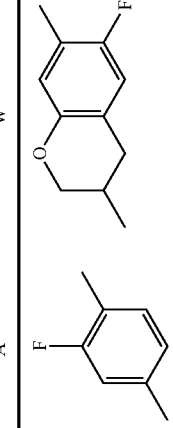 | | 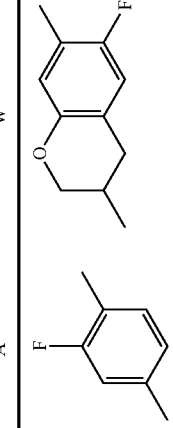 | | | $OCF_3$ |
| 316 | $C_3H_7$— | 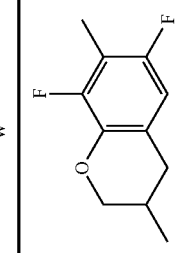 | 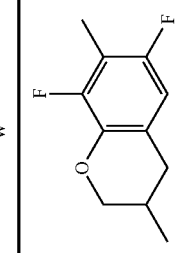 | | 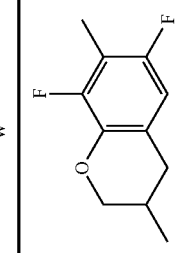 | | | $CN$ |
| 317 | $C_5H_{11}$— | 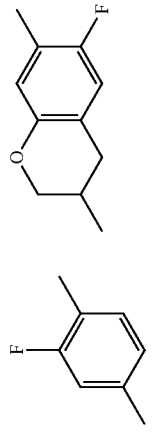 | 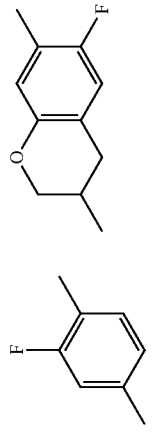 | | 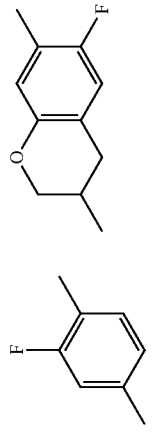 | | | $F$ |
| 318 | $C_5H_{11}$— | 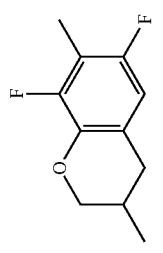 | 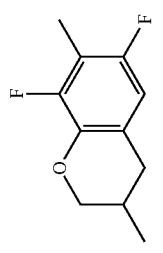 | | 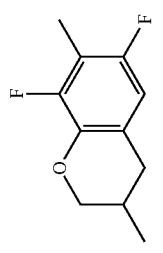 | | | $CF_3$ |
| 319 | $C_5H_{11}$— | 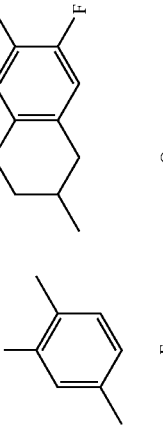 | 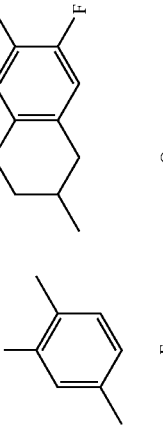 | | 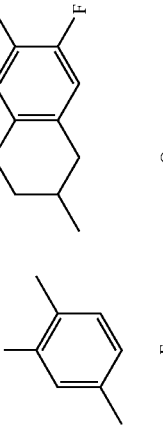 | | | $OCF_3$ |
| 320 | $C_5H_{11}$— | 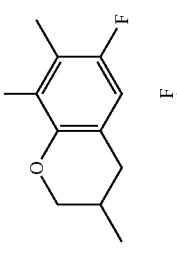 | 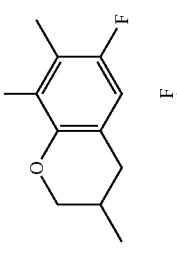 | | 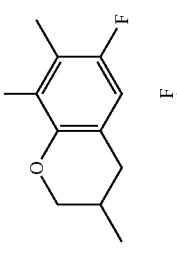 | | | $CN$ |

TABLE-continued

Further example compounds

| | R¹ | A¹ | W¹ | A² | W² | Z⁴ | A³ | R² |
|---|---|---|---|---|---|---|---|---|
| 321 | CH₂=C(CH₃)- | F-phenyl-CH₃ | 3-methylchroman-F,F | | 3-methylchroman-F,F | | | F |
| 322 | CH₂=C(CH₃)- | F-phenyl-CH₃ | 3-methylchroman-F,F | | 3-methylchroman-F,F | | | CF₃ |
| 323 | CH₂=C(CH₃)- | F-phenyl-CH₃ | 3-methylchroman-F,F | | 3-methylchroman-F,F | | | OCF₃ |
| 324 | CH₂=C(CH₃)- | F-phenyl-CH₃ | 3-methylchroman-F,F | | 3-methylchroman-F,F | | | CN |
| 325 | C₃H₇- | F-phenyl-CH₃ | 3-methylchroman-F,F | | 3-methylchroman-F,F | | | F |
| 326 | C₃H₇- | F-phenyl-CH₃ | 3-methylchroman-F,F | | 3-methylchroman-F,F | | | CF₃ |

TABLE-continued
Further example compounds
| | R¹ | A¹ | W¹ | A² | W² | Z⁴ | A³ | R² |
|---|---|---|---|---|---|---|---|---|
| 327 | C₃H₇— | 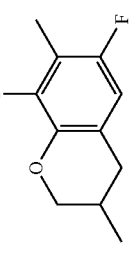 | 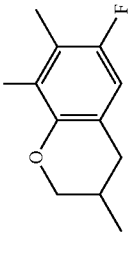 | | 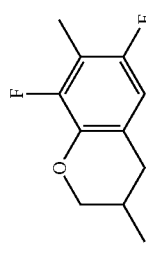 | | | OCF₃ |
| 328 | C₃H₇— | 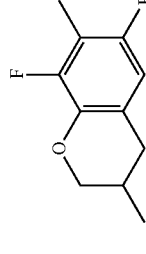 | 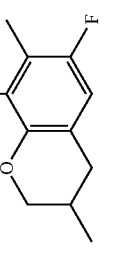 | | 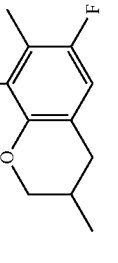 | | | CN |
| 329 | C₅H₁₁— | 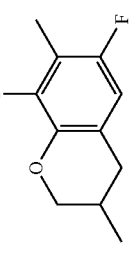 | 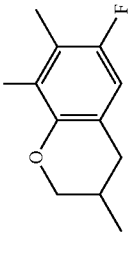 | | 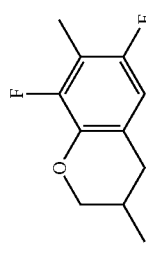 | | | F |
| 330 | C₅H₁₁— | 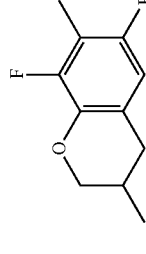 | 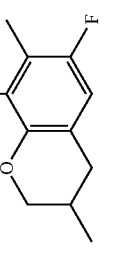 | | 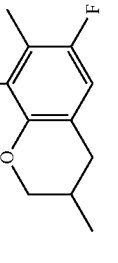 | | | CF₃ |
| 331 | C₅H₁₁— | 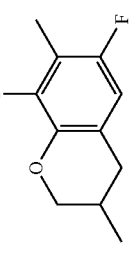 | 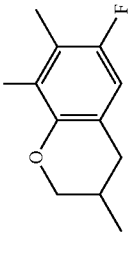 | | 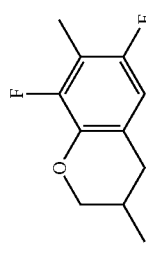 | | | OCF₃ |
| 332 | C₅H₁₁— | 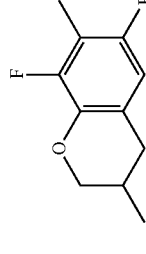 | 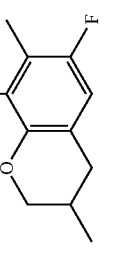 | | 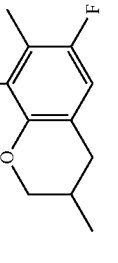 | | | CN |

TABLE-continued
Further example compounds
| | $R^1$ | $A^1$ | $W^1$ | $A^2$ | $W^2$ | $Z^4$ | $A^3$ | $R^2$ |
|---|---|---|---|---|---|---|---|---|
| 333 |  |  |  | |  | | | F |
| 334 |  |  |  | |  | | | $CF_3$ |
| 335 |  |  |  | |  | | | $OCF_3$ |
| 336 |  |  |  | |  | | | CN |
| 337 | $C_3H_7$ | |  |  |  | | | F |
| 338 | $C_3H_7$ | |  |  |  | | | $CF_3$ |
| 339 | $C_3H_7$ | |  |  |  | | | $OCF_3$ |

TABLE-continued
Further example compounds
| | $R^1$ | $A^1$ | $W^1$ | $A^2$ | $W^2$ | $Z^4$ | $A^3$ | $R^2$ |
|---|---|---|---|---|---|---|---|---|
| 340 | $C_3H_7$— | | 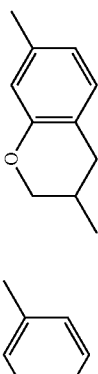 | 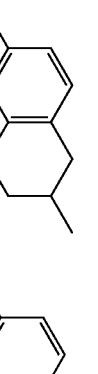 | 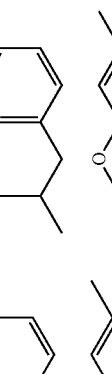 | | | CN |
| 341 | $C_5H_{11}$— | | 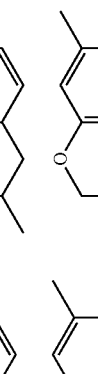 | 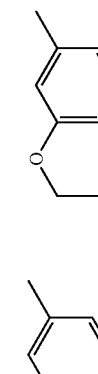 | 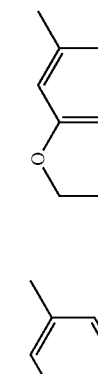 | | | F |
| 342 | $C_5H_{11}$— | | 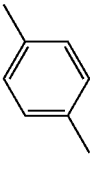 | 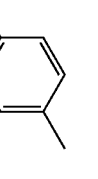 | 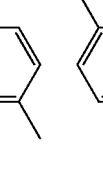 | | | $CF_3$ |
| 343 | $C_5H_{11}$— | | 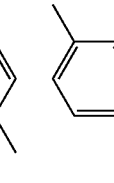 | 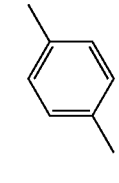 | 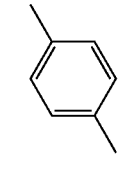 | | | $OCF_3$ |
| 344 | $C_5H_{11}$— | | 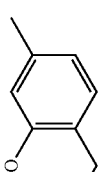 | 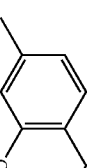 | 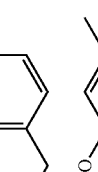 | | | CN |
| 345 | 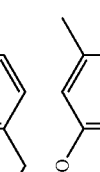 | | 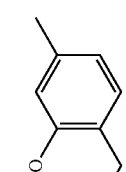 | 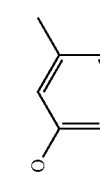 | 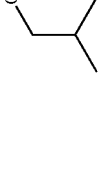 | | | F |
| 346 |  | | 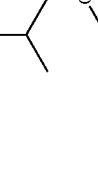 | 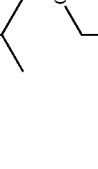 | 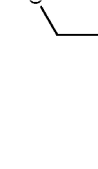 | | | $CF_3$ |

TABLE-continued

Further example compounds

| R¹ | A¹ | W¹ | A² | W² | Z⁴ | A³ | R² |
|---|---|---|---|---|---|---|---|
| 347 | CH=CH₂ (H,H,H,CH₃) | chromanyl-CH₃ | phenyl-CH₃ | chromanyl-CH₃ | | | OCF₃ |
| 348 | CH=CH₂ (H,H,H,CH₃) | chromanyl-CH₃ | phenyl-CH₃ | chromanyl-CH₃ | | | CN |
| 349 | $C_3H_7$ | chromanyl-CH₃ | phenyl-CH₃ | chromanyl-CH₃-F | | | F |
| 350 | $C_3H_7$ | chromanyl-CH₃ | phenyl-CH₃ | chromanyl-CH₃-F | | | $CF_3$ |
| 351 | $C_3H_7$ | chromanyl-CH₃ | phenyl-CH₃ | chromanyl-CH₃-F | | | $OCF_3$ |
| 352 | $C_3H_7$ | chromanyl-CH₃ | phenyl-CH₃ | chromanyl-CH₃-F | | | CN |
| 353 | $C_5H_{11}$ | chromanyl-CH₃ | phenyl-CH₃ | chromanyl-CH₃-F | | | F |
| 354 | $C_5H_{11}$ | chromanyl-CH₃ | phenyl-CH₃ | chromanyl-CH₃-F | | | $CF_3$ |

TABLE-continued

Further example compounds

| | R$^1$ | A$^1$ | W$^1$ | A$^2$ | W$^2$ | Z$^4$ | A$^3$ | R$^2$ |
|---|---|---|---|---|---|---|---|---|
| 355 | C$_5$H$_{11}$— | | | | | | | OCF$_3$ |
| 356 | C$_5$H$_{11}$— | | | | | | | CN |
| 357 | CH$_2$=C(CH$_3$)— | | | | | | | F |
| 358 | CH$_2$=C(CH$_3$)— | | | | | | | CF$_3$ |
| 359 | CH$_2$=C(CH$_3$)— | | | | | | | OCF$_3$ |
| 360 | CH$_2$=C(CH$_3$)— | | | | | | | CN |
| 361 | C$_3$H$_7$— | | | | | | | F |

TABLE-continued

Further example compounds

| | $R^1$ | $A^1$ | $A^2$ | $W^2$ | $Z^4$ | $A^3$ | $R^2$ |
|---|---|---|---|---|---|---|---|
| 362 | $C_3H_7-$ | | | | | | $CF_3$ |
| 363 | $C_3H_7-$ | | | | | | $OCF_3$ |
| 364 | $C_3H_7-$ | | | | | | $CN$ |
| 365 | $C_5H_{11}-$ | | | | | | $F$ |
| 366 | $C_5H_{11}-$ | | | | | | $CF_3$ |
| 367 | $C_5H_{11}-$ | | | | | | $OCF_3$ |

TABLE-continued

Further example compounds

| | R¹ | A¹ | W¹ | A² | W² | Z⁴ | A³ | R² |
|---|---|---|---|---|---|---|---|---|
| 368 | C₅H₁₁— | | | | | | | CN |
| 369 | | | | | | | | F |
| 370 | | | | | | | | CF₃ |
| 371 | | | | | | | | OCF₃ |
| 372 | | | | | | | | CN |
| 373 | C₃H₇— | | | | | | | F |

TABLE-continued

Further example compounds

| | R¹ | A¹ | W¹ | A² | W² | Z⁴ | A³ | R² |
|---|---|---|---|---|---|---|---|---|
| 374 | C₃H₇— | | (6-F chromane-3-methyl) | (phenyl) | (7-methyl chromane-3-methyl) | | | CF₃ |
| 375 | C₃H₇— | | (6-F chromane-3-methyl) | (phenyl) | (7-methyl chromane-3-methyl) | | | OCF₃ |
| 376 | C₃H₇— | | (6-F chromane-3-methyl) | (phenyl) | (7-methyl chromane-3-methyl) | | | CN |
| 377 | C₅H₁₁— | | (6-F chromane-3-methyl) | (phenyl) | (7-methyl chromane-3-methyl) | | | F |
| 378 | C₅H₁₁— | | (6-F chromane-3-methyl) | (phenyl) | (7-methyl chromane-3-methyl) | | | CF₃ |
| 379 | C₅H₁₁— | | (6-F chromane-3-methyl) | (phenyl) | (7-methyl chromane-3-methyl) | | | OCF₃ |
| 380 | C₅H₁₁— | | (6-F chromane-3-methyl) | (phenyl) | (7-methyl chromane-3-methyl) | | | CN |
| 381 | CH₂=CH— | | (6-F chromane-3-methyl) | (phenyl) | (7-methyl chromane-3-methyl) | | | F |

TABLE-continued

Further example compounds

| | R¹ | A¹ | W¹ | A² | W² | Z⁴ | A³ | R² |
|---|---|---|---|---|---|---|---|---|
| 382 | CH₂=C(CH₃)- | | fluoro-methylchroman | phenyl | methylchroman | | | CF₃ |
| 383 | CH₂=C(CH₃)- | | fluoro-methylchroman | phenyl | methylchroman | | | OCF₃ |
| 384 | CH₂=C(CH₃)- | | fluoro-methylchroman | phenyl | methylchroman | | | CN |
| 385 | C₃H₇- | | fluoro-methylchroman | phenyl | fluoro-methylchroman | | | F |
| 386 | C₃H₇- | | fluoro-methylchroman | phenyl | fluoro-methylchroman | | | CF₃ |
| 387 | C₃H₇- | | fluoro-methylchroman | phenyl | fluoro-methylchroman | | | OCF₃ |
| 388 | C₃H₇- | | fluoro-methylchroman | phenyl | fluoro-methylchroman | | | CN |

TABLE-continued

Further example compounds

| | R¹ | A¹ | W¹ | A² | W² | Z⁴ | A³ | R² |
|---|---|---|---|---|---|---|---|---|
| 389 | C₅H₁₁— | | chroman-F | phenyl | chroman-F | | | F |
| 390 | C₅H₁₁— | | chroman-F | phenyl | chroman-F | | | CF₃ |
| 391 | C₅H₁₁— | | chroman-F | phenyl | chroman-F | | | OCF₃ |
| 392 | C₅H₁₁— | | chroman-F | phenyl | chroman-F | | | CN |
| 393 | CH₃CH=CH— | | chroman-F | phenyl | chroman-F | | | F |
| 394 | CH₃CH=CH— | | chroman-F | phenyl | chroman-F | | | CF₃ |
| 395 | CH₃CH=CH— | | chroman-F | phenyl | chroman-F | | | OCF₃ |

TABLE-continued

Further example compounds

| | R¹ | A¹ | W¹ | A² | W² | Z⁴ | A³ | R² |
|---|---|---|---|---|---|---|---|---|
| 396 | CH₂=C(CH₃)– | | 3-methylchroman-6-yl (5-F) | 1,4-phenylene | 3-methylchroman-6-yl (5,8-diF) | | | CN |
| 397 | C₃H₇– | | 3-methylchroman-6-yl (5-F) | 1,4-phenylene | 3-methylchroman-6-yl (5,8-diF) | | | F |
| 398 | C₃H₇– | | 3-methylchroman-6-yl (5-F) | 1,4-phenylene | 3-methylchroman-6-yl (5,8-diF) | | | CF₃ |
| 399 | C₃H₇– | | 3-methylchroman-6-yl (5-F) | 1,4-phenylene | 3-methylchroman-6-yl (5,8-diF) | | | OCF₃ |
| 400 | C₃H₇– | | 3-methylchroman-6-yl (5-F) | 1,4-phenylene | 3-methylchroman-6-yl (5,8-diF) | | | CN |
| 401 | C₅H₁₁– | | 3-methylchroman-6-yl (5-F) | 1,4-phenylene | 3-methylchroman-6-yl (5,8-diF) | | | F |

TABLE-continued
Further example compounds
| | R¹ | A¹ | W¹ | A² | W² | Z⁴ | A³ | R² |
|---|---|---|---|---|---|---|---|---|
| 402 | C₅H₁₁— | |  | 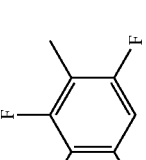 | 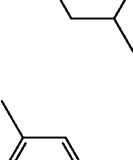 | | | CF₃ |
| 403 | C₅H₁₁— | |  | 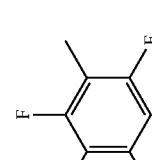 | 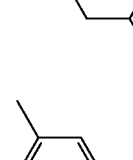 | | | OCF₃ |
| 404 | C₅H₁₁— | |  | 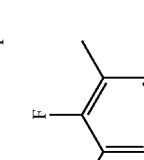 | 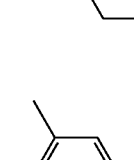 | | | CN |
| 405 | 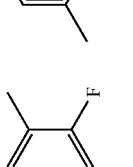 | |  | 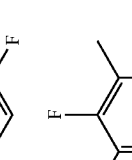 | 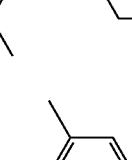 | | | F |
| 406 | 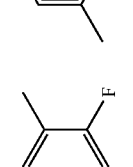 | |  | 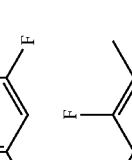 | 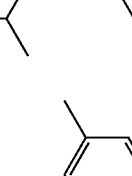 | | | CF₃ |
| 407 | 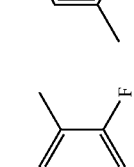 | |  | 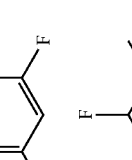 | 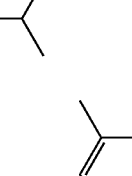 | | | OCF₃ |

TABLE-continued

Further example compounds

| | $R^1$ | $A^1$ | $W^1$ | $A^2$ | $W^2$ | $Z^4$ | $A^3$ | $R^2$ |
|---|---|---|---|---|---|---|---|---|
| 408 | CH₂=C(CH₃)– | | chroman-F,F | phenyl | chroman-F,F | | | CN |
| 409 | $C_3H_7$ | | chroman-F,F | phenyl | chroman-F,F | | | F |
| 410 | $C_3H_7$ | | chroman-F,F | phenyl | chroman-F,F | | | $CF_3$ |
| 411 | $C_3H_7$ | | chroman-F,F | phenyl | chroman-F,F | | | $OCF_3$ |
| 412 | $C_3H_7$ | | chroman-F,F | phenyl | chroman-F,F | | | CN |
| 413 | $C_5H_{11}$ | | chroman-F,F | phenyl | chroman-F,F | | | F |

TABLE-continued

Further example compounds

| | R¹ | A¹ | A² | W¹ | W² | Z⁴ | A³ | R² |
|---|---|---|---|---|---|---|---|---|
| 414 | C₅H₁₁— | | | | | | | CF₃ |
| 415 | C₅H₁₁— | | | | | | | OCF₃ |
| 416 | C₅H₁₁— | | | | | | | CN |
| 417 | CH₂=CH-CH₃ | | | | | | | F |
| 418 | CH₂=CH-CH₃ | | | | | | | CF₃ |
| 419 | CH₂=CH-CH₃ | | | | | | | OCF₃ |

TABLE-continued
Further example compounds
| | R¹ | A¹ | W¹ | A² | W² | Z⁴ | A³ | R² |
|---|---|---|---|---|---|---|---|---|
| 420 |  | | 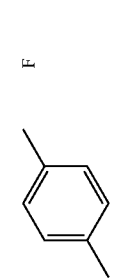 | 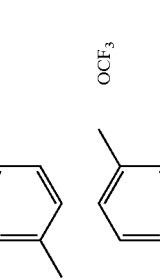 | 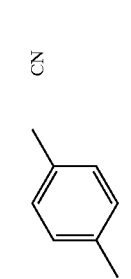 | | | CN |
| 421 | C₃H₇— | | 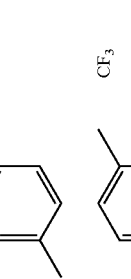 | | 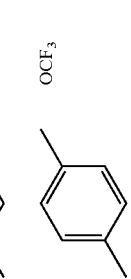 | | 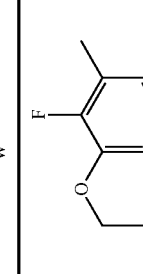 | F |
| 422 | C₃H₇— | | 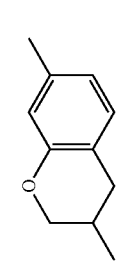 | | 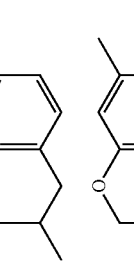 | | 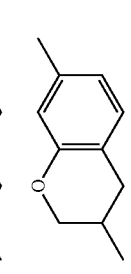 | CF₃ |
| 423 | C₃H₇— | | 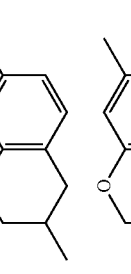 | | 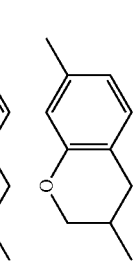 | | 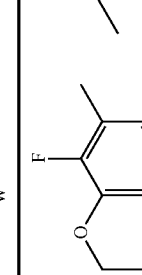 | OCF₃ |
| 424 | C₃H₇— | | 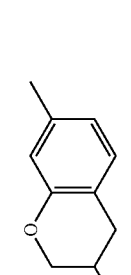 | | 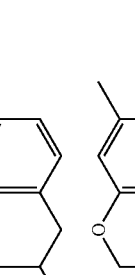 | | 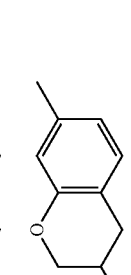 | CN |
| 425 | C₅H₁₁— | | 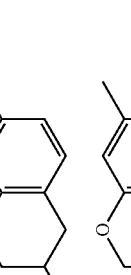 | | 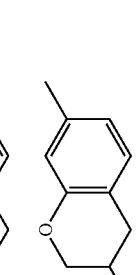 | | 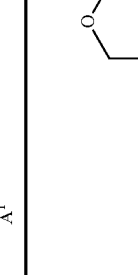 | F |
| 426 | C₅H₁₁— | |  | |  | |  | CF₃ |
| 427 | C₅H₁₁— | |  | | 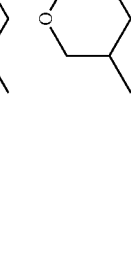 | |  | OCF₃ |

TABLE-continued

Further example compounds

| | R¹ | A¹ | W¹ | A² | W² | Z⁴ | A³ | R² |
|---|---|---|---|---|---|---|---|---|
| 428 | C₅H₁₁— | | chroman-Me | | chroman-Me | | phenyl | CN |
| 429 | isobutenyl | | chroman-Me | | chroman-Me | | phenyl | F |
| 430 | isobutenyl | | chroman-Me | | chroman-Me | | phenyl | CF₃ |
| 431 | isobutenyl | | chroman-Me | | chroman-Me | | phenyl | OCF₃ |
| 432 | isobutenyl | | chroman-Me | | chroman-Me | | phenyl | CN |
| 433 | C₃H₇ | | chroman-Me | | F-chroman-Me | | phenyl | F |
| 434 | C₃H₇ | | chroman-Me | | F-chroman-Me | | phenyl | CF₃ |

TABLE-continued
Further example compounds
| | R¹ | A¹ | W¹ | A² | W² | Z⁴ | A³ | R² |
|---|---|---|---|---|---|---|---|---|
| 435 | C₃H₇ | |  | |  | |  | OCF₃ |
| 436 | C₃H₇ | |  | |  | |  | CN |
| 437 | C₅H₁₁ | |  | |  | |  | F |
| 438 | C₅H₁₁ | |  | |  | |  | CF₃ |
| 439 | C₅H₁₁ | |  | |  | |  | OCF₃ |
| 440 | C₅H₁₁ | |  | |  | |  | CN |
| 441 |  | |  | |  | |  | F |
| 442 |  | |  | |  | |  | CF₃ |

TABLE-continued

Further example compounds

| | R¹ | A¹ | W¹ | A² | W² | Z⁴ | A³ | R² |
|---|---|---|---|---|---|---|---|---|
| 443 | CH₂=C(CH₃)- | | 3-methylchroman | | 6-fluoro-3-methylchroman | | phenylene | OCF₃ |
| 444 | CH₂=C(CH₃)- | | 3-methylchroman | | 6-fluoro-3-methylchroman | | phenylene | CN |
| 445 | C₃H₇ | | 3-methylchroman | | 6,8-difluoro-3-methylchroman | | phenylene | F |
| 446 | C₃H₇ | | 3-methylchroman | | 6,8-difluoro-3-methylchroman | | phenylene | CF₃ |
| 447 | C₃H₇ | | 3-methylchroman | | 6,7,8-trifluoro-3-methylchroman | | phenylene | OCF₃ |
| 448 | C₃H₇ | | 3-methylchroman | | 6,7,8-trifluoro-3-methylchroman | | phenylene | CN |

TABLE-continued
Further example compounds
| | R¹ | A¹ | W¹ | A² | W² | Z⁴ | A³ | R² |
|---|---|---|---|---|---|---|---|---|
| 449 | C₅H₁₁— | | 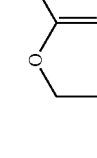 | | 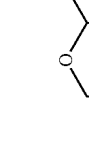 | |  | F |
| 450 | C₅H₁₁— | | 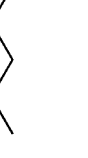 | | 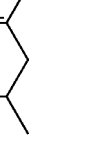 | | 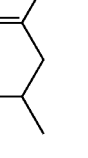 | CF₃ |
| 451 | C₅H₁₁— | | 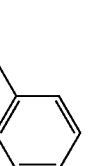 | | 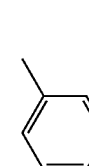 | | 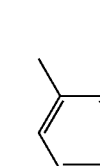 | OCF₃ |
| 452 | C₅H₁₁— | | 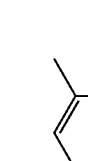 | |  | |  | CN |
| 453 |  | |  | |  | |  | F |
| 454 |  | |  | |  | |  | CF₃ |

TABLE-continued

Further example compounds

| | $R^1$ | $A^1$ | $W^1$ | $A^2$ | $W^2$ | $Z^4$ | $A^3$ | $R^2$ |
|---|---|---|---|---|---|---|---|---|
| 455 | CH=CH(CH₃) | | 3-methyl-6-F-chroman | | 3-methyl-6,8-difluoro-chroman | | phenyl | OCF₃ |
| 456 | CH=CH(CH₃) | | 3-methyl-6-F-chroman | | 3-methyl-6,8-difluoro-chroman | | phenyl | CN |
| 457 | C₃H₇ | | 3-methyl-6-F-chroman | | 3-methyl-chroman | | phenyl | F |
| 458 | C₃H₇ | | 3-methyl-6-F-chroman | | 3-methyl-chroman | | phenyl | CF₃ |
| 459 | C₃H₇ | | 3-methyl-6-F-chroman | | 3-methyl-chroman | | phenyl | OCF₃ |
| 460 | C₃H₇ | | 3-methyl-6-F-chroman | | 3-methyl-chroman | | phenyl | CN |
| 461 | C₅H₁₁ | | 3-methyl-6-F-chroman | | 3-methyl-chroman | | phenyl | F |

TABLE-continued

Further example compounds

| | R¹ | A¹ | W¹ | A² | W² | Z⁴ | A³ | R² |
|---|---|---|---|---|---|---|---|---|
| 462 | C₅H₁₁— | | (fluoro-methylchroman) | | (methylchroman) | | (phenyl) | CF₃ |
| 463 | C₅H₁₁— | | (fluoro-methylchroman) | | (methylchroman) | | (phenyl) | OCF₃ |
| 464 | C₅H₁₁— | | (fluoro-methylchroman) | | (methylchroman) | | (phenyl) | CN |
| 465 | CH₃-CH=CH- | | (fluoro-methylchroman) | | (methylchroman) | | (phenyl) | F |
| 466 | CH₃-CH=CH- | | (fluoro-methylchroman) | | (methylchroman) | | (phenyl) | CF₃ |
| 467 | CH₃-CH=CH- | | (fluoro-methylchroman) | | (methylchroman) | | (phenyl) | OCF₃ |
| 468 | CH₃-CH=CH- | | (fluoro-methylchroman) | | (methylchroman) | | (phenyl) | CN |

TABLE-continued

Further example compounds

| | R¹ | A¹ | W¹ | A² | W² | Z⁴ | A³ | R² |
|---|---|---|---|---|---|---|---|---|
| 469 | C₃H₇— | | chroman-F, methyl | | chroman-F, methyl | | phenyl | F |
| 470 | C₃H₇— | | chroman-F, methyl | | chroman-F, methyl | | phenyl | CF₃ |
| 471 | C₃H₇— | | chroman-F, methyl | | chroman-F, methyl | | phenyl | OCF₃ |
| 472 | C₃H₇— | | chroman-F, methyl | | chroman-F, methyl | | phenyl | CN |
| 473 | C₅H₁₁— | | chroman-F, methyl | | chroman-F, methyl | | phenyl | F |
| 474 | C₅H₁₁— | | chroman-F, methyl | | chroman-F, methyl | | phenyl | CF₃ |
| 475 | C₅H₁₁— | | chroman-F, methyl | | chroman-F, methyl | | phenyl | OCF₃ |
| 476 | C₅H₁₁— | | chroman-F, methyl | | chroman-F, methyl | | phenyl | CN |

TABLE-continued

Further example compounds

| | R¹ | A¹ | W¹ | A² | W² | Z⁴ | A³ | R² |
|---|---|---|---|---|---|---|---|---|
| 477 | CH₂=C(CH₃)- | | 6-F,8-Me-chroman-3-yl | | 6-F,8-Me-chroman-3-yl | | phenyl | F |
| 478 | CH₂=C(CH₃)- | | 6-F,8-Me-chroman-3-yl | | 6-F,8-Me-chroman-3-yl | | phenyl | CF₃ |
| 479 | CH₂=C(CH₃)- | | 6-F,8-Me-chroman-3-yl | | 6-F,8-Me-chroman-3-yl | | phenyl | OCF₃ |
| 480 | CH₂=C(CH₃)- | | 6-F,8-Me-chroman-3-yl | | 6-F,8-Me-chroman-3-yl | | phenyl | CN |
| 481 | C₃H₇- | | 6-F,8-Me-chroman-3-yl | | 6-F,7-Me,8-F-chroman-3-yl | | phenyl | F |
| 482 | C₃H₇- | | 6-F,8-Me-chroman-3-yl | | 6-F,7-Me-chroman-3-yl | | phenyl | CF₃ |

TABLE-continued
Further example compounds
| | $R^1$ | $A^1$ | $W^1$ | $A^2$ | $W^2$ | $Z^4$ | $A^3$ | $R^2$ |
|---|---|---|---|---|---|---|---|---|
| 483 | $C_3H_7$— | | 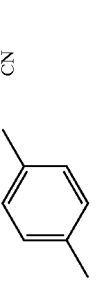 | |  | | 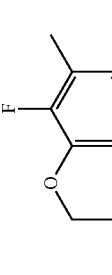 | $OCF_3$ |
| 484 | $C_3H_7$— | | 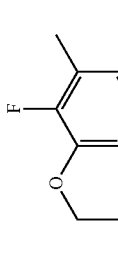 | | 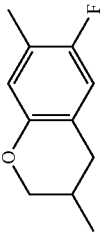 | | 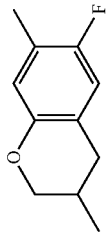 | $CN$ |
| 485 | $C_5H_{11}$— | | 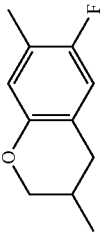 | | 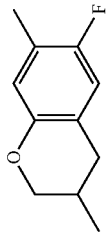 | | 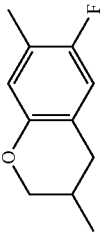 | $F$ |
| 486 | $C_5H_{11}$— | | 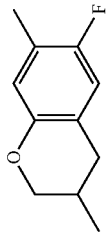 | | 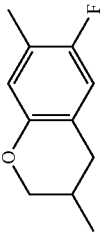 | | 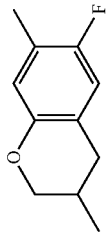 | $CF_3$ |
| 487 | $C_5H_{11}$— | | 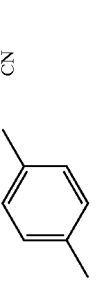 | | 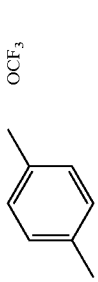 | | 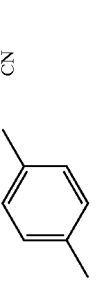 | $OCF_3$ |
| 488 | $C_5H_{11}$— | | | | | | 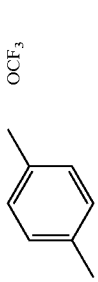 | $CN$ |

TABLE-continued

Further example compounds

| | R¹ | A¹ | W¹ | A² | W² | Z⁴ | A³ | R² |
|---|---|---|---|---|---|---|---|---|
| 489 | CH₂=CH- | | 6-F, 7-Me chroman-3-yl | | 6-F, 7-Me, 8-F chroman-3-yl | | 1,4-phenylene | F |
| 490 | CH₂=CH- | | 6-F, 7-Me chroman-3-yl | | 6-F, 7-Me, 8-F chroman-3-yl | | 1,4-phenylene | CF₃ |
| 491 | CH₂=CH- | | 6-F, 7-Me chroman-3-yl | | 6-F, 7-Me, 8-F chroman-3-yl | | 1,4-phenylene | OCF₃ |
| 492 | CH₂=CH- | | 6-F, 7-Me chroman-3-yl | | 6-F, 7-Me, 8-F chroman-3-yl | | 1,4-phenylene | CN |
| 493 | C₃H₇ | | 6-F, 7-Me, 8-F chroman-3-yl | | 6-F, 7-Me, 8-F chroman-3-yl | | 1,4-phenylene | F |
| 494 | C₃H₇ | | 6-F, 7-Me, 8-F chroman-3-yl | | 6-F, 7-Me, 8-F chroman-3-yl | | 1,4-phenylene | CF₃ |

TABLE-continued

Further example compounds

| | $R^1$ | $A^1$ | $W^1$ | $A^2$ | $W^2$ | $Z^4$ | $A^3$ | $R^2$ |
|---|---|---|---|---|---|---|---|---|
| 495 | $C_3H_7$ | | 3-methyl-7,8-difluorochroman | | 3-methyl-7,8-difluorochroman | | phenyl | $OCF_3$ |
| 496 | $C_3H_7$ | | 3-methyl-7,8-difluorochroman | | 3-methyl-7,8-difluorochroman | | phenyl | CN |
| 497 | $C_5H_{11}$ | | 3-methyl-7,8-difluorochroman | | 3-methyl-7,8-difluorochroman | | phenyl | F |
| 498 | $C_5H_{11}$ | | 3-methyl-7,8-difluorochroman | | 3-methyl-7,8-difluorochroman | | phenyl | $CF_3$ |
| 499 | $C_5H_{11}$ | | 3-methyl-7,8-difluorochroman | | 3-methyl-7,8-difluorochroman | | phenyl | $OCF_3$ |
| 500 | $C_5H_{11}$ | | 3-methyl-7,8-difluorochroman | | 3-methyl-7,8-difluorochroman | | phenyl | CN |

TABLE-continued

Further example compounds

| | R¹ | A¹ | W¹ | A² | W² | Z⁴ | A³ | R² |
|---|---|---|---|---|---|---|---|---|
| 501 | CH₂=C(CH₃)– | | 5,6-difluoro-3-methylchroman | | 5,6-difluoro-3-methylchroman | | p-phenylene | F |
| 502 | CH₂=C(CH₃)– | | 5,6-difluoro-3-methylchroman | | 5,6-difluoro-3-methylchroman | | p-phenylene | CF₃ |
| 503 | CH₂=C(CH₃)– | | 5,6-difluoro-3-methylchroman | | 5,6-difluoro-3-methylchroman | | p-phenylene | OCF₃ |
| 504 | CH₂=C(CH₃)– | | 5,6-difluoro-3-methylchroman | | 5,6-difluoro-3-methylchroman | | p-phenylene | CN |
| 505 | C₃H₇– | | 3-methylchroman | 2-fluoro-4-methylphenylene | 3-methylchroman | | | F |
| 506 | C₃H₇– | | 3-methylchroman | 2-fluoro-6-methylphenylene | 3-methylchroman | | | CF₃ |

TABLE-continued

Further example compounds

| | R¹ | A¹ | W¹ | A² | W² | Z⁴ | A³ | R² |
|---|---|---|---|---|---|---|---|---|
| 507 | C₃H₇— | | chromane-3-methyl | F-dimethylphenyl | chromane-3-methyl | | | OCF₃ |
| 508 | C₃H₇— | | chromane-3-methyl | F-dimethylphenyl | chromane-3-methyl | | | CN |
| 509 | C₅H₁₁— | | chromane-3-methyl | F-dimethylphenyl | chromane-3-methyl | | | F |
| 510 | C₅H₁₁— | | chromane-3-methyl | F-dimethylphenyl | chromane-3-methyl | | | CF₃ |
| 511 | C₅H₁₁— | | chromane-3-methyl | F-dimethylphenyl | chromane-3-methyl | | | OCF₃ |
| 512 | C₅H₁₁— | | chromane-3-methyl | F-dimethylphenyl | chromane-3-methyl | | | CN |

TABLE-continued

Further example compounds

| | R¹ | A¹ | W¹ | A² | W² | Z⁴ | A³ | R² |
|---|---|---|---|---|---|---|---|---|
| 513 | CH₂=C(CH₃)- | | 3-methylchroman | 2-F,5-Me-phenyl | 6-methylchroman | | | F |
| 514 | CH₂=C(CH₃)- | | 3-methylchroman | 2-F,5-Me-phenyl | 6-methylchroman | | | CF₃ |
| 515 | CH₂=C(CH₃)- | | 3-methylchroman | 2-F,5-Me-phenyl | 6-methylchroman | | | OCF₃ |
| 516 | CH₂=C(CH₃)- | | 3-methylchroman | 2-F,5-Me-phenyl | 6-methylchroman | | | CN |
| 517 | C₃H₇ | | 3-methylchroman | 2-F,5-Me-phenyl | 6-F,7-Me-3-methylchroman | | | F |
| 518 | C₃H₇ | | 3-methylchroman | 2-F,5-Me-phenyl | 6-F,7-Me-3-methylchroman | | | CF₃ |

TABLE-continued
Further example compounds
| | R¹ | A¹ | | A² | | W² | Z⁴ | A³ | R² |
|---|---|---|---|---|---|---|---|---|---|
| 519 | C₃H₇ | 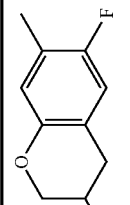 | | 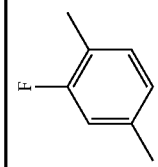 | | 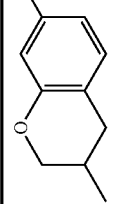 | | | OCF₃ |
| 520 | C₃H₇ |  | | 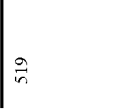 | | 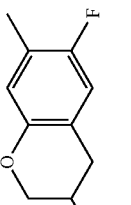 | | | CN |
| 521 | C₅H₁₁ | 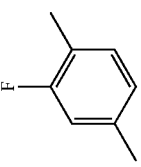 | | 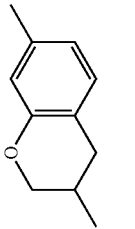 | |  | | | F |
| 522 | C₅H₁₁ |  | | 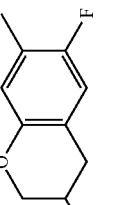 | | 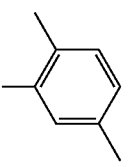 | | | CF₃ |
| 523 | C₅H₁₁ | 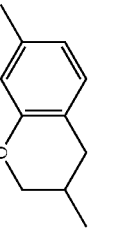 | |  | |  | | | OCF₃ |
| 524 | C₅H₁₁ | 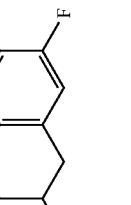 | | 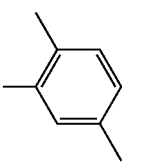 | | 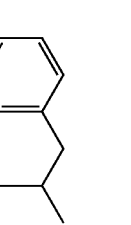 | | | CN |

TABLE-continued
Further example compounds
| | R¹ | A¹ | W¹ | A² | W² | Z⁴ | A³ | R² |
|---|---|---|---|---|---|---|---|---|
| 525 | 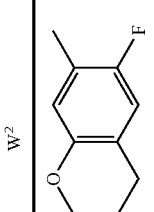 | | 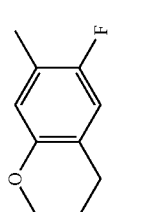 | 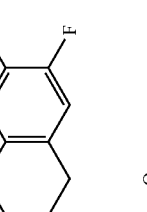 | 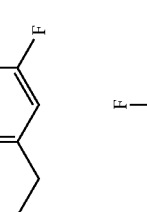 | | | F |
| 526 | 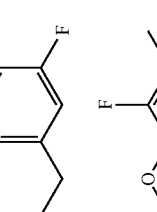 | | 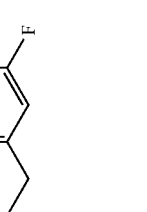 | 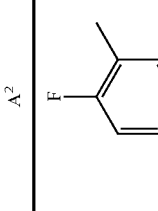 | 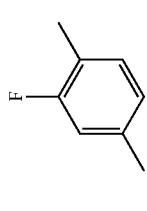 | | | CF₃ |
| 527 | 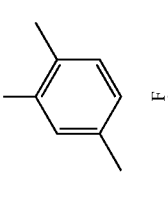 | | 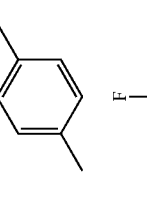 | 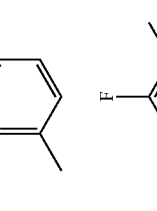 | 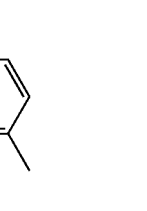 | | | OCF₃ |
| 528 | 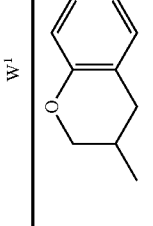 | | 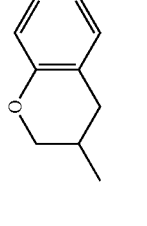 | 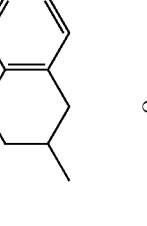 | 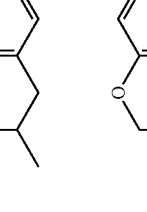 | | | CN |
| 529 | C₃H₇— | | 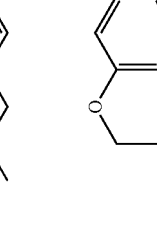 |  | 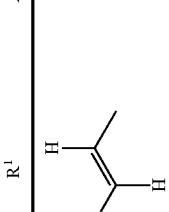 | | | F |
| 530 | C₃H₇— | | 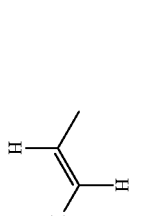 | 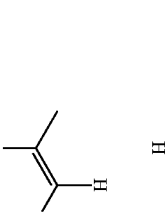 |  | | | CF₃ |

TABLE-continued

Further example compounds

| | R¹ | A¹ / W¹ | A² | W² | Z⁴ | A³ | R² |
|---|---|---|---|---|---|---|---|
| 531 | C₃H₇— | (3-methylchroman) | (F-methylphenyl) | (6,8-difluoro-3-methylchroman) | | | OCF₃ |
| 532 | C₃H₇— | (3-methylchroman) | (F-methylphenyl) | (6,8-difluoro-3-methylchroman) | | | CN |
| 533 | C₅H₁₁— | (3-methylchroman) | (F-methylphenyl) | (6,8-difluoro-3-methylchroman) | | | F |
| 534 | C₅H₁₁— | (3-methylchroman) | (F-methylphenyl) | (6,8-difluoro-3-methylchroman) | | | CF₃ |
| 535 | C₅H₁₁— | (3-methylchroman) | (F-methylphenyl) | (6,8-difluoro-3-methylchroman) | | | OCF₃ |
| 536 | C₅H₁₁— | (3-methylchroman) | (F-methylphenyl) | (6,7-difluoro-3-methylchroman) | | | CN |

TABLE-continued
Further example compounds
| | R¹ | A¹ | W¹ | A² | W² | Z⁴ | A³ | R² |
|---|---|---|---|---|---|---|---|---|
| 537 | 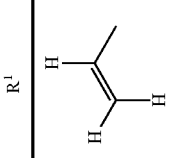 | | 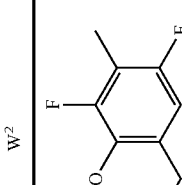 | 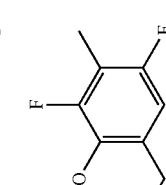 | 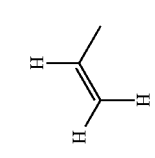 | | | F |
| 538 | 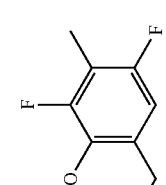 | | 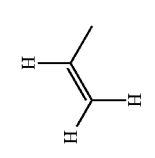 | 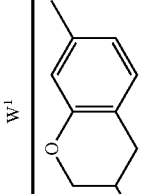 | 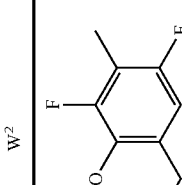 | | | CF₃ |
| 539 | 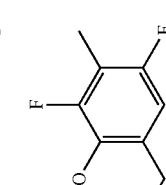 | | 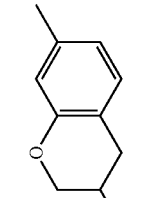 | 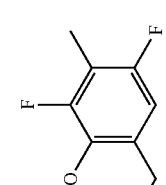 | 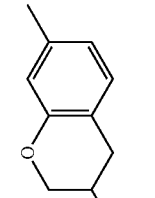 | | | OCF₃ |
| 540 | 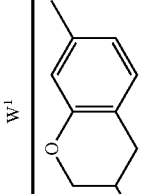 | | 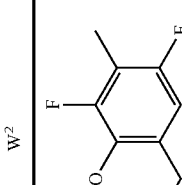 | 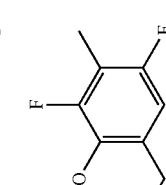 | 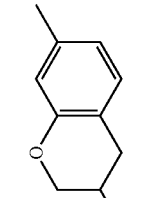 | | | CN |
| 541 | C₃H₇— | | 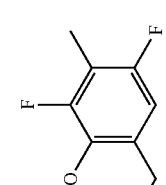 | 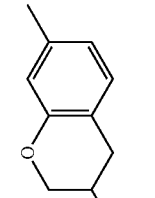 | 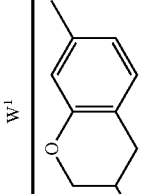 | | | F |
| 542 | C₃H₇— | | 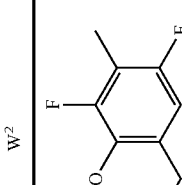 | 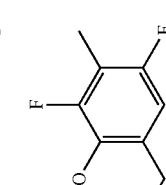 | 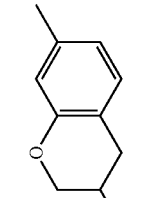 | | | CF₃ |

TABLE-continued

Further example compounds

| | $R^1$ | $A^1$ | $W^1$ | $A^2$ | $W^2$ | $Z^4$ | $A^3$ | $R^2$ |
|---|---|---|---|---|---|---|---|---|
| 543 | $C_3H_7$ | | chroman-F | F-dimethylphenyl | chroman | | | $OCF_3$ |
| 544 | $C_3H_7$ | | chroman-F | F-dimethylphenyl | chroman | | | CN |
| 545 | $C_5H_{11}$ | | chroman-F | F-dimethylphenyl | chroman | | | F |
| 546 | $C_5H_{11}$ | | chroman-F | F-dimethylphenyl | chroman | | | $CF_3$ |
| 547 | $C_5H_{11}$ | | chroman-F | F-dimethylphenyl | chroman | | | $OCF_3$ |
| 548 | $C_5H_{11}$ | | chroman-F | F-dimethylphenyl | chroman | | | CN |

TABLE-continued

Further example compounds

| R¹ | A¹ | W¹ | A² | W² | Z⁴ | A³ | R² |
|---|---|---|---|---|---|---|---|
| 549 | CH=CH₂ (isopropenyl) | | 6-F chromane-3-methyl | 3-F-dimethylphenyl | 7-methyl chromane | | | F |
| 550 | isopropenyl | | 6-F chromane-3-methyl | 3-F-dimethylphenyl | 7-methyl chromane | | | CF₃ |
| 551 | isopropenyl | | 6-F chromane-3-methyl | 3-F-dimethylphenyl | 7-methyl chromane | | | OCF₃ |
| 552 | isopropenyl | | 6-F chromane-3-methyl | 3-F-dimethylphenyl | 7-methyl chromane | | | CN |
| 553 | C₃H₇ | | 6-F chromane-3-methyl | 3-F-dimethylphenyl | 6-F-7-methyl chromane | | | F |
| 554 | C₃H₇ | | 6-F chromane-3-methyl | 3-F-dimethylphenyl | 6-F-7-methyl chromane | | | CF₃ |

TABLE-continued

Further example compounds

| | R¹ | A¹ | W¹ | A² | W² | Z⁴ | A³ | R² |
|---|---|---|---|---|---|---|---|---|
| 555 | C₃H₇— | | chroman-F/Me | F,Me-phenyl | chroman-F/Me | | | OCF₃ |
| 556 | C₃H₇— | | chroman-F/Me | F,Me-phenyl | chroman-F/Me | | | CN |
| 557 | C₅H₁₁— | | chroman-F/Me | F,Me-phenyl | chroman-F/Me | | | F |
| 558 | C₅H₁₁— | | chroman-F/Me | F,Me-phenyl | chroman-F/Me | | | CF₃ |
| 559 | C₅H₁₁— | | chroman-F/Me | F,Me-phenyl | chroman-F/Me | | | OCF₃ |
| 560 | C₅H₁₁— | | chroman-F/Me | F,Me-phenyl | chroman-F/Me | | | CN |

TABLE-continued
Further example compounds
| # | R¹ | A¹ | W¹ | A² | W² | Z⁴ | A³ | R² |
|---|---|---|---|---|---|---|---|---|
| 561 | 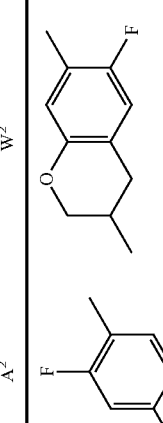 | | 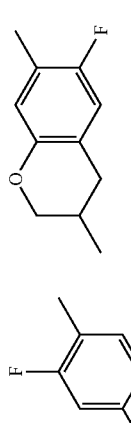 | 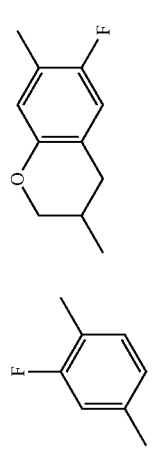 | 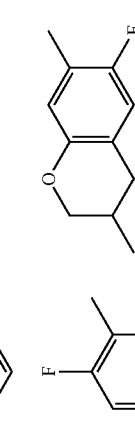 | | | F |
| 562 | 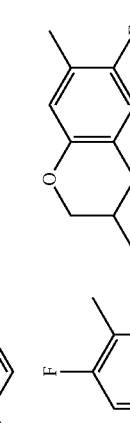 | | | | | | | CF₃ |
| 563 | 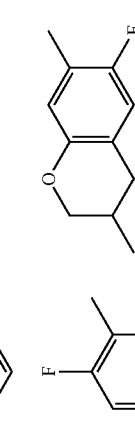 | | | | | | | OCF₃ |
| 564 | 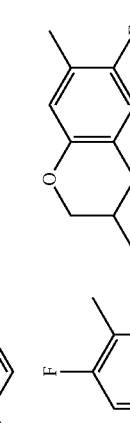 | | | | | | | CN |
| 565 | C₃H₇— | | 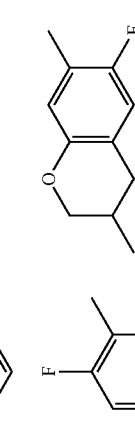 | 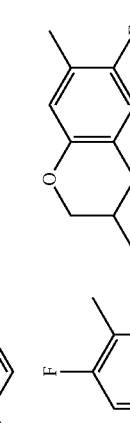 | 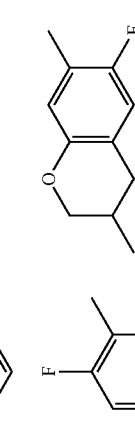 | | | F |
| 566 | C₃H₇— | | 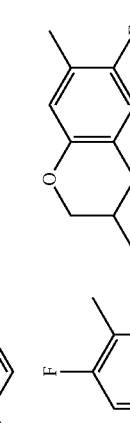 | 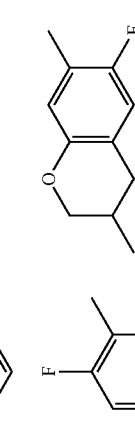 | 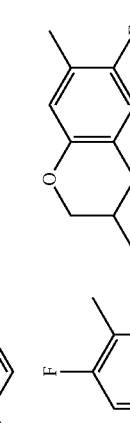 | | | CF₃ |

TABLE-continued

Further example compounds

| | R¹ | A¹ | W¹ | A² | W² | Z⁴ | A³ | R² |
|---|---|---|---|---|---|---|---|---|
| 567 | C₃H₇ | | chroman-3-methyl, 6-F, 7-methyl | 2-F, 5-methyl phenyl | chroman-3-methyl, 6-F, 8-F, 7-methyl | | | OCF₃ |
| 568 | C₃H₇ | | chroman-3-methyl, 6-F, 7-methyl | 2-F, 5-methyl phenyl | chroman-3-methyl, 6-F, 8-F, 7-methyl | | | CN |
| 569 | C₅H₁₁ | | chroman-3-methyl, 6-F, 7-methyl | 2-F, 5-methyl phenyl | chroman-3-methyl, 6-F, 8-F, 7-methyl | | | F |
| 570 | C₅H₁₁ | | chroman-3-methyl, 6-F, 7-methyl | 2-F, 5-methyl phenyl | chroman-3-methyl, 6-F, 8-F, 7-methyl | | | CF₃ |
| 571 | C₅H₁₁ | | chroman-3-methyl, 6-F, 7-methyl | 2-F, 5-methyl phenyl | chroman-3-methyl, 6-F, 8-F, 7-methyl | | | OCF₃ |
| 572 | C₅H₁₁ | | chroman-3-methyl, 6-F, 7-methyl | 2-F, 5-methyl phenyl | chroman-3-methyl, 6-F, 8-F, 7-methyl | | | CN |

TABLE-continued
Further example compounds
| | R$^1$ | A$^1$ | W$^1$ | A$^2$ | W$^2$ | Z$^4$ | A$^3$ | R$^2$ |
|---|---|---|---|---|---|---|---|---|
| 573 | 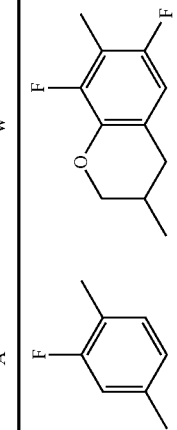 | | 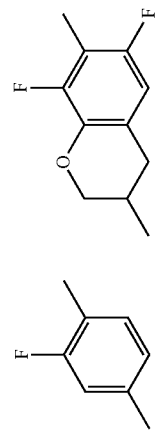 | 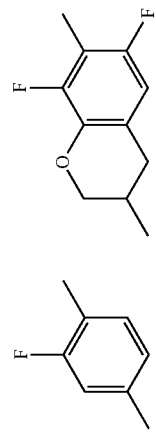 | 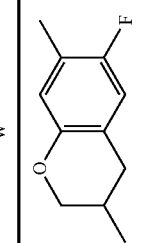 | | | F |
| 574 | 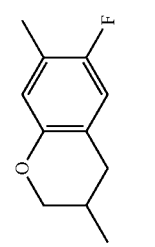 | | 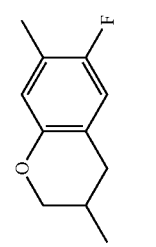 |  |  | | | CF$_3$ |
| 575 |  | |  |  |  | | | OCF$_3$ |
| 576 | 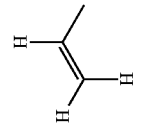 | | | | | | | CN |
| 577 | C$_3$H$_7$— | | | | | | | F |
| 578 | C$_3$H$_7$— | | | | | | | CF$_3$ |
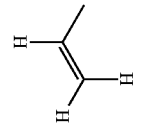

TABLE-continued

Further example compounds

| | $R^1$ | $A^1$ | $W^1$ | $A^2$ | $W^2$ | $Z^4$ | $A^3$ | $R^2$ |
|---|---|---|---|---|---|---|---|---|
| 579 | $C_3H_7-$ | | chroman(F,F,F) | phenyl(F) | chroman(F,F,F) | | | $OCF_3$ |
| 580 | $C_3H_7-$ | | chroman(F,F,F) | phenyl(F) | chroman(F,F,F) | | | CN |
| 581 | $C_5H_{11}-$ | | chroman(F,F,F) | phenyl(F) | chroman(F,F,F) | | | F |
| 582 | $C_5H_{11}-$ | | chroman(F,F,F) | phenyl(F) | chroman(F,F,F) | | | $CF_3$ |
| 583 | $C_5H_{11}-$ | | chroman(F,F,F) | phenyl(F) | chroman(F,F,F) | | | $OCF_3$ |
| 584 | $C_5H_{11}-$ | | chroman(F,F,F) | phenyl(F) | chroman(F,F,F) | | | CN |

TABLE-continued
Further example compounds
| | R¹ | A¹ | A² | W² | Z⁴ | A³ | R² |
|---|---|---|---|---|---|---|---|
| 585 | 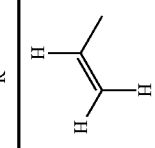 | 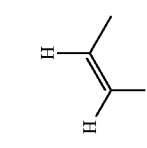 | 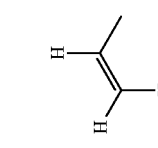 | 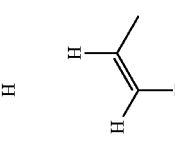 | | | F |
| 586 | 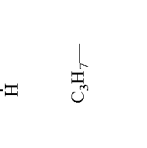 | 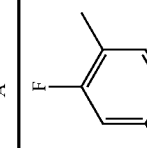 | 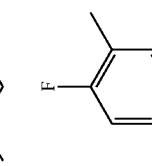 | 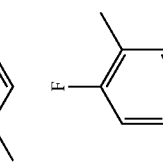 | | | CF₃ |
| 587 | 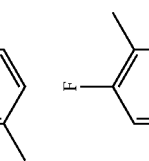 |  | 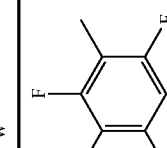 | 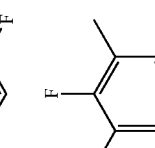 | | | OCF₃ |
| 588 | 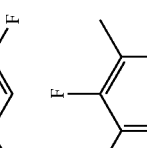 | 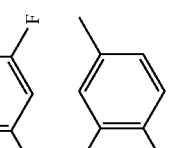 | 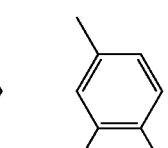 | 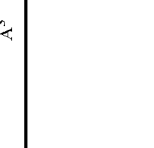 | | | CN |
| 589 | C₃H₇— |  | |  | | 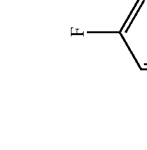 | F |
| 590 | C₃H₇— |  | |  | |  | CF₃ |

TABLE-continued

Further example compounds

| | $R^1$ | $A^1$ | $W^1$ | $A^2$ | $W^2$ | $Z^4$ | $A^3$ | $R^2$ |
|---|---|---|---|---|---|---|---|---|
| 591 | $C_3H_7$— | | 3-methylchroman | | 7-methylchroman | | 2-F-5-Me-phenyl | $OCF_3$ |
| 592 | $C_3H_7$— | | 3-methylchroman | | 7-methylchroman | | 2-F-5-Me-phenyl | CN |
| 593 | $C_5H_{11}$— | | 3-methylchroman | | 7-methylchroman | | 2-F-5-Me-phenyl | F |
| 594 | $C_5H_{11}$— | | 3-methylchroman | | 7-methylchroman | | 2-F-5-Me-phenyl | $CF_3$ |
| 595 | $C_5H_{11}$— | | 3-methylchroman | | 7-methylchroman | | 2-F-5-Me-phenyl | $OCF_3$ |
| 596 | $C_5H_{11}$— | | 3-methylchroman | | 7-methylchroman | | 2-F-5-Me-phenyl | CN |

TABLE-continued

Further example compounds

| | R¹ | A¹ | W¹ | A² | W² | Z⁴ | A³ | R² |
|---|---|---|---|---|---|---|---|---|
| 597 | CH₂=C(CH₃)- | | 3-methylchroman | | 7-methylchroman | | 3-fluoro-4-methylphenyl | F |
| 598 | CH₂=C(CH₃)- | | 3-methylchroman | | 7-methylchroman | | 3-fluoro-4-methylphenyl | CF₃ |
| 599 | CH₂=C(CH₃)- | | 3-methylchroman | | 7-methylchroman | | 3-fluoro-4-methylphenyl | OCF₃ |
| 600 | CH₂=C(CH₃)- | | 3-methylchroman | | 7-methylchroman | | 3-fluoro-4-methylphenyl | CN |
| 601 | C₃H₇— | | 3-methylchroman | | 6-fluoro-7-methylchroman | | 3-fluoro-4-methylphenyl | F |
| 602 | C₃H₇— | | 3-methylchroman | | 6-fluoro-7-methylchroman | | 3-fluoro-4-methylphenyl | CF₃ |

TABLE-continued
Further example compounds
| | $R^1$ | $A^1$ | $W^1$ | $A^2$ | $W^2$ | $Z^4$ | $A^3$ | $R^2$ |
|---|---|---|---|---|---|---|---|---|
| 603 | $C_3H_7$— | | 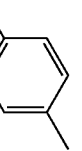 | | 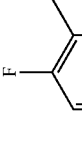 | | 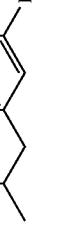 | $OCF_3$ |
| 604 | $C_3H_7$— | | | | | | | CN |
| 605 | $C_5H_{11}$— | | | | | | | F |
| 606 | $C_5H_{11}$— | | | | | | | $CF_3$ |
| 607 | $C_5H_{11}$— | | | | | | | $OCF_3$ |
| 608 | $C_5H_{11}$— | | | | | | | CN |

TABLE-continued
Further example compounds
| R¹ | A¹ W¹ | A² W² | Z⁴ A³ | R² |
|---|---|---|---|---|
| 609 | 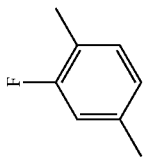 | 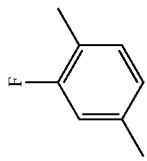 | 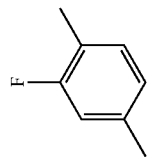 | F |
| 610 | 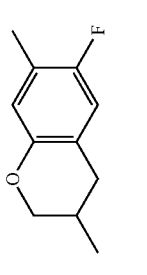 | 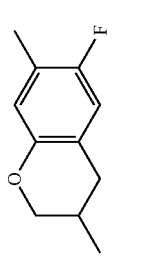 | 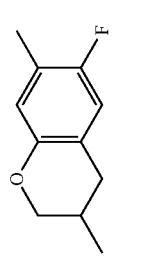 | CF₃ |
| 611 | 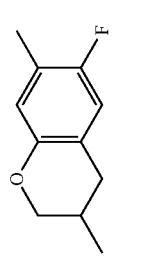 | 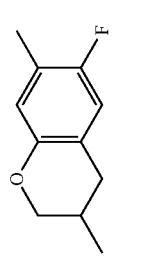 | 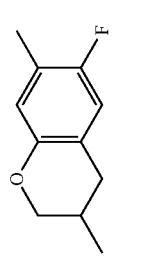 | OCF₃ |
| 612 | 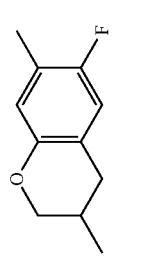 | 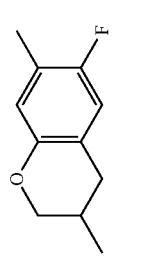 | 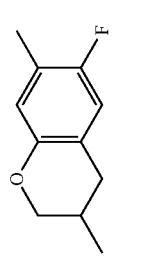 | CN |
| 613 | C₃H₇— | 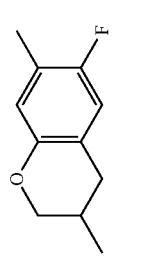 | | F |
| 614 | C₃H₇— | 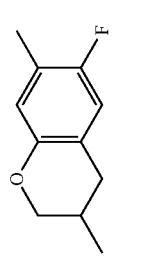 | | CF₃ |

TABLE-continued
Further example compounds
| | R¹ | A¹ | W¹ | A² | W² | Z⁴ | A³ | R² |
|---|---|---|---|---|---|---|---|---|
| 615 | C₃H₇— | | 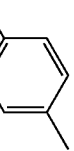 | | 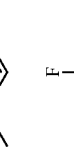 | | 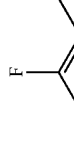 | OCF₃ |
| 616 | C₃H₇— | | 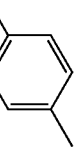 | | 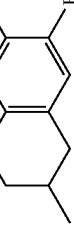 | | 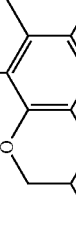 | CN |
| 617 | C₅H₁₁— | |  | | 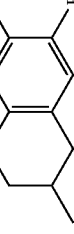 | | 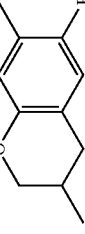 | F |
| 618 | C₅H₁₁— | | | | | | | CF₃ |
| 619 | C₅H₁₁— | | | | | | | OCF₃ |
| 620 | C₅H₁₁— | | | | | | | CN |

TABLE-continued

Further example compounds

| | R¹ | A¹ | W¹ | A² | W² | Z⁴ | A³ | R² |
|---|---|---|---|---|---|---|---|---|
| 621 | isobutenyl | | 3-methylchroman-7-yl | | 3-methyl-5,8-difluorochroman-6-yl | | 3-fluoro-4-methylphenyl | F |
| 622 | isobutenyl | | 3-methylchroman-7-yl | | 3-methyl-5,8-difluorochroman-6-yl | | 3-fluoro-4-methylphenyl | CF₃ |
| 623 | isobutenyl | | 3-methylchroman-7-yl | | 3-methyl-5,8-difluorochroman-6-yl | | 3-fluoro-4-methylphenyl | OCF₃ |
| 624 | isobutenyl | | 3-methylchroman-7-yl | | 3-methyl-5,8-difluorochroman-6-yl | | 3-fluoro-4-methylphenyl | CN |
| 625 | C₃H₇ | | 3-methyl-6-fluorochroman-7-yl | | 3-methylchroman-6-yl | | 3-fluoro-4-methylphenyl | F |
| 626 | C₃H₇ | | 3-methyl-6-fluorochroman-7-yl | | 3-methylchroman-6-yl | | 3-fluoro-4-methylphenyl | CF₃ |

TABLE-continued
Further example compounds
| | R¹ | A¹ | W¹ | A² | W² | Z⁴ | A³ | R² |
|---|---|---|---|---|---|---|---|---|
| 627 | C₃H₇ | |  | | 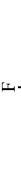 | | 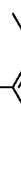 | OCF₃ |
| 628 | C₃H₇ | |  | |  | |  | CN |
| 629 | C₅H₁₁ | |  | |  | |  | F |
| 630 | C₅H₁₁ | |  | |  | |  | CF₃ |
| 631 | C₅H₁₁ | |  | |  | |  | OCF₃ |
| 632 | C₅H₁₁ | |  | |  | |  | CN |

TABLE-continued

Further example compounds

| R¹ | A¹ | W¹ | A² | W² | Z⁴ | A³ | R² |
|---|---|---|---|---|---|---|---|
| 633 | CH₂=C(CH₃)– | | chromanyl-F,CH₃ | | chromanyl-CH₃ | | difluoro-dimethylphenyl | F |
| 634 | CH₂=C(CH₃)– | | chromanyl-F,CH₃ | | chromanyl-CH₃ | | difluoro-dimethylphenyl | CF₃ |
| 635 | CH₂=C(CH₃)– | | chromanyl-F,CH₃ | | chromanyl-CH₃ | | difluoro-dimethylphenyl | OCF₃ |
| 636 | CH₂=C(CH₃)– | | chromanyl-F,CH₃ | | chromanyl-CH₃ | | difluoro-dimethylphenyl | CN |
| 637 | C₃H₇ | | chromanyl-F,CH₃ | | chromanyl-F,CH₃ | | difluoro-dimethylphenyl | F |
| 638 | C₃H₇ | | chromanyl-F,CH₃ | | chromanyl-F,CH₃ | | difluoro-dimethylphenyl | CF₃ |

TABLE-continued

Further example compounds

| | R¹ | A¹ | W¹ | A² | W² | Z⁴ | A³ | R² |
|---|---|---|---|---|---|---|---|---|
| 639 | C₃H₇— | | chromanyl-F,Me | | chromanyl-F,Me | | F,Me-phenyl | OCF₃ |
| 640 | C₃H₇— | | chromanyl-F,Me | | chromanyl-F,Me | | F,Me-phenyl | CN |
| 641 | C₅H₁₁— | | chromanyl-F,Me | | chromanyl-F,Me | | F,Me-phenyl | F |
| 642 | C₅H₁₁— | | chromanyl-F,Me | | chromanyl-F,Me | | F,Me-phenyl | CF₃ |
| 643 | C₅H₁₁— | | chromanyl-F,Me | | chromanyl-F,Me | | F,Me-phenyl | OCF₃ |
| 644 | C₅H₁₁— | | chromanyl-F,Me | | chromanyl-F,Me | | F,Me-phenyl | CN |

TABLE-continued
Further example compounds
| | R¹ | A¹ | W¹ | A² | W² | Z⁴ | A³ | R² |
|---|---|---|---|---|---|---|---|---|
| 645 | 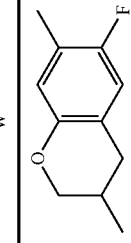 | | 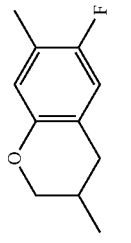 | | 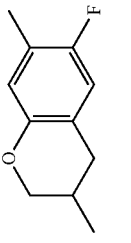 | | 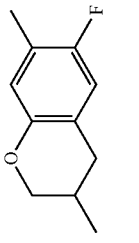 | F |
| 646 | 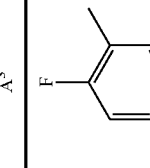 | | 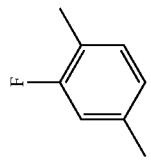 | | 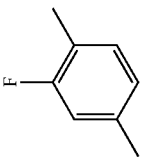 | | 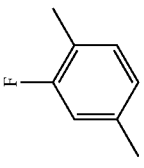 | CF₃ |
| 647 | 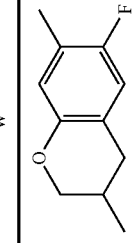 | | 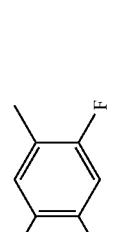 | | 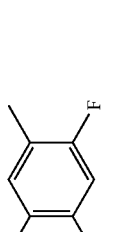 | | 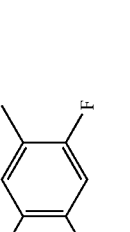 | OCF₃ |
| 648 | 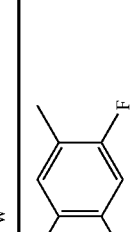 | | 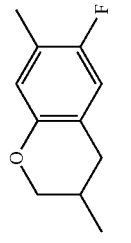 | | 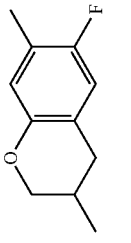 | | 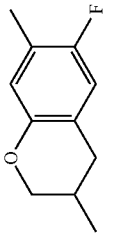 | CN |
| 649 | C₃H₇— | |  | |  | |  | F |
| 650 | C₃H₇— | |  | |  | |  | CF₃ |

TABLE-continued
Further example compounds
| | R¹ | A¹ | W¹ | A² | W² | Z⁴ | A³ | R² |
|---|---|---|---|---|---|---|---|---|
| 651 | $C_3H_7$ | |  | | 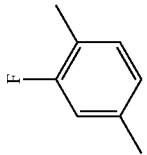 | | 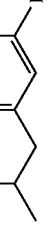 | $OCF_3$ |
| 652 | $C_3H_7$ | | 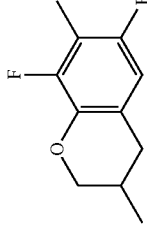 | |  | | 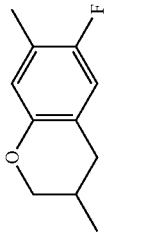 | CN |
| 653 | $C_5H_{11}$ | |  | | 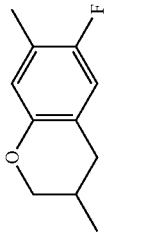 | |  | F |
| 654 | $C_5H_{11}$ | | 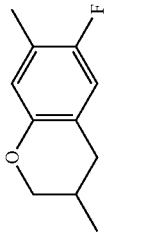 | |  | | 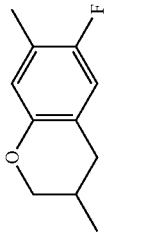 | $CF_3$ |
| 655 | $C_5H_{11}$ | | | | | | | $OCF_3$ |
| 656 | $C_5H_{11}$ | | | | | | | CN |

TABLE-continued

Further example compounds

| | R¹ | A¹ | W¹ | A² | W² | Z⁴ | A³ | R² |
|---|---|---|---|---|---|---|---|---|
| 657 | CH=C(CH₃)H | | 3-methylchroman (6,7-F,CH₃) | | 3-methylchroman (7,8-F,CH₃) | | 2-F-4-methylphenyl | F |
| 658 | CH=C(CH₃)H | | 3-methylchroman (6,7-F,CH₃) | | 3-methylchroman (7,8-F,CH₃) | | 2-F-4-methylphenyl | CF₃ |
| 659 | CH=C(CH₃)H | | 3-methylchroman (6,7-F,CH₃) | | 3-methylchroman (7,8-F,CH₃) | | 2-F-4-methylphenyl | OCF₃ |
| 660 | CH=C(CH₃)H | | 3-methylchroman (6,7-F,CH₃) | | 3-methylchroman (7,8-F,CH₃) | | 2-F-4-methylphenyl | CN |
| 661 | C₃H₇ | | 3-methylchroman (6,7,8-F,CH₃) | | 3-methylchroman (6,7,8-F,CH₃) | | 2-F-4-methylphenyl | F |
| 662 | C₃H₇ | | 3-methylchroman (6,7,8-F,CH₃) | | 3-methylchroman (6,7,8-F,CH₃) | | 2-F-4-methylphenyl | CF₃ |

TABLE-continued

Further example compounds

| | $R^1$ | $A^1$ | $W^1$ | $A^2$ | $W^2$ | $Z^4$ | $A^3$ | $R^2$ |
|---|---|---|---|---|---|---|---|---|
| 663 | $C_3H_7$— | | chroman-F,F,CH3 | | chroman-F,F,CH3 | | 2-F-5-Me-phenyl | $OCF_3$ |
| 664 | $C_3H_7$— | | chroman-F,F,CH3 | | chroman-F,F,CH3 | | 2-F-5-Me-phenyl | CN |
| 665 | $C_5H_{11}$— | | chroman-F,F,CH3 | | chroman-F,F,CH3 | | 2-F-5-Me-phenyl | F |
| 666 | $C_5H_{11}$— | | chroman-F,F,CH3 | | chroman-F,F,CH3 | | 2-F-5-Me-phenyl | $CF_3$ |
| 667 | $C_5H_{11}$— | | chroman-F,F,CH3 | | chroman-F,F,CH3 | | 2-F-5-Me-phenyl | $OCF_3$ |
| 668 | $C_5H_{11}$— | | chroman-F,F,CH3 | | chroman-F,F,CH3 | | 2-F-5-Me-phenyl | CN |

TABLE-continued

Further example compounds

| | R¹ | A¹ | W¹ | A² | W² | Z⁴ | A³ | R² |
|---|---|---|---|---|---|---|---|---|
| 669 | CH=CH-CH₃ | | chroman-F,F | | chroman-F,F | | 2-F-phenyl | F |
| 670 | CH=CH-CH₃ | | chroman-F,F | | chroman-F,F | | 2-F-phenyl | CF₃ |
| 671 | CH=CH-CH₃ | | chroman-F,F | | chroman-F,F | | 2-F-phenyl | OCF₃ |
| 672 | CH=CH-CH₃ | | chroman-F,F | | chroman-F,F | | 2-F-phenyl | CN |
| 673 | C₃H₇ | dioxane | chroman | | chroman | | | F |
| 674 | C₃H₇ | dioxane | chroman | | chroman | | | CF₃ |
| 675 | C₃H₇ | dioxane | chroman | | chroman | | | OCF₃ |

TABLE-continued
Further example compounds
| | R¹ | A¹ | W¹ | A² | W² | Z⁴ | A³ | R² |
|---|---|---|---|---|---|---|---|---|
| 676 | C₃H₇— | 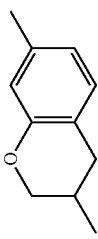 | 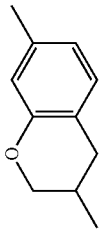 | | 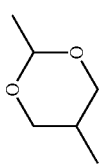 | | | CN |
| 677 | C₅H₁₁— | 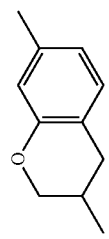 | 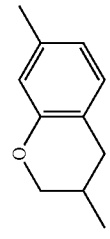 | | 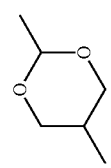 | | | F |
| 678 | C₅H₁₁— | 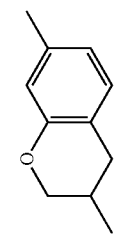 | 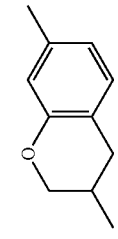 | | 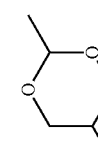 | | | CF₃ |
| 679 | C₅H₁₁— | 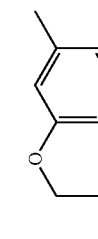 | 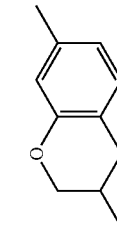 | | 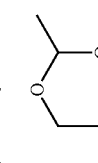 | | | OCF₃ |
| 680 | C₅H₁₁— | 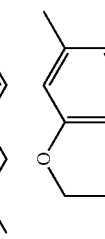 | 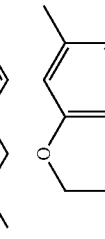 | | 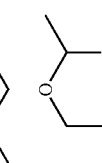 | | | CN |
| 681 | 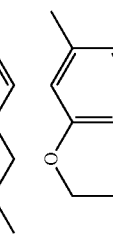 | 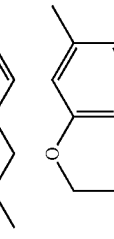 | | 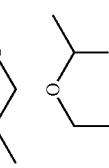 | | | | F |
| 682 | 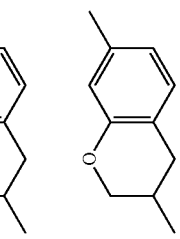 | 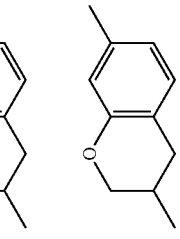 | | 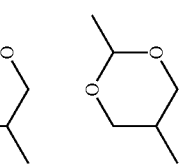 | | | | CF₃ |

TABLE-continued
Further example compounds
| | R¹ | A¹ | W¹ | A² | W² | Z⁴ | A³ | R² |
|---|---|---|---|---|---|---|---|---|
| 683 | CH₂=C(CH₃)– |  |  | |  | | | OCF₃ |
| 684 | CH₂=C(CH₃)– |  |  | |  | | | CN |
| 685 | C₃H₇– |  |  | |  | | | F |
| 686 | C₃H₇– |  |  | |  | | | CF₃ |
| 687 | C₃H₇– |  |  | |  | | | OCF₃ |
| 688 | C₃H₇– |  |  | |  | | | CN |
| 689 | C₅H₁₁– |  |  | |  | | | F |
| 690 | C₅H₁₁– |  |  | |  | | | CF₃ |

TABLE-continued
Further example compounds
| | R¹ | A¹ | W¹ | A² | W² | Z⁴ | A³ | R² |
|---|---|---|---|---|---|---|---|---|
| 691 | C₅H₁₁— | 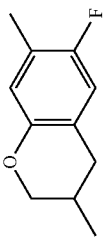 | 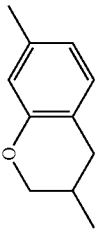 | |  | | | OCF₃ |
| 692 | C₅H₁₁— | 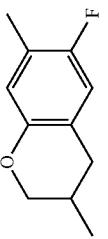 | 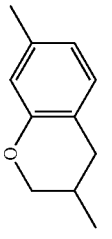 | |  | | | CN |
| 693 |  | 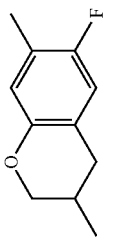 | 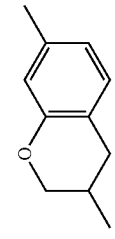 | |  | | | F |
| 694 |  | 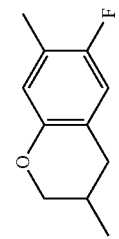 | 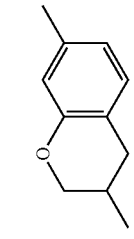 | |  | | | CF₃ |
| 695 |  | 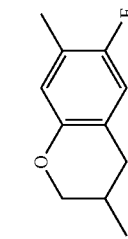 | 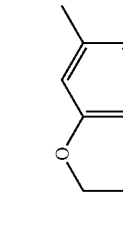 | |  | | | OCF₃ |
| 696 |  | 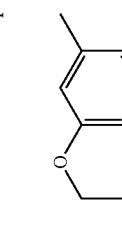 |  | |  | | | CN |
| 697 | C₃H₇— | 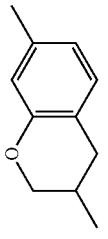 |  | |  | | | F |

TABLE-continued

Further example compounds

| | R¹ | A¹ | W¹ | A² | W² | Z⁴ | A³ | R² |
|---|---|---|---|---|---|---|---|---|
| 698 | C₃H₇ | (2-methyl-5-methyl-1,3-dioxane) | (3-methylchroman, 7-methyl) | | (3-methylchroman, 6,8-difluoro) | | | CF₃ |
| 699 | C₃H₇ | (2-methyl-5-methyl-1,3-dioxane) | (3-methylchroman, 7-methyl) | | (3-methylchroman, 6,8-difluoro) | | | OCF₃ |
| 700 | C₃H₇ | (2-methyl-5-methyl-1,3-dioxane) | (3-methylchroman, 7-methyl) | | (3-methylchroman, 6,8-difluoro) | | | CN |
| 701 | C₅H₁₁ | (2-methyl-5-methyl-1,3-dioxane) | (3-methylchroman, 7-methyl) | | (3-methylchroman, 6,8-difluoro) | | | F |
| 702 | C₅H₁₁ | (2-methyl-5-methyl-1,3-dioxane) | (3-methylchroman, 7-methyl) | | (3-methylchroman, 6,8-difluoro) | | | CF₃ |
| 703 | C₅H₁₁ | (2-methyl-5-methyl-1,3-dioxane) | (3-methylchroman, 7-methyl) | | (3-methylchroman, 6,8-difluoro) | | | OCF₃ |

TABLE-continued

Further example compounds

| | R¹ | A¹ | W¹ | A² | W² | Z⁴ | A³ | R² |
|---|---|---|---|---|---|---|---|---|
| 704 | C₅H₁₁— | [2-Me-1,3-dioxan-5-yl, Me] | [3-methylchroman-6-yl, 7-Me] | | [3-methyl-5,8-difluorochroman-6-yl, 7-Me] | | | CN |
| 705 | isobutenyl (CH₂=C(CH₃)–) | [2-Me-1,3-dioxan-5-yl, Me] | [3-methylchroman-6-yl, 7-Me] | | [3-methyl-5,8-difluorochroman-6-yl, 7-Me] | | | F |
| 706 | isobutenyl | [2-Me-1,3-dioxan-5-yl, Me] | [3-methylchroman-6-yl, 7-Me] | | [3-methyl-5,8-difluorochroman-6-yl, 7-Me] | | | CF₃ |
| 707 | isobutenyl | [2-Me-1,3-dioxan-5-yl, Me] | [3-methylchroman-6-yl, 7-Me] | | [3-methyl-5,8-difluorochroman-6-yl, 7-Me] | | | OCF₃ |
| 708 | isobutenyl | [2-Me-1,3-dioxan-5-yl, Me] | [3-methylchroman-6-yl, 7-Me] | | [3-methyl-8-fluorochroman-6-yl, 7-Me] | | | CN |
| 709 | C₃H₇— | [2-Me-1,3-dioxan-5-yl, Me] | [3-methyl-6-fluorochroman-7-yl, Me] | | [3-methylchroman-6-yl, 7-Me] | | | F |

TABLE-continued
Further example compounds
| | $R^1$ | $A^1$ | $W^1$ | $A^2$ | $W^2$ | $Z^4$ | $A^3$ | $R^2$ |
|---|---|---|---|---|---|---|---|---|
| 710 | $C_3H_7$ | 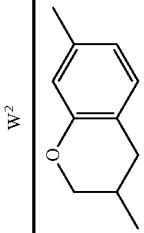 | 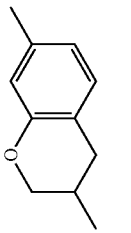 | | 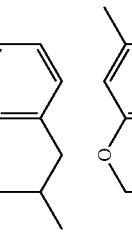 | | | $CF_3$ |
| 711 | $C_3H_7$ | 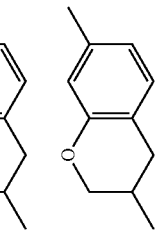 | 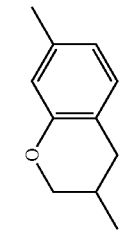 | | 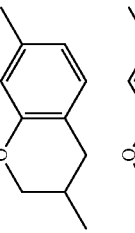 | | | $OCF_3$ |
| 712 | $C_3H_7$ | 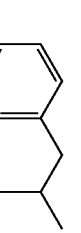 | 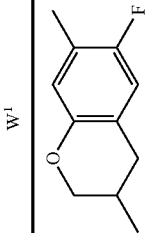 | | 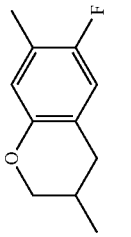 | | | CN |
| 713 | $C_5H_{11}$ | 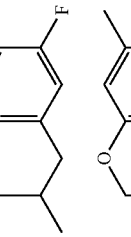 | 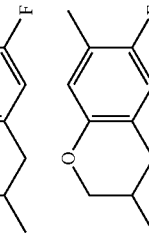 | | 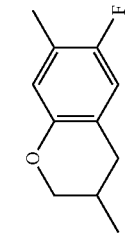 | | | F |
| 714 | $C_5H_{11}$ | 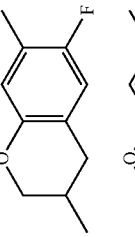 | 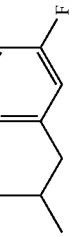 | | 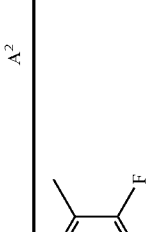 | | | $CF_3$ |
| 715 | $C_5H_{11}$ |  |  | |  | | | $OCF_3$ |
| 716 | $C_5H_{11}$ |  |  | |  | | | CN |
| 717 | 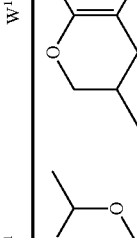 | 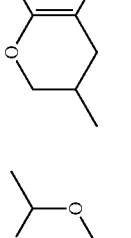 | 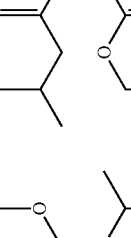 | | 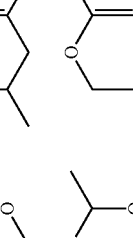 | | | F |

TABLE-continued

Further example compounds

| | R¹ | A¹ | W¹ | A² | W² | Z⁴ | A³ | R² |
|---|---|---|---|---|---|---|---|---|
| 718 | isobutenyl | 4-methyl-1,3-dioxan-2-yl | 6-F-3-methylchroman | | 7-methylchroman | | | CF₃ |
| 719 | isobutenyl | 4-methyl-1,3-dioxan-2-yl | 6-F-3-methylchroman | | 7-methylchroman | | | OCF₃ |
| 720 | isobutenyl | 4-methyl-1,3-dioxan-2-yl | 6-F-3-methylchroman | | 7-methylchroman | | | CN |
| 721 | C₃H₇ | 4-methyl-1,3-dioxan-2-yl | 6-F-3-methylchroman | | 6-F-7-methylchroman | | | F |
| 722 | C₃H₇ | 4-methyl-1,3-dioxan-2-yl | 6-F-3-methylchroman | | 6-F-7-methylchroman | | | CF₃ |
| 723 | C₃H₇ | 4-methyl-1,3-dioxan-2-yl | 6-F-3-methylchroman | | 6-F-7-methylchroman | | | OCF₃ |
| 724 | C₃H₇ | 4-methyl-1,3-dioxan-2-yl | 6-F-3-methylchroman | | 6-F-7-methylchroman | | | CN |

TABLE-continued
Further example compounds
| | R¹ | A¹ | W¹ | A² | W² | Z⁴ | A³ | R² |
|---|---|---|---|---|---|---|---|---|
| 725 | C₅H₁₁— | 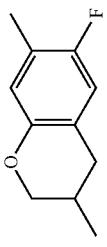 | 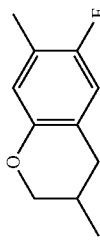 | | 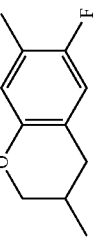 | | | F |
| 726 | C₅H₁₁— | 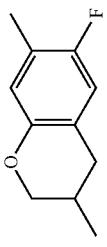 | 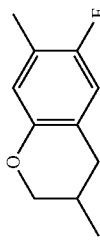 | | 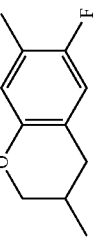 | | | CF₃ |
| 727 | C₅H₁₁— | 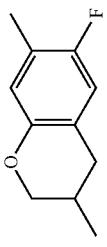 | 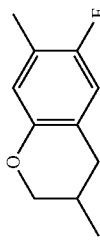 | | 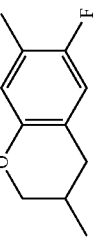 | | | OCF₃ |
| 728 | C₅H₁₁— | 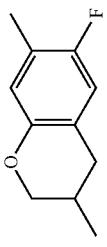 | 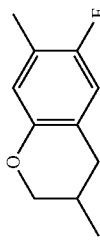 | | 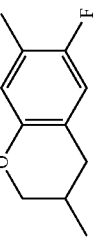 | | | CN |
| 729 | 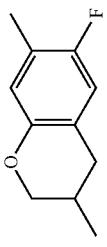 | 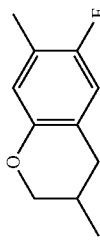 | 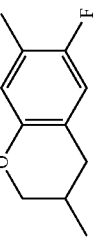 | | 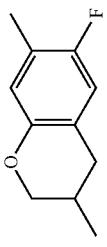 | | | F |
| 730 | 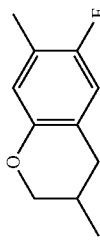 | 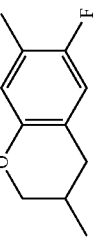 | 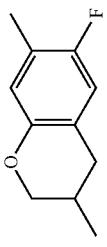 | | 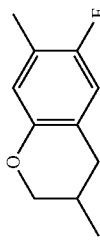 | | | CF₃ |
| 731 | 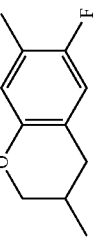 | | | | | | | OCF₃ |

TABLE-continued

Further example compounds

| R¹ | A¹ | W¹ | A² | W² | Z⁴ | A³ | R² |
|---|---|---|---|---|---|---|---|
| 732 | CH₂=C(CH₃)– (isobutenyl, H,H,CH₃,H) | 2-methyl-5-methyl-1,3-dioxane | 3-methyl-6-F-7-methyl chroman | | 3-methyl-7-methyl-8-F-6-F chroman | | CN |
| 733 | C₃H₇ | 2-methyl-5-methyl-1,3-dioxane | 3-methyl-6-F-7-methyl chroman | | 3-methyl-7-methyl-8-F-6-F chroman | | F |
| 734 | C₃H₇ | 2-methyl-5-methyl-1,3-dioxane | 3-methyl-6-F-7-methyl chroman | | 3-methyl-7-methyl-8-F-6-F chroman | | CF₃ |
| 735 | C₃H₇ | 2-methyl-5-methyl-1,3-dioxane | 3-methyl-6-F-7-methyl chroman | | 3-methyl-7-methyl-8-F-6-F chroman | | OCF₃ |
| 736 | C₃H₇ | 2-methyl-5-methyl-1,3-dioxane | 3-methyl-6-F-7-methyl chroman | | 3-methyl-7-methyl-8-F-6-F chroman | | CN |
| 737 | C₅H₁₁ | 2-methyl-5-methyl-1,3-dioxane | 3-methyl-6-F-7-methyl chroman | | 3-methyl-7-methyl-8-F-6-F chroman | | F |

TABLE-continued

Further example compounds

| | R¹ | A¹ | W¹ | A² | W² | Z⁴ | A³ | R² |
|---|---|---|---|---|---|---|---|---|
| 738 | C₅H₁₁— | | | | | | | CF₃ |
| 739 | C₅H₁₁— | | | | | | | OCF₃ |
| 740 | C₅H₁₁— | | | | | | | CN |
| 741 | CH₃CH=CH— | | | | | | | F |
| 742 | CH₃CH=CH— | | | | | | | CF₃ |
| 743 | CH₃CH=CH— | | | | | | | OCF₃ |

TABLE-continued

Further example compounds

| | R¹ | A¹ | W¹ | A² | W² | Z⁴ | A³ | R² |
|---|---|---|---|---|---|---|---|---|
| 744 | CH₂=C(H)- (isobutenyl-like) | dioxane-Me | chroman-F,F,Me | | chroman-F,F,Me | | | CN |
| 745 | C₃H₇— | dioxane-Me | chroman-F,F,Me | | chroman-F,F,Me | | | F |
| 746 | C₃H₇— | dioxane-Me | chroman-F,F,Me | | chroman-F,F,Me | | | CF₃ |
| 747 | C₃H₇— | dioxane-Me | chroman-F,F,Me | | chroman-F,F,Me | | | OCF₃ |
| 748 | C₃H₇— | dioxane-Me | chroman-F,F,Me | | chroman-F,F,Me | | | CN |
| 749 | C₅H₁₁— | dioxane-Me | chroman-F,F,Me | | chroman-F,F,Me | | | F |

TABLE-continued
Further example compounds
| | R¹ | A¹ | W¹ | A² | W² | Z⁴ | A³ | R² |
|---|---|---|---|---|---|---|---|---|
| 750 | C₅H₁₁— | 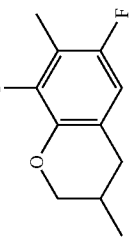 | 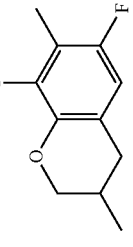 | |  | | | CF₃ |
| 751 | C₅H₁₁— | 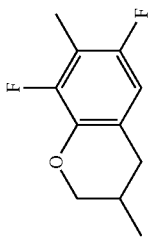 | 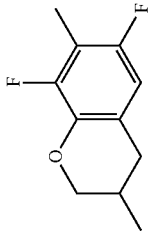 | |  | | | OCF₃ |
| 752 | C₅H₁₁— | 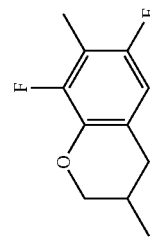 | 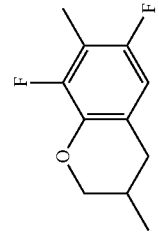 | |  | | | CN |
| 753 |  | 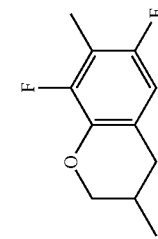 | 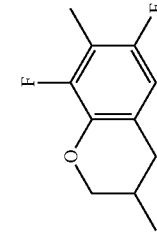 | |  | | | F |
| 754 |  | 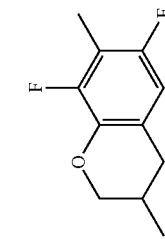 | 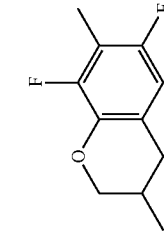 | |  | | | CF₃ |
| 755 |  | 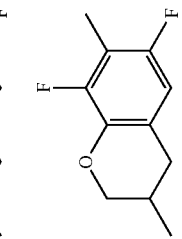 | 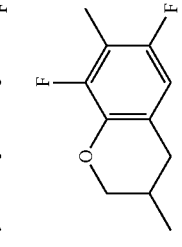 | |  | | | OCF₃ |

TABLE-continued

Further example compounds

| # | R¹ | A¹ | W¹ | A² | W² | Z⁴ | A³ | R² |
|---|---|---|---|---|---|---|---|---|
| 756 | CH=CH₂ (propenyl) | 2,5-dimethyl-1,3-dioxane | 3-methyl-6,8-difluorochroman | | 3-methyl-6,8-difluorochroman | C(CF₃)(F)OCH₃ | 3,5-difluoro-4-methylphenyl | CN |
| 757 | C₃H₇ | | 3-methylchroman | | 3-methylchroman | C(CF₃)(F)OCH₃ | 3,5-difluoro-4-methylphenyl | F |
| 758 | C₃H₇ | | 3-methylchroman | | 3-methylchroman | C(CF₃)(F)OCH₃ | 3,5-difluorophenyl | CF₃ |
| 759 | C₃H₇ | | 3-methylchroman | | 3-methylchroman | C(CF₃)(F)OCH₃ | 3,5-difluorophenyl | OCF₃ |
| 760 | C₃H₇ | | 3-methylchroman | | 3-methylchroman | C(CF₃)(F)OCH₃ | 3,5-difluorophenyl | CN |
| 761 | C₅H₁₁ | | 3-methylchroman | | 3-methylchroman | C(CF₃)(F)OCH₃ | 3,5-difluorophenyl | F |

TABLE-continued

Further example compounds

| | R¹ | A¹ | W¹ | A² | W² | Z⁴ | A³ | R² |
|---|---|---|---|---|---|---|---|---|
| 762 | C₅H₁₁— | | chromane-methyl | | chromane-methyl | OC(CF₃)₂ | difluoromethylphenyl | CF₃ |
| 763 | C₅H₁₁— | | chromane-methyl | | chromane-methyl | OC(CF₃)₂ | difluoromethylphenyl | OCF₃ |
| 764 | C₅H₁₁— | | chromane-methyl | | chromane-methyl | OC(CF₃)₂ | difluoromethylphenyl | CN |
| 765 | CH₂=CH— | | chromane-methyl | | chromane-methyl | OC(CF₃)₂ | difluoromethylphenyl | F |
| 766 | CH₂=CH— | | chromane-methyl | | chromane-methyl | OC(CF₃)₂ | difluoromethylphenyl | CF₃ |
| 767 | CH₂=CH— | | chromane-methyl | | chromane-methyl | OC(CF₃)₂ | trifluoromethylphenyl | OCF₃ |

TABLE-continued

Further example compounds

| | $R^1$ | $A^1$ | $W^1$ | $A^2$ | $W^2$ | $Z^4$ | $A^3$ | $R^2$ |
|---|---|---|---|---|---|---|---|---|
| 768 | CH=CH₂ (prop-1-enyl) | | 3-methylchroman | | 7-methylchroman | OCH₃-C(F)(F)- | 2-methyl-5-fluorophenyl-F | CN |
| 769 | $C_3H_7$ | | 3-methylchroman | | 6-fluoro-7-methylchroman | OCH₃-C(F)(F)- | 2-methyl-5-fluorophenyl-F | F |
| 770 | $C_3H_7$ | | 3-methylchroman | | 6-fluoro-7-methylchroman | OCH₃-C(F)(F)- | 2-methyl-5-fluorophenyl-F | $CF_3$ |
| 771 | $C_3H_7$ | | 3-methylchroman | | 6-fluoro-7-methylchroman | OCH₃-C(F)(F)- | 2-methyl-5-fluorophenyl-F | $OCF_3$ |
| 772 | $C_3H_7$ | | 3-methylchroman | | 6-fluoro-7-methylchroman | OCH₃-C(F)(F)- | 2-methyl-5-fluorophenyl-F | CN |
| 773 | $C_5H_{11}$ | | 3-methylchroman | | 6-fluoro-7-methylchroman | OCH₃-C(F)(F)- | 2-methyl-5-fluorophenyl-F | F |

TABLE-continued

Further example compounds

| | $R^1$ | $A^1$ | $W^1$ | $A^2$ | $W^2$ | $Z^4$ | $A^3$ | $R^2$ |
|---|---|---|---|---|---|---|---|---|
| 774 | $C_5H_{11}$— | | 3-methylchroman | | 6-F-7-methylchroman | OCF(CF_3)_2 group | 3,5-difluoro-4-methylphenyl | $CF_3$ |
| 775 | $C_5H_{11}$— | | 3-methylchroman | | 6-F-7-methylchroman | OCF(CF_3)_2 | 3,5-difluoro-4-methylphenyl | $OCF_3$ |
| 776 | $C_5H_{11}$— | | 3-methylchroman | | 6-F-7-methylchroman | OCF(CF_3)_2 | 3,5-difluoro-4-methylphenyl | CN |
| 777 | 1-propenyl | | 3-methylchroman | | 6-F-7-methylchroman | OCF(CF_3)_2 | 3,5-difluoro-4-methylphenyl | F |
| 778 | 1-propenyl | | 3-methylchroman | | 6-F-7-methylchroman | OCF(CF_3)_2 | 3,5-difluoro-4-methylphenyl | $CF_3$ |
| 779 | 1-propenyl | | 3-methylchroman | | 6-F-7-methylchroman | OCF(CF_3)_2 | 3,5-difluoro-4-methylphenyl | $OCF_3$ |

TABLE-continued

Further example compounds

| | $R^1$ | $A^1$ | $W^1$ | $A^2$ | $W^2$ | $Z^4$ | $A^3$ | $R^2$ |
|---|---|---|---|---|---|---|---|---|
| 780 | CH=CH₂ (propenyl) | | 3-methylchroman | | 3-methyl-F,F-chroman | C(F)(F)OCH₃ | 2,6-difluoro-4-methylphenyl | CN |
| 781 | C₃H₇ | | 3-methylchroman | | 3-methyl-F,F-chroman | C(F)(F)OCH₃ | 2,6-difluoro-4-methylphenyl | F |
| 782 | C₃H₇ | | 3-methylchroman | | 3-methyl-F,F-chroman | C(F)(F)OCH₃ | 2,6-difluoro-4-methylphenyl | CF₃ |
| 783 | C₃H₇ | | 3-methylchroman | | 3-methyl-F,F-chroman | C(F)(F)OCH₃ | 2,6-difluoro-4-methylphenyl | OCF₃ |
| 784 | C₃H₇ | | 3-methylchroman | | 3-methyl-F,F-chroman | C(F)(F)OCH₃ | 2,6-difluoro-4-methylphenyl | CN |
| 785 | C₅H₁₁ | | 3-methylchroman | | 3-methyl-F,F-chroman | C(F)(F)OCH₃ | 2,6-difluoro-4-methylphenyl | F |

TABLE-continued
Further example compounds
| | $R^1$ | $A^1$ | $W^1$ | $A^2$ | $W^2$ | $Z^4$ | $A^3$ | $R^2$ |
|---|---|---|---|---|---|---|---|---|
| 786 | $C_5H_{11}-$ | | 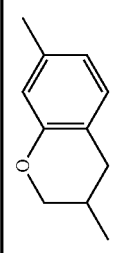 | | 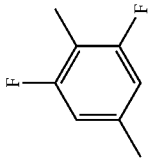 | 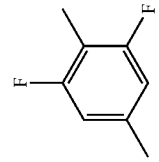 | 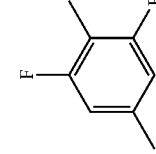 | $CF_3$ |
| 787 | $C_5H_{11}-$ | | 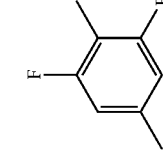 | | 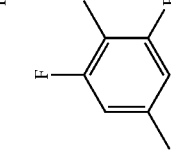 | 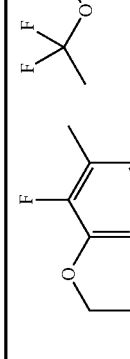 | 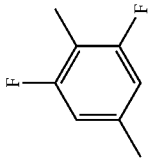 | $OCF_3$ |
| 788 | $C_5H_{11}-$ | | 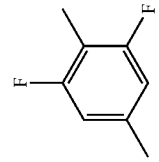 | | 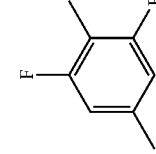 | 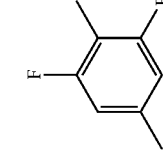 | 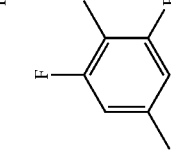 | $CN$ |
| 789 | 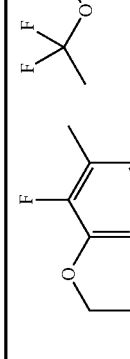 | | 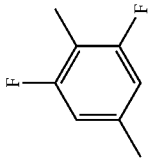 | | 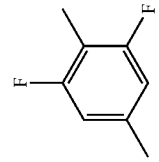 | 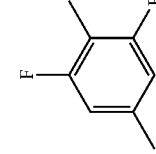 | 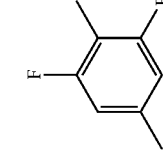 | $F$ |
| 790 | 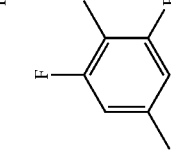 | | 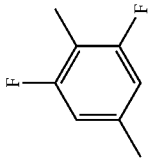 | | 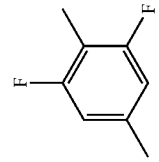 | 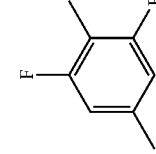 | 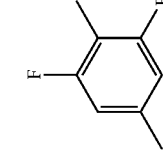 | $CF_3$ |
| 791 | 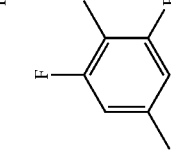 | | 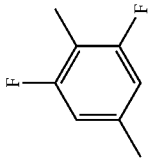 | | 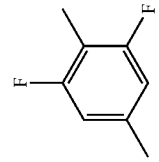 | 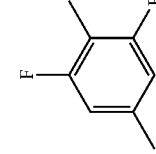 | 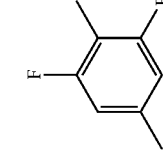 | $OCF_3$ |

TABLE-continued
Further example compounds
| | R¹ | A¹ | W¹ | A² | W² | Z⁴ | A³ | R² |
|---|---|---|---|---|---|---|---|---|
| 792 | 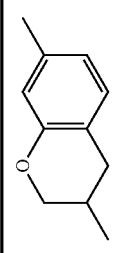 | | 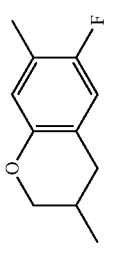 | | 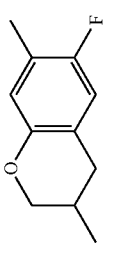 | 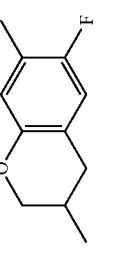 | 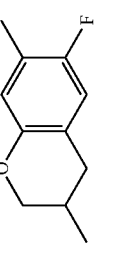 | CN |
| 793 | C₃H₇— | | 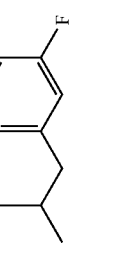 | |  | 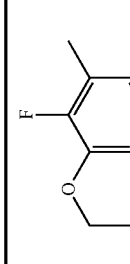 | 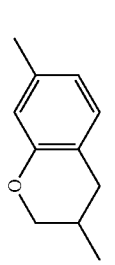 | F |
| 794 | C₃H₇— | | 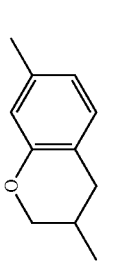 | | 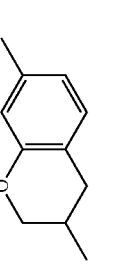 | 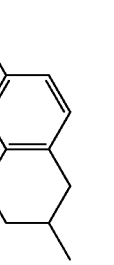 | 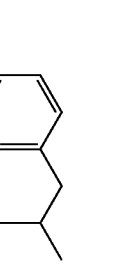 | CF₃ |
| 795 | C₃H₇— | |  | | 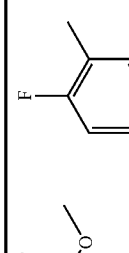 | 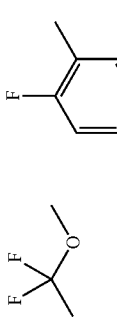 | 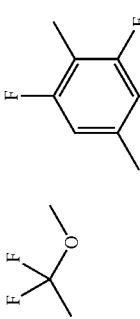 | OCF₃ |
| 796 | C₃H₇— | | 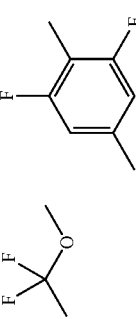 | | 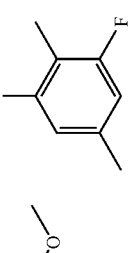 | 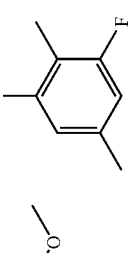 |  | CN |
| 797 | C₅H₁₁— | | 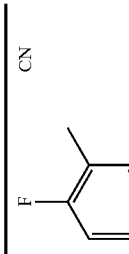 | | 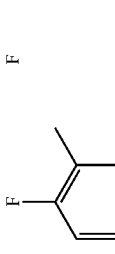 | 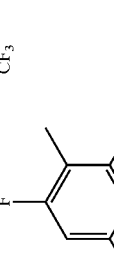 | 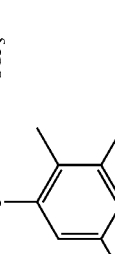 | F |

TABLE-continued

Further example compounds

| | R¹ | A¹ | W¹ | A² | W² | Z⁴ | A³ | R² |
|---|---|---|---|---|---|---|---|---|
| 798 | C₅H₁₁— | | 6-F, 7-Me-3-methylchroman | | 7-Me-3-methylchroman | -C(CF₃)₂-OMe | 2-Me, 3,5-diF phenyl | CF₃ |
| 799 | C₅H₁₁— | | 6-F, 7-Me-3-methylchroman | | 7-Me-3-methylchroman | -C(CF₃)₂-OMe | 2-Me, 3,5-diF phenyl | OCF₃ |
| 800 | C₅H₁₁— | | 6-F, 7-Me-3-methylchroman | | 7-Me-3-methylchroman | -C(CF₃)₂-OMe | 2-Me, 3,5-diF phenyl | CN |
| 801 | CH₃-CH=CH- | | 6-F, 7-Me-3-methylchroman | | 7-Me-3-methylchroman | -C(CF₃)₂-OMe | 2-Me, 3,5-diF phenyl | F |
| 802 | CH₃-CH=CH- | | 6-F, 7-Me-3-methylchroman | | 7-Me-3-methylchroman | -C(CF₃)₂-OMe | 2-Me, 3,5-diF phenyl | CF₃ |
| 803 | CH₃-CH=CH- | | 6-F, 7-Me-3-methylchroman | | 7-Me-3-methylchroman | -C(CF₃)₂-OMe | 2-Me, 3,5-diF phenyl | OCF₃ |

TABLE-continued

Further example compounds

| | R¹ | A¹ | W¹ | A² | W² | Z⁴ | A³ | R² |
|---|---|---|---|---|---|---|---|---|
| 804 | CH=CH₂ (propenyl) | | 6-F-7-Me-3-methylchroman | | 6-F-7-Me-3-methylchroman | OC(CF₃)₂CH₃ | 2,3-difluoro-5-methylphenyl | CN |
| 805 | C₃H₇ | | 6-F-7-Me-3-methylchroman | | 6-F-7-Me-3-methylchroman | OC(CF₃)₂CH₃ | 2,3-difluoro-5-methylphenyl | F |
| 806 | C₃H₇ | | 6-F-7-Me-3-methylchroman | | 6-F-7-Me-3-methylchroman | OC(CF₃)₂CH₃ | 2,3-difluoro-5-methylphenyl | CF₃ |
| 807 | C₃H₇ | | 6-F-7-Me-3-methylchroman | | 6-F-7-Me-3-methylchroman | OC(CF₃)₂CH₃ | 2,3-difluoro-5-methylphenyl | OCF₃ |
| 808 | C₃H₇ | | 6-F-7-Me-3-methylchroman | | 6-F-7-Me-3-methylchroman | OC(CF₃)₂CH₃ | 2,3-difluoro-5-methylphenyl | CN |
| 809 | C₅H₁₁ | | 6-F-7-Me-3-methylchroman | | 6-F-7-Me-3-methylchroman | OC(CF₃)₂CH₃ | 2,3-difluoro-5-methylphenyl | F |

TABLE-continued
Further example compounds
| | R¹ | A¹ W¹ | A² W² | Z⁴ | A³ | R² |
|---|---|---|---|---|---|---|
| 810 | C₅H₁₁— | 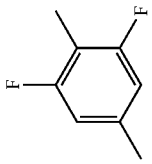 | 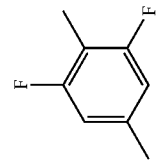 | 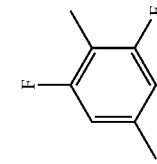 | 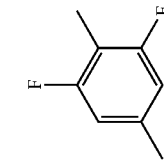 | CF₃ |
| 811 | C₅H₁₁— | 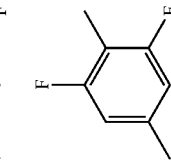 | 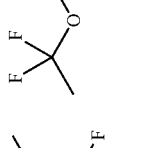 | 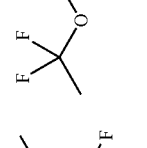 | 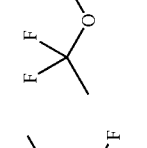 | OCF₃ |
| 812 | C₅H₁₁— | 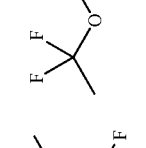 | 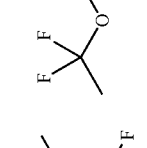 | 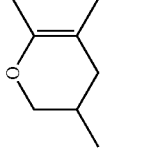 | 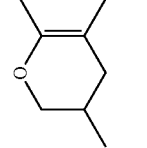 | CN |
| 813 | 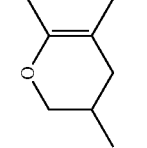 | 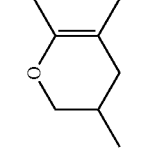 | 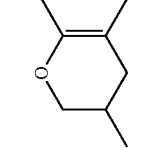 |  |  | F |
| 814 |  |  |  | 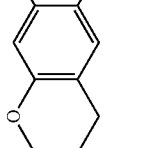 | 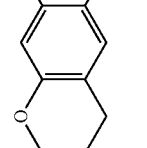 | CF₃ |
| 815 | 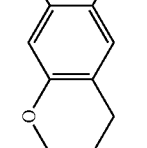 | 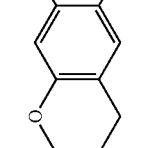 | 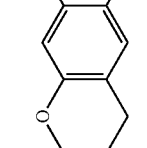 |  |  | OCF₃ |

TABLE-continued
Further example compounds
| R¹ | A¹ | W¹ | A² | W² | Z⁴ | A³ | R² |
|---|---|---|---|---|---|---|---|
| 816 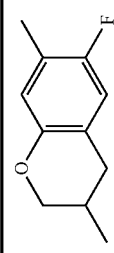 | | 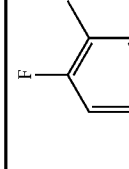 | | 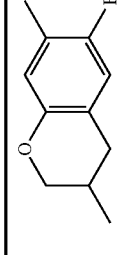 | 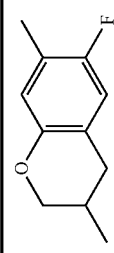 | 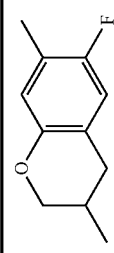 | CN |
| 817 C₃H₇— | | 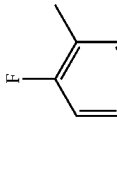 | | 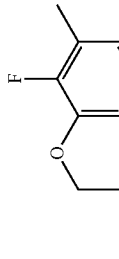 | 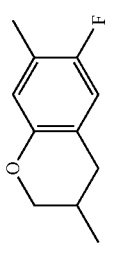 | 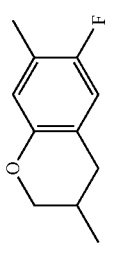 | F |
| 818 C₃H₇— | | 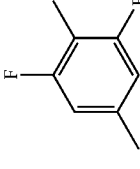 | | 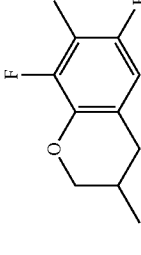 | 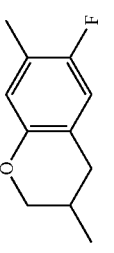 | 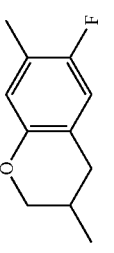 | CF₃ |
| 819 C₃H₇— | | 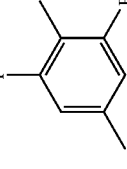 | | 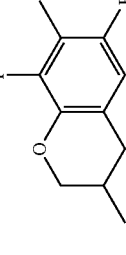 | 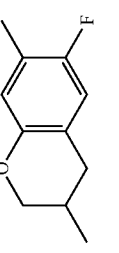 | 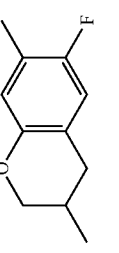 | OCF₃ |
| 820 C₃H₇— | | 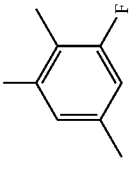 | | 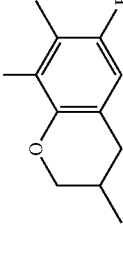 | 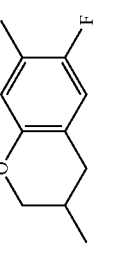 | 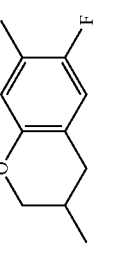 | CN |
| 821 C₅H₁₁— | | 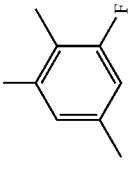 | | 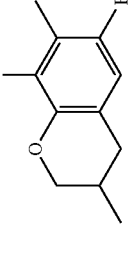 | 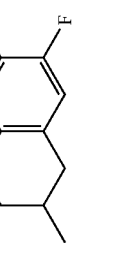 | 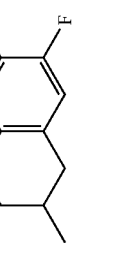 | F |

TABLE-continued

Further example compounds

| | $R^1$ | $A^1$ | $W^1$ | $A^2$ | $W^2$ | $Z^4$ | $A^3$ | $R^2$ |
|---|---|---|---|---|---|---|---|---|
| 822 | $C_5H_{11}-$ | | | | | | | $CF_3$ |
| 823 | $C_5H_{11}-$ | | | | | | | $OCF_3$ |
| 824 | $C_5H_{11}-$ | | | | | | | $CN$ |
| 825 | $CH_3CH=CH-$ | | | | | | | $F$ |
| 826 | $CH_3CH=CH-$ | | | | | | | $CF_3$ |
| 827 | $CH_3CH=CH-$ | | | | | | | $OCF_3$ |

TABLE-continued

Further example compounds

| | $R^1$ | $A^1$ | $W^1$ | $A^2$ | $W^2$ | $Z^4$ | $A^3$ | $R^2$ |
|---|---|---|---|---|---|---|---|---|
| 828 | CH=CH₂ (propenyl) | | chroman-Me, F, Me | | chroman-F, Me, F | OCF₂(Me)O-Me | F, Me, F phenyl | CN |
| 829 | $C_3H_7$ | | | | | | | F |
| 830 | $C_3H_7$ | | | | | | | $CF_3$ |
| 831 | $C_3H_7$ | | | | | | | $OCF_3$ |
| 832 | $C_3H_7$ | | | | | | | CN |
| 833 | $C_5H_{11}$ | | | | | | | F |

TABLE-continued

Further example compounds

| | $R^1$ | $A^1$ | $W^1$ | $A^2$ | $W^2$ | $Z^4$ | $A^3$ | $R^2$ |
|---|---|---|---|---|---|---|---|---|
| 834 | $C_5H_{11}-$ | | chromanyl (F,F,Me) | | chromanyl (F,F,Me) | $CF_2$-O-Me | phenyl (Me,F,F) | $CF_3$ |
| 835 | $C_5H_{11}-$ | | chromanyl (F,F,Me) | | chromanyl (F,F,Me) | $CF_2$-O-Me | phenyl (Me,F,F) | $OCF_3$ |
| 836 | $C_5H_{11}-$ | | chromanyl (F,F,Me) | | chromanyl (F,F,Me) | $CF_2$-O-Me | phenyl (Me,F,F) | CN |
| 837 | CH=CH-Me | | chromanyl (F,F,Me) | | chromanyl (F,F,Me) | $CF_2$-O-Me | phenyl (Me,F,F) | F |
| 838 | CH=CH-Me | | chromanyl (F,F,Me) | | chromanyl (F,F,Me) | $CF_2$-O-Me | phenyl (Me,F,F) | $CF_3$ |
| 839 | CH=CH-Me | | chromanyl (F,F,Me) | | chromanyl (F,F,Me) | $CF_2$-O-Me | phenyl (Me,F,F) | $OCF_3$ |

TABLE-continued

Further example compounds

| R¹ | A¹ | W¹ | A² | W² | Z⁴ | A³ | R² |
|---|---|---|---|---|---|---|---|
| 840 (propenyl H₂C=CH-CH₃) | | 8-F, 7-methyl, 5-F chroman with 3-methyl | | 8-F, 7-methyl, 5-F chroman with 3-methyl | -C(F)(F)(CF₃)-O-CH₃ | 3,5-difluoro-2,6-dimethylphenyl | CN |

Further combinations of the embodiments and variants of the invention arise from the following claims.

The invention claimed is:

1. A compound of formula I

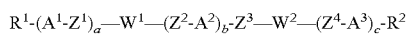

wherein $W^1$, $W^2$, are each, independently of one another, a divalent group of the formula

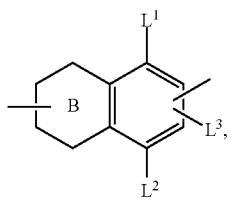

ring B is an unsaturated or partially saturated, six-membered ring in which one or two of the $CH_2$ groups are each replaced by O, where no two O atoms are adjacent, and in which —$CH_2$— is optionally replaced by —CHF— or —$CF_2$—, or =CH— is optionally replaced by =CF—, $L^1$, $L^2$ and $L^3$
are each, independently of one another, H, Cl, F, CN or $CF_3$, $R^1$, $R^2$, are each, independently of one another, Cl, F, CN, SCN, $SF_5$, an alkyl radical having up to 15 C atoms which is unsubstituted, monosubstituted by CN, or at least monosubstituted by halogen, where, in addition, one or more $CH_2$ groups in these radicals are each optionally replaced, independently of one another, by —O—, —CH=CH—, —CF=CF—, —CF=CH—, —C≡C—, —S—, —CO—, —(CO)O—, —O(CO)— or —O(CO)O— in such a way that O atoms are not linked directly to one another, $A^1$, $A^2$ and $A^3$
are each, independently of one another,
(a) a trans-1,4-cyclohexylene radical, in which, in addition, one or more non-adjacent $CH_2$ groups are each optionally replaced by —O— or —S—,
(b) a 1,4-phenylene radical, in which, in addition, one or two CH groups are each optionally replaced by N,
(c) 1,4-cyclohexenylene,
(d) 1,3-bicyclo[1.1.1]pentylene, 1,4-bicyclo[2.2.2]octylene, cyclobut-1,3-diyl, spiro[3.3]heptane-2,6-diyl, naphthalene-2,6-diyl, or tetrahydronaphthalene-2,6-diyl,
where the radicals (a) to (d) are each optionally substituted by one or more fluorine atoms, $Z^1$, $Z^2$, $Z^3$ and $Z^4$
are each, independently of one another, —(CO)O—, —O(CO)—, —$CH_2$O—, —O$CH_2$—, —$CH_2CH_2$—, —CH=CH—, —CH=CF—, —CF=CH—, —CF=CF—, —CHFCHF—, —$CH_2$CHF—, —CHF$CH_2$—, —C≡C—, —$(CH_2)_4$—, —$CF_2$O—, —OCF$_2$—, —$C_2F_4$—, —CH=CH—$CH_2CH_2$—, —$CH_2CH_2$OCF$_2$— or a single bond, and a, b, and c, are each, independently of one another, 0 or 1, where the sum a+b+c is 1 or 2.

2. A compound according to claim 1, wherein $W^1$, $W^2$, are each, independently of one another, a structural element selected from the part-structures (w10), (w11), (w20) and (w21):

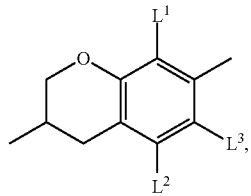
(w10)

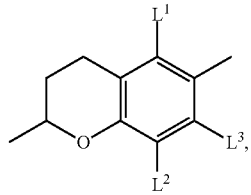
(w20)

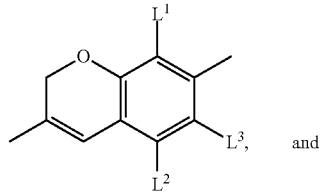
(w11)

and

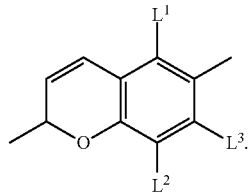
(w21)

3. A compound according to claim 2, wherein $W^1$, $W^2$, are each independently of one another, a structural element selected from the part-structures (w10) and (w20).

4. A compound according to claim 1, wherein $R^1$ is an alkyl radical having up to 15 C atoms which is unsubstituted, monosubstituted by CN, or at least monosubstituted by halogen, where, in addition, one or more $CH_2$ groups are each optionally replaced, independently of one another, by —O—, —CH=CH—, —C≡C—, —S—, —CO—, —(CO)O—, —O(CO)— or —O(CO)O— in such a way that O atoms are not linked directly to one another.

5. A compound according to claim 1, wherein $R^2$ is Cl, F, CN, SCN, $SF_5$, or an alkyl radical having up to 15 C atoms which is monosubstituted by CN or at least monosubstituted by halogen, where, in addition, one or more $CH_2$ groups in the alkyl radical are each optionally replaced, independently of one another, by —O—, —CH=CH—, —CF=CF—, —CF=CH—, —C≡C—, —S—, —CO—, —(CO)O—, —O(CO)— or —O(CO)O— in such a way that O atoms are not linked directly to one another.

6. A compound according to claim 1, wherein the sum of the indices, a+b+c, is 1.

7. A compound according to claim 1, wherein $A^1$, $A^2$ and $A^3$ are each, independently of one another, a divalent group selected from the formulae:

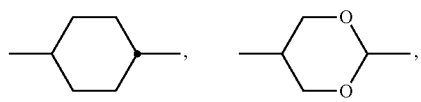

-continued

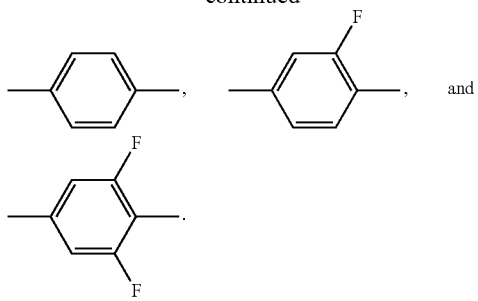

8. A compound according to claim 1, wherein $Z^1$, $Z^2$, $Z^3$ and $Z^4$ are each, independently of one another, a single bond, —CH$_2$CH$_2$—, —CH═CH—, —CH$_2$O— or —CF$_2$O—.

9. A compound according to claim 1, wherein
c denotes 1,
$Z^4$ denotes CF$_2$O, and
$A^3$ denotes a divalent group of the formula

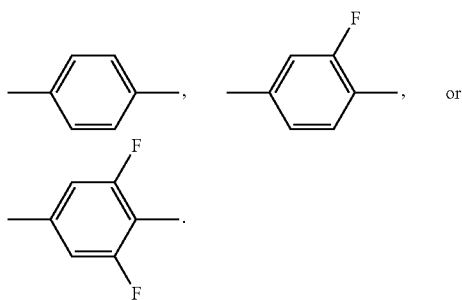

10. A process for the preparation of a compound according to claim 1, in which $A^2$ is a dioxane ring and $Z^2$ and $Z^3$ are single bonds, said process comprising:
reacting a compound of formula II

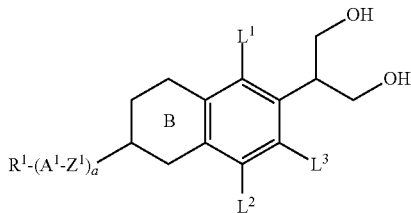

with an aldehyde of formula III

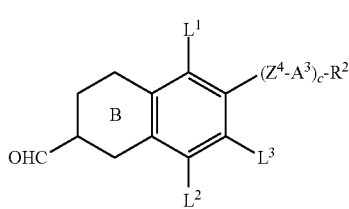

with formation of a dioxane ring.

11. A process for the preparation of a compound according to claim 1, in which b is 0 and $Z^3$ is a single bond, said process comprising:
reacting an oxetane compound of formula IV

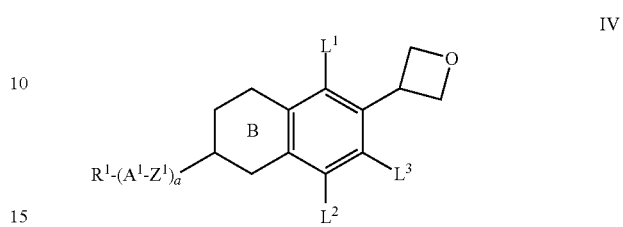

with a bromobenzene compound of formula V

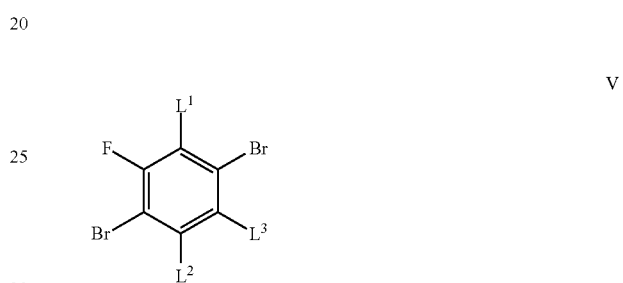

to give a compound of formula VI

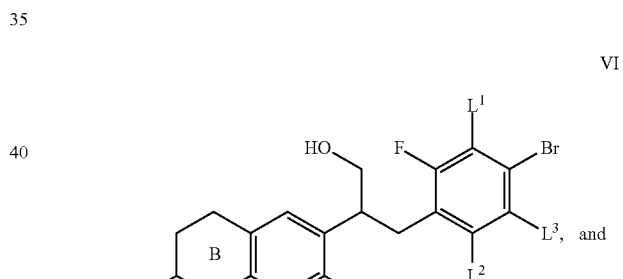

cyclizing said compound of formula VI.

12. A method of using of one or more compounds of the formula I according to claim 1 which comprises using one or more of said compounds as components in a liquid-crystalline medium.

13. A liquid-crystalline medium comprising at least two components, wherein said medium comprises at least one compound according to claim 1.

14. A liquid-crystalline medium according to claim 13, wherein said medium is polymer-stabilized in a blue phase.

15. An electro-optical display element comprising a dielectric, wherein said dielectric is a medium according to claim 13.

16. A compound according to claim 1, wherein
$W^1$, $W^2$, are each, independently of one another, a structural element selected from the part-structures (w10), (w11), (w20) and (w21):

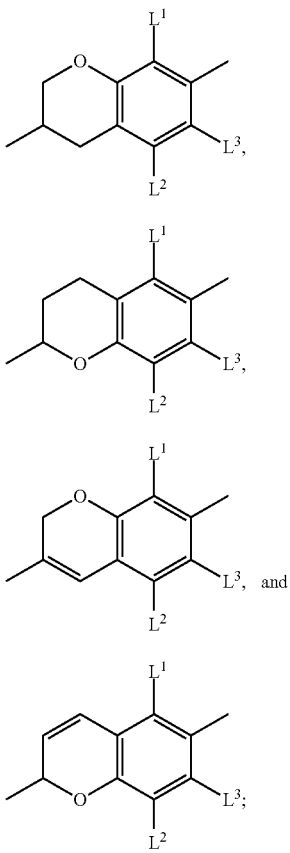

(w10)

(w20)

(w11)

(w21)

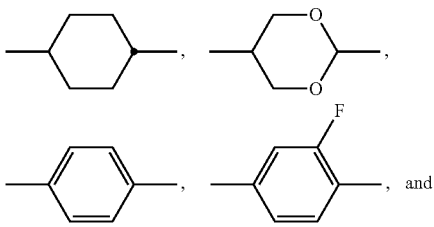

R[1] is an alkyl radical having up to 15 C atoms which is unsubstituted, monosubstituted by CN, or at least monosubstituted by halogen, where, in addition, one or more $CH_2$ groups are each optionally replaced, independently of one another, by —O—, —CH=CH—, —C≡C—, —S—, —CO—, —(CO)O—, —O(CO)— or —O(CO)O— in such a way that O atoms are not linked directly to one another;

R[2] is Cl, F, CN, SCN, $SF_5$, or an alkyl radical having up to 15 C atoms which is monosubstituted by CN or at least monosubstituted by halogen, where, in addition, one or more $CH_2$ groups in the alkyl radical are each optionally replaced, independently of one another, by —O—, —CH=CH—, —CF=CF—, —CF=CH—, —C≡C—, —S—, —CO—, —(CO)O—, —O(CO)— or —O(CO)O— in such a way that O atoms are not linked directly to one another;

A[1], A[2] and A[3] are each, independently of one another, a divalent group selected from the formulae:

$Z^1$, $Z^2$, $Z^3$ and $Z^4$ are each, independently of one another, a single bond, —$CH_2CH_2$—, —CH=CH—, —$CH_2O$— or —$CF_2O$—.

17. A compound of formula I $$R^1\text{-}(A^1\text{-}Z^1)_a\text{---}W^1\text{---}(Z^2\text{-}A^2)_b\text{-}Z^3\text{---}W^2\text{---}(Z^4\text{-}A^3)_c\text{-}R^2 \quad \quad I$$

wherein $W^1$, $W^2$, are each, independently of one another, a divalent group of the formula ring B is an unsaturated or partially saturated, six-membered ring in which one or two of the $CH_2$ groups are each replaced by O, where no two O atoms are adjacent, and in which —$CH_2$— is optionally replaced by —CHF— or —$CF_2$—, or =CH— is optionally replaced by =CF—, $L^1$, $L^2$ and $L^3$ are each, independently of one another, H, Cl, F, CN or $CF_3$, $R^1$, $R^2$, are each, independently of one another, H, Cl, F, CN, SCN, $SF_5$, an alkyl radical having up to 15 C atoms which is unsubstituted, monosubstituted by CN, or at least monosubstituted by halogen, where, in addition, one or more $CH_2$ groups in these radicals are each optionally replaced, independently of one another, by —O—, —CH=CH—, —CF=CF—, —CF=CH—, —C≡C—, —S—, —CO—, —(CO)O—, —O(CO)— or —O(CO)O— in such a way that O atoms are not linked directly to one another, $A^1$ and $A^2$ are each, independently of one another, (a) a trans-1,4-cyclohexylene radical, in which, in addition, one or more non-adjacent $CH_2$ groups are each optionally replaced by —O— or —S—, (b) a 1,4-phenylene radical, in which, in addition, one or two CH groups are each optionally replaced by N, (c) 1,4-cyclohexenylene, (d) 1,3-bicyclo[1.1.1]pentylene, 1,4-bicyclo[2.2.2]octylene, cyclobut-1,3-diyl, spiro[3.3]heptane-2,6-diyl, naphthalene-2,6-diyl, or tetrahydronaphthalene-2,6-diyl, where the radicals (a) to (d) are each optionally substituted by one or more fluorine atoms, A³ is a divalent group selected from

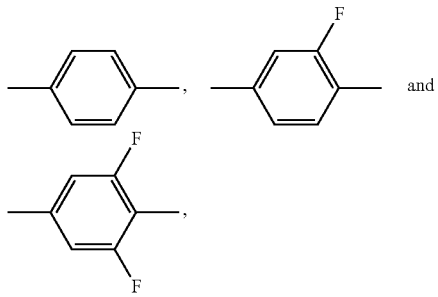

Z¹, Z², and Z³
are each, independently of one another, —(CO)O—, —O(CO)—, —CH₂O—, —OCH₂—, —CH₂CH₂—, —CH═CH—, —CH═CF—, —CF═CH—, —CF═CF—, —CHFCHF—, —CH₂CHF—, —CHFCH₂—, —C≡C—, —(CH₂)₄—, —CF₂O—, —OCF₂—, —C₂F₄—, —CH═CH—CH₂CH₂—, —CH₂CH₂OCF₂— or a single bond, Z⁴ is CF₂O, a and b are each, independently of one another, 0 or 1, c is 1, and the sum a+b+c is 1 or 2.

18. A compound of formula I

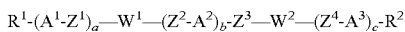

wherein

W¹, W², are each, independently of one another, a divalent group of the formula

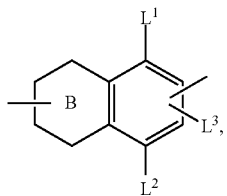

ring B is an unsaturated or partially saturated, six-membered ring in which one or two of the CH₂ groups are each replaced by O, where no two O atoms are adjacent, and in which —CH₂— is optionally replaced by —CHF— or —CF₂—, or ═CH— is optionally replaced by ═CF—, L¹, L² and L³
are each, independently of one another, H, Cl, F, CN or CF₃, R¹, R², are each, independently of one another, Cl, F, CN, SCN, SF₅, an alkyl radical having up to 15 C atoms which is unsubstituted, monosubstituted by CN, or at least monosubstituted by halogen, where, in addition, one or more CH₂ groups in these radicals are each optionally replaced, independently of one another, by —O—, —CH═CH—, —CF═CF—, —CF═CH—, —C≡C—, —S—, —CO—, —(CO)O—, —O(CO)— or —O(CO)O— in such a way that O atoms are not linked directly to one another, A¹, A² and A³
are each, independently of one another,
(a) a trans-1,4-cyclohexylene radical, in which, in addition, one or more non-adjacent CH₂ groups are each optionally replaced by —O— or —S—,
(b) a 1,4-phenylene radical, in which, in addition, one or two CH groups are each optionally replaced by N,
(c) 1,4-cyclohexenylene,
(d) 1,3-bicyclo[1.1.1]pentylene, 1,4-bicyclo[2.2.2]octylene, cyclobut-1,3-diyl, spiro[3.3]heptane-2,6-diyl, naphthalene-2,6-diyl, or tetrahydronaphthalene-2,6-diyl, where the radicals (a) to (d) are each optionally substituted by one or more fluorine atoms, Z¹, Z², Z³ and Z⁴
are each, independently of one another, —(CO)O—, —O(CO)—, —CH₂O—, —OCH₂—, —CH₂CH₂—, —CH═CH—, —CH═CF—, —CF═CH—, —CF═CF—, —CHFCHF—, —CH₂CHF—, —CHFCH₂—, —C≡C—, —(CH₂)₄—, —CF₂O—, —OCF₂—, —C₂F₄—, —CH═CH—CH₂CH₂—, —CH₂CH₂OCF₂— or a single bond, and a, b, c, are each, independently of one another, 0 or 1, where the sum a+b+c is 0, 1 or 2, wherein the group —(Z²-A²)-Z³— is not a single bond.

19. A compound of formula I

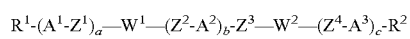

wherein

W¹, W², are each, independently of one another,
a structural element selected from the part-structures (w10), (w11), (w20) and (w21):

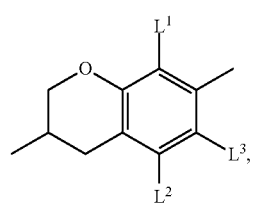

(w10)

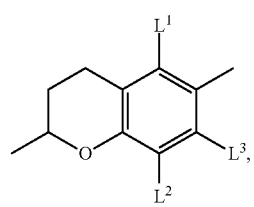

(w20)

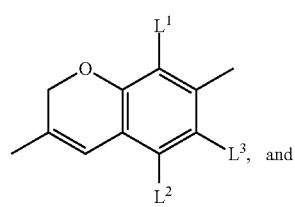

(w11)

-continued (w21)

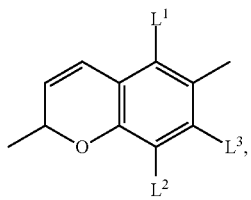

L¹, L² and L³
are each, independently of one another, H, Cl, F, CN or CF₃,

R¹, R², are each, independently of one another, H, Cl, F, CN, SCN, SF₅, an alkyl radical having up to 15 C atoms which is unsubstituted, monosubstituted by CN, or at least monosubstituted by halogen, where, in addition, one or more CH₂ groups in these radicals are each optionally replaced, independently of one another, by —O—, —CH=CH—, —CF=CF—, —CF=CH—, —C≡C—, —S—, —CO—, —(CO)O—, —O(CO)— or —O(CO)O— in such a way that O atoms are not linked directly to one another, A¹, A² and A³
are each, independently of one another,
(a) a trans-1,4-cyclohexylene radical, in which, in addition, one or more non-adjacent CH₂ groups are each optionally replaced by —O— or —S—,
(b) a 1,4-phenylene radical, in which, in addition, one or two CH groups are each optionally replaced by N,
(c) 1,4-cyclohexenylene,
(d) 1,3-bicyclo[1.1.1]pentylene, 1,4-bicyclo[2.2.2]octylene, cyclobut-1,3-diyl, spiro[3.3]heptane-2,6-diyl, naphthalene-2,6-diyl, or tetrahydronaphthalene-2,6-diyl,
where the radicals (a) to (d) are each optionally substituted by one or more fluorine atoms, Z¹, Z², Z³ and Z⁴
are each, independently of one another, —(CO)O—, —O(CO)—, —CH₂O—, —OCH₂—, —CH₂CH₂—, —CH=CH—, —CH=CF—, —CF=CH—, —CF=CF—, —CHFCHF—, —CH₂CHF—, —CHFCH₂—, —C≡C—, —(CH₂)₄—, —CF₂O—, —OCF₂—, —C₂F₄—, —CH=CH—CH₂CH₂—, —CH₂CH₂OCF₂— or a single bond, and a, b, c, are each, independently of one another, 0 or 1, where the sum a+b+c is 0, 1 or 2, wherein at least one of L¹, L² and L³ is not H.

20. A compound according to claim 19, wherein W¹, W², are each independently of one another, a structural element selected from the part-structures (w10) and (w20).

21. A compound according to claim 19, wherein R¹ is an alkyl radical having up to 15 C atoms which is unsubstituted, monosubstituted by CN, or at least monosubstituted by halogen, where, in addition, one or more CH₂ groups are each optionally replaced, independently of one another, by —O—, —CH=CH—, —C≡C—, —S—, —CO—, —(CO)O—, —O(CO)— or —O(CO)O— in such a way that O atoms are not linked directly to one another.

22. A compound according to claim 19, wherein R² is H, Cl, F, CN, SCN, SF₅, or an alkyl radical having up to 15 C atoms which is monosubstituted by CN or at least monosubstituted by halogen, where, in addition, one or more CH₂ groups in the alkyl radical are each optionally replaced, independently of one another, by —O—, —CH=CH—, —CF=CF—, —CF=CH—, —C≡C—, —S—, —CO—, —(CO)O—, —O(CO)— or —O(CO)O— in such a way that O atoms are not linked directly to one another.

23. A compound according to claim 19, wherein
W¹, W², are each, independently of one another, a structural element selected from the part-structures (w10), (w11), (w20) and (w21):

(w10)

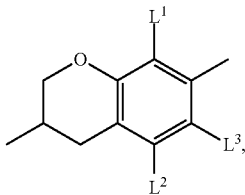

(w20)

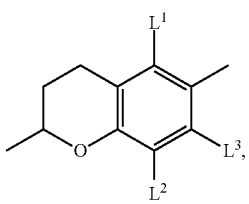

(w11)

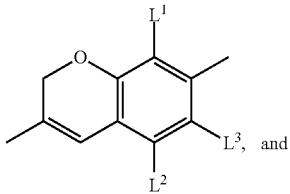
, and (w21)

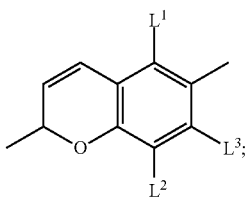
;

R¹ is an alkyl radical having up to 15 C atoms which is unsubstituted, monosubstituted by CN, or at least monosubstituted by halogen, where, in addition, one or more CH₂ groups are each optionally replaced, independently of one another, by —O—, —CH=CH—, —C≡C—, —S—, —CO—, —(CO)O—, —O(CO)— or —O(CO)O— in such a way that O atoms are not linked directly to one another;

R² is H, Cl, F, CN, SCN, SF₅, or an alkyl radical having up to 15 C atoms which is monosubstituted by CN or at least monosubstituted by halogen, where, in addition, one or more CH₂ groups in the alkyl radical are each optionally replaced, independently of one another, by —O—, —CH=CH—, —CF=CF—, —CF=CH—, —C≡C—, —S—, —CO—, —(CO)O—, —O(CO)— or —O(CO)O— in such a way that O atoms are not linked directly to one another;

$A^1$, $A^2$ and $A^3$ are each, independently of one another, a divalent group selected from the formulae:
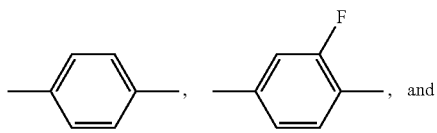,
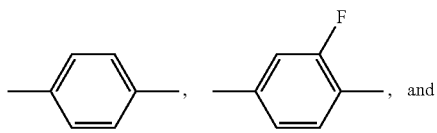, and
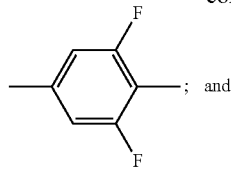; and
$Z^1$, $Z^2$, $Z^3$ and $Z^4$ are each, independently of one another, a single bond, —$CH_2CH_2$—, —CH=CH—, —$CH_2O$— or —$CF_2O$—.
24. A compound according to claim 19, wherein $L^1$, $L^2$, and $L^3$ are each independently H or F.
* * * * *